(12) United States Patent
Lamberth et al.

(10) Patent No.: US 6,683,211 B1
(45) Date of Patent: Jan. 27, 2004

(54) PHENYL-PROPARGYLETHER DERIVATIVES

(75) Inventors: Clemens Lamberth, Efringen-Kirchen (DE); Martin Zeller, Baden (CH); Walter Kunz, Oberwil (CH); Fredrik Cederbaum, Hofstetten (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/276,476

(22) PCT Filed: May 15, 2001

(86) PCT No.: PCT/EO01/05530

§ 371 (c)(1),
(2), (4) Date: Nov. 15, 2002

(87) PCT Pub. No.: WO01/87822

PCT Pub. Date: Nov. 22, 2001

(30) Foreign Application Priority Data

May 17, 2000 (GB) ................................ 0011944

(51) Int. Cl.$^7$ ............. C07C 233/05; A61K 31/165
(52) U.S. Cl. .......... 564/175; 564/139; 564/207; 514/617; 514/622; 514/248; 514/247; 514/438; 514/461; 549/29; 549/429; 544/242; 544/349
(58) Field of Search .................. 564/175, 207, 564/139; 514/617, 622

(56) References Cited

U.S. PATENT DOCUMENTS 6,469,005 B1 * 10/2002 Zeller et al. ............... 564/97

FOREIGN PATENT DOCUMENTS

| EP | 0 251 294 | 1/1988 |
|----|-----------|--------|
| WO | 94/29267  | 12/1994 |
| WO | 95/30651  | 11/1995 |
| WO | 99/07674  | 2/1999 |
| WO | 99/43644  | 9/1999 |
| WO | 00/41998  | 7/2000 |

* cited by examiner

Primary Examiner—Shailendra Kumar
(74) Attorney, Agent, or Firm—Thomas Hamilton

(57) ABSTRACT

The invention relates to phenyl-propargylether derivatives of the general formula I

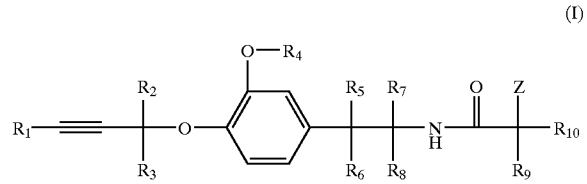

including the optical isomers thereof and mixtures of such isomers, wherein $R_1$ is hydrogen, alkyl, cycloalkyl or optionally substituted aryl, $R_2$ and $R_3$ are each independently hydrogen or alkyl, $R_4$ is alkyl, alkenyl or alkynyl, $R_5$, $R_6$, $R_7$, and $R_8$ are each independently hydrogen or alkyl, $R_9$ is hydrogen, optionally substituted alkyl, optionally substituted alkenyl or optionally substituted alkynyl, $R_{10}$ is optionally substituted aryl or optionally substituted heteroaryl, and Z is halogen, optionally substituted aryloxy, optionally substituted alkoxy, optionally substituted alkenyloxy, optionally substituted alkynyloxy, optionally substituted arylthio, optionally substituted alkylthio, optionally substituted alkenylthio; optionally substituted alkynylthio, optionally substituted alkylsulfinyl, optionally substituted alkenylsulfinyl, optionally substituted alkynylsulfinyl, optionally substituted alkylsulfonyl, optionally substituted alkenylsulfonyl or optionally substituted alkynylsulfonyl. These compounds possess useful plant protecting properties and may advantageously be employed in agricultural practice for controlling or preventing the infestation of plants by phytopathogenic microorganisms, especially fungi.

14 Claims, No Drawings

PHENYL-PROPARGYLETHER DERIVATIVES

This application is a 371 filing of Internation Application No. PCT/EP01/05530, filed May 15, 2001, the contents of which are incorporated herein by reference.

The present invention relates to novel phenyl-propargylether derivatives of formula I below. It relates to the preparation of those substances and to agrochemical compositions comprising at least one of those compounds as active ingredient. The invention relates also to the preparation of the said compositions and to the use of the compounds or of the compositions in controlling or preventing the infestation of plants by phytopathogenic microorganisms, especially fungi.

The invention relates to phenyl-propargylether derivatives of the general formula I

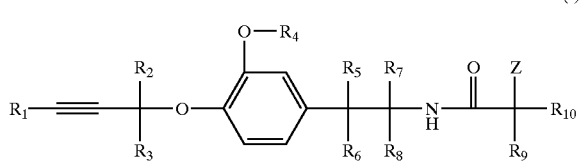

(I)

including the optical isomers thereof and mixtures of such isomers, wherein $R_1$ is hydrogen, alkyl, cycloalkyl or optionally substituted aryl, $R_2$ and $R_3$ are each independently hydrogen or alkyl, $R_4$ is alkyl, alkenyl or alkynyl, $R_5$, $R_6$, $R_7$, and $R_8$ are each independently hydrogen or alkyl, $R_9$ is hydrogen, optionally substituted alkyl, optionally substituted alkenyl or optionally substituted alkynyl, $R_{10}$ is optionally substituted aryl or optionally substituted heteroaryl, and Z is halogen, optionally substituted aryloxy, optionally substituted alkoxy, optionally substituted alkenyloxy, optionally substituted alkynyloxy, optionally substituted arylthio, optionally substituted alkylthio, optionally substituted alkenylthio, optionally substituted alkynylthio, optionally substituted alkylsulfinyl, optionally substituted alkenylsulfinyl, optionally substituted alkynylsulfinyl, optionally substituted alkylsulfonyl, optionally substituted alkenylsulfonyl or optionally substituted alkynylsulfonyl.

In the above definition aryl includes aromatic hydrocarbon rings like phenyl, naphthyl, anthracenyl, phenanthrenyl and biphenyl like 1,3-biphenyl and 1,4-biphenyl, with phenyl being preferred. The same definition applies where aryl is part of aryloxy or arylthio. Heteroaryl stands for aromatic ring systems comprising mono-, bi- or tricyclic systems wherein at least one oxygen, nitrogen or sulfur atom is present as a ring member. Examples are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl and naphthyridinyl.

The above aryl and heteroaryl groups may be optionally substituted. This means that they may carry one or more identical or different substituents. Normally not more than three substituents are present at the same time. Examples of substituents of aryl or heteroaryl groups are: alkyl, alkenyl, alkynyl, cycloalkyl, cycloalkyl-alkyl, phenyl and phenylalkyl, it being possible in turn for all of the preceding groups to carry one or more identical or different halogen atoms; alkoxy; alkenyloxy; alkynyloxy; alkoxyalkyl; haloalkoxy, alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl; or alkynyloxycarbonyl. Typical examples include 4-chlorophenyl, 4-bromophenyl, 3,4-dichlorophenyl, 4-chloro-3-fluorophenyl, 3-chloro-4-fluorophenyl, 4-methylphenyl, 4-ethylphenyl, 4-propargyloxyphenyl, 1-naphtyl, 2-naphtyl, 4-biphenylyl, 4'-chloro-4-biphenylyl, 5-chloro-thien2-yl, 5-methyl-thien-2-yl, 5-methyl-fur-2-yl, 5,6,7,8-tetrahydro-1-naphthyl, 5,6,7,8-tetrahydro-2-naphthyl, 3,4-dioxomethylenyl-phenyl, 3,4-dioxoethylenyl-phenyl, 6-benzothienyl, 7-benzothienyl, 3-methylphenyl, 4-fluorophenyl, 4-ethenylphenyl, 4-ethynylphenyl, 4-propylphenyl, 4-isopropylphenyl, 4-tert.butylphenyl, 4-ethoxyphenyl, 4-ethynyloxyphenyl, 4-phenoxyphenyl, 4-methylthiophenyl, 4-methylsulphonylphenyl, 4-cyanophenyl, 4-nitrophenyl, 4-methoxycarbonylphenyl, 3-bromophenyl, 3-chlorophenyl, 2-chlorophenyl, 2,4-dichlorophenyl, 3,4,5-trichlorophenyl, 3,4-difluorophenyl, 3,4-dibromophenyl, 3,4-dimethoxyphenyl, 3,4-dimethylphenyl, 3-chloro-4-cyanophenyl, 4-chloro-3-cyanophenyl, 3-bromo-4-methylphenyl, 4-methoxy-3-methylphenyl, 3-fluoro-4-methoxyphenyl, 4-chloro-3-methylphenyl, 4-chloro-3-trifluoromethyl-phenyl, 4-bromo-3-chlorophenyl, 4-trifluoromethylphenyl, 4-trifluoromethoxyphenyl, 4-methoxyphenyl, 4'-methyl-4-biphenylyl, 4'-trifluoromethyl-4-biphenylyl, 4'-bromo-4-biphenylyl, 4'-cyano-4-biphenylyl, 3'4'-dichloro-4-biphenylyl, etc.

Again, the same optional substituent may be present where aryl is part of aryloxy or arylthio. Optionally substituted alkyl, alkenyl or alkynyl groups may carry one or more substituents selected from halogen, alkyl, alkoxy, alkylthio, cycloalkyl, phenyl, nitro, cyano, hydroxy, mercapto, alkylcarbonyl or alkoxycarbonyl. This also applies where alkyl, alkenyl or alkynyl is part of another substituent like alkoxy, alkylthio, alkylsulfinyl, alkylsulfonyl, alkenylyoxy, alkenylthio, alkenylsulfinyl, alkenylsufonyl, alkynyloxy, alkynylthio, alkynylsulfinyl and alkynylsulfonyl.

Preferably, the number of substituents is no more than three with the exception of halogen, where the alkyl groups may be perhalogenated.

In the above definitions "halogen" includes fluorine, chlorine, bromine and iodine.

The alkyl, alkenyl and alkynyl radicals may be straight-chain or branched. This applies also to the alkyl, alkenyl or alkynyl parts of other alkyl-, alkenyl- or alkynyl-containing groups.

Depending upon the number of carbon atoms mentioned, alkyl on its own or as part of another substituent is to be understood as being, for example, methyl, ethyl, propyl, butyl, pentyl, hexyl, heptyl, octyl, nonyl, decyl, undecyl, dodecyl and the isomers thereof, for example isopropyl, isobutyl, tert-butyl or sec-butyl, isopentyl or tert-pentyl.

Cycloalkyl is, depending upon the number of carbon atoms mentioned, cyclopropyl, cyclobutyl, cyclopentyl, cyclohexyl, cycloheptyl or cyclooctyl.

Depending upon the number of carbon atoms mentioned, alkenyl as a group or as a structural element of other groups is to be understood as being, for example, ethenyl, allyl, 1-propenyl, buten-2-yl, buten-3-yl, penten-1-yl, penten-3-yl, hexen-1-yl, 4-methyl-3-pentenyl or 4-methyl-3-hexenyl.

Alkynyl as a group or as a structural element of other groups is, for example, ethynyl, propyn-1-yl, propyn-2-yl, butyn-1-yl, butyn-2-yl, 1-methyl-2-butynyl, hexyn-1-yl, 1-ethyl-2-butynyl or octyn-1-yl.

A haloalkyl group may contain one or more (identical or different) halogen atoms, and for example may stand for $CHCl_2$, $CH_2F$, $CCl_3$, $CH_2Cl$, $CHF_2$, $CF_3$, $CH_2CH_2Br$, $C_2Cl_5$, $CH_2Br$, $CHClBr$, $CF_3CH_2$, etc.

The presence of at least one asymmetric carbon atom in the compounds of formula I means that the compounds may occur in optically isomeric and enantiomeric forms. As a result of the presence of a possible aliphatic C=C double bond, geometric isomerism may also occur. Formula I is intended to include all those possible isomeric forms and mixtures thereof.

Preferred subgroups of compounds of formula I are those wherein $R_1$ is hydrogen, alkyl, cycloalkyl, phenyl or naphthyl; phenyl and naphthyl being optionally substituted by substituents selected from the group comprising alkyl, alkenyl, alkynyl, cycloalkyl, cycloalkyl-alkyl, phenyl and phenylalkyl, where all these groups may in turn be substituted by one or several halogens; alkoxy; alkenyloxy; alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl; or alkynyloxycarbonyl; or $R_1$ is hydrogen, $C_1$–$C_8$alkyl, $C_3$–$C_8$cycloalkyl, phenyl or naphthyl; phenyl and naphthyl being optionally substituted by one to three substituents selected from the group comprising $C_1$–$C_8$alkyl, $C_2$–$C_8$alkenyl, $C_2$–$C_8$alkynyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, $C_1$–$C_8$alkylsulfonyl, halogen, cyano, nitro and $C_1$–$C_8$alkoxycarbonyl; or $R_1$ is hydrogen, $C_1$–$C_8$alkyl or phenyl optionally substituted by one to three substituents selected from the group comprising $C_1$–$C_8$alkyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, halogen, cyano, nitro and $C_1$–$C_8$alkoxycarbonyl; or $R_1$ is hydrogen, $C_1$–$C_8$alkyl or $C_3$–$C_8$cycloalkyl; or $R_1$ is hydrogen or $C_1$–$C_4$alkyl; or $R_2$ and $R_3$ are independently of each other hydrogen or $C_1$–$C_4$alkyl; or $R_2$ and $R_3$ are hydrogen; or $R_4$ is $C_1$–$C_8$alkyl, $C_2$–$C_8$alkenyl, or $C_2$–$C_8$alkynyl; or $R_4$ is $C_1$–$C_6$alkyl; or $R_4$ is $C_1$–$C_4$alkyl, or $R_4$ is methyl or ethyl, especially methyl; or $R_5$, $R_6$, $R_7$ and $R_8$ are independently of each other hydrogen or $C_1$–$C_4$alkyl; or $R_5$, $R_6$ and $R_7$ are hydrogen and $R_8$ is hydrogen, methyl or ethyl, preferably methyl; or $R_5$, $R_6$, $R_7$ and $R_8$ are hydrogen; or $R_9$ is hydrogen, $C_1$–$C_4$alkyl, $C_1$–$C_4$haloalkyl, $C_3$–$C_4$alkenyl or $C_3$–$C_4$alkynyl; or $R_9$ is hydrogen or $C_1$–$C_4$alkyl; or $R_9$ is hydrogen; or $R_{10}$ is aryl or heteroaryl, each optionally substituted with substituents selected from the group comprising alkyl, alkenyl, alkynyl, cycloalkyl, cycloalkyl-alkyl, phenyl and phenylalkyl, where all these groups may be substituted with one or more halogen atoms; alkoxy; alkenyloxy; alkynyloxy; alkoxy-alkyl; haloalkoxy; alkylthio; haloalkylthio; alkylsulfonyl; formyl; alkanoyl; hydroxy; cyano; nitro; amino; alkylamino; dialkylamino; carboxyl; alkoxycarbonyl; alkenyloxycarbonyl and alkynyloxycarbonyl; or $R_{10}$ is phenyl, naphthyl or biphenyl, each optionally substituted by one to three substituents selected from the group comprising $C_1$–$C_8$alkyl, $C_2$–$C_8$alkenyl, $C_2$–$C_8$alkynyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, $C_1$–$C_8$alkylsulfonyl, halogen, cyano, nitro and $C_1$–$C_8$alkoxycarbonyl; or $R_{10}$ is phenyl, naphthyl, 1,3-biphenyl or 1,4-biphenyl, each optionally substituted by one to three substituents selected from the group comprising $C_1$–$C_8$alkyl, $C_1$–$C_8$haloalkyl, $C_1$–$C_8$alkoxy, $C_1$–$C_8$haloalkoxy, $C_1C_8$alkylthio, $C_1$–$C_8$haloalkylthio, halogen, cyano, nitro and $C_1$–$C_8$alkoxycarbonyl; or Z is halogen, optionally substituted aryloxy or arylthio wherein in each the aryl may be optionally substituted by one or more substituents selected from the group comprising halogen, $C_1$–$C_8$alkoxy, $C_2$–$C_8$alkenyloxy, $C_2$–$C_8$alkynyloxy, $C_1$–$C_8$alkoxy-$C_1$–$C_8$alkyl, $C_1$–$C_8$haloalkoxy, $C_1$–$C_8$alkylthio, $C_1$–$C_8$haloalkylthio, $C_1$–$C_8$alkylsulfonyl, formyl, $C_2$–$C_8$alkanoyl, hydroxy, halogen, cyano, nitro, amino, $C_1$–$C_8$alkylamino, di-$C_1$–$C_8$alkylamino, carboxyl and $C_1$–$C_8$alkoxycarbonyl; or is optionally substituted $C_1$–$C_8$alkoxy, optionally substituted $C_2$–$C_8$alkenyloxy, optionally substituted $C_2$–$C_8$alkynyloxy, optionally substituted $C_1$–$C_8$alkylthio, optionally substituted $C_2$–$C_8$alkenylthio, optionally substituted $C_2$–$C_8$alkynylthio, optionally substituted $C_1$–$C_8$alkylsulfinyl, optionally substituted $C_2$–$C_8$alkenylsulfinyl, optionally substituted $C_2$–$C_8$alkynylsulfinyl, optionally substituted $C_1$–$C_8$alkylsulfonyl, optionally substituted $C_2$–$C_8$alkenylsulfonyl, or optionally substituted $C_2$–$C_8$alkynylsulfonyl wherein each alkyl, alkenyl or alkynyl group may carry one or more substituents selected from the group comprising halogen, $C_1$–$C_4$alkyl, $C_1$–$C_4$alkoxy, $C_1$–$C_4$alkylthio, $C_3$–$C_6$cycloalkyl, nitro, cyano, hydroxy, phenyl, mercapto, $C_1$–$C_4$alkylcarbonyl and $C_1$–$C_4$alkoxycarbonyl; or Z is halogen; $C_1$–$C_8$alkoxy, $C_2$–$C_8$alkenyloxy, $C_2$–$C_8$alkynyloxy, $C_1$–$C_8$alkoxy-$C_1$–$C_8$alkoxy, $C_2$–$C_8$alkenyloxy-$C_1$–$C_8$alkoxy, $C_2$–$C_8$alkynyloxy-$C_1$–$C_8$alkoxy, $C_1$–$C_8$haloalkoxy, $C_3$–$C_8$-alkyl-$C_1$–$C_8$alkoxy, $C_1$–$C_8$alkylthio, $C_2$–$C_8$alkenylthio, $C_2$–$C_8$alkynylthio, $C_1$–$C_8$haloalkylthio, $C_3$–$C_8$cycloalkyl-$C_1$–$C_8$alkylthio, $C_1$–$C_8$alkylsulfinyl, $C_1$–$C_8$alkylsulfonyl, $C_2$–$C_8$alkenylsulfinyl, $C_2$–$C_8$alkenylsulfonyl, $C_2$–$C_8$alkynylsulfinyl or $C_2$–$C_8$alkynylsulfonyl; or Z is halogen; $C_1$–$C_8$alkoxy, $C_2$–$C_8$alkenyloxy, $C_2$–$C_8$alkynyloxy, $C_1$–$C_8$alkoxy-$C_1$–$C_8$alkoxy, $C_2$–$C_8$alkenyloxy-$C_1$–$C_8$alkoxy, $C_2$–$C_8$alkynyloxy-$C_1$–$C_8$alkoxy, $C_1$–$C_8$haloalkoxy, $C_3$–$C_8$cycloalkyl-$C_1$–$C_8$alkoxy, $C_1$–$C_8$alkylthio, $C_2$–$C_8$alkenylthio, $C_2$–$C_8$alkynylthio, $C_1$–$C_8$haloalkylthio or $C_3$–$C_8$cycloalkyl-$C_1$–$C_8$alkylthio; or Z is halogen; $C_1$–$C_8$alkoxy, $C_2$–$C_8$alkenyloxy, $C_2$–$C_8$alkynyloxy, $C_1$–$C_4$alkoxy-$C_1$–$C_2$alkoxy, $C_1$–$C_8$alkylthio, $C_2$–$C_8$alkenylthio or $C_2$–$C_8$alkynylthio; or Z is $C_1$–$C_8$alkoxy, $C_2$–$C_6$alkenyloxy or $C_2$–$C_6$alkynyloxy.

One preferred subgroup of the compounds of formula I consists of those compounds wherein $R_9$ is hydrogen, and Z is $C_1$–$C_8$alkoxy, $C_2$–$C_6$alkenyloxy or $C_2$–$C_6$alkynyloxy.

Further preferred subgroups are those wherein $R_1$ is hydrogen, alkyl, cycloalkyl, phenyl or naphthyl; phenyl and naphthyl being optionally substituted by substituents selected from the group comprising alkyl, alkenyl, alkynyl, cycloalkyl, cycloalkyl-alkyl, phenyl and phenylalkyl, where all these groups may in turn be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl; or alkynyloxycarbonyl; and $R_4$ is alkyl; and $R_{10}$ is aryl or heteroaryl, each optionally substituted by substituents selected from to group comprising alkyl, alkenyl, alkynyl, cycloalkyl, cycloalkyl-alkyl, phenyl and phenylalkyl, where all these groups may be substituted by one or several halogen; alkoxy; alkenyloxy; alkynyloxy; alkoxy-alkyl; haloalkoxy; alkylthio; haloalkylthio; alkylsulfonyl; formyl; alkanoyl; hydroxy; cyano; nitro; amino; alkylamino; dialkylamino; carboxyl; alkoxycarbonyl; alkenyloxycarbonyl and alkynyloxycarbonyl; and Z is $C_1$–$C_8$alkoxy, $C_2$–$C_6$alkenyloxy or $C_2$–$C_6$alkynyloxy; or $R_1$ is hydrogen, $C_1$–$C_8$alkyl, $C_3$–$C_8$cycloalkyl, phenyl or naphthyl; phenyl and naphthyl being optionally substituted by one to three substituents selected from the group comprising $C_1$–$C_8$alkyl, $C_2$–$C_8$alkenyl, $C_2$–$C_8$alkynyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, $C_1$–$C_8$alkylsulfonyl, halogen, cyano, nitro and $C_1$–$C_8$alkoxycarbonyl; and $R_2$, $R_3$, $R_5$, $R_6$, and $R_7$ are hydrogen; and $R_4$ and $R_8$ are independently $C_1$–$C_6$alkyl; and $R_{10}$ is phenyl, naphthyl, 1,3-biphenyl or 1,4-biphenyl, each optionally substituted by one to three substituents selected from the group comprising $C_1$–$C_8$alkyl, $C_2$–$C_8$alkenyl, $C_2$–$C_8$alkynyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, $C_1$–$C_8$alkylsulfonyl, halogen, cyano, nitro and $C_1$–$C_8$alkoxycarbonyl; and $R_9$ is hydrogen or $C_1$–$C_4$alkyl; and Z is $C_1$–$C_8$alkoxy, $C_2$–$C_6$alkenyloxy or $C_2$–$C_6$alkynyloxy; or $R_1$ is hydrogen, $C_1$–$C_8$alkyl, phenyl optionally substituted by one to three substituents selected from the group comprising $C_1$–$C_8$alkyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, halogen, cyano, nitro and $C_1$–$C_8$alkoxycarbonyl; and $R_2$, $R_3$, $R_5$, $R_6$, and $R_7$ are hydrogen; and $R_4$ and $R_8$ are each independently methyl or ethyl; and $R_{10}$ is phenyl, naphthyl, 1,3-biphenyl or 1,4-biphenyl, each optionally substituted by one to three substituents selected from the group comprising $C_1$–$C_8$alkyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, halogen, cyano, nitro and $C_8$alkoxycarbonyl; $R_9$ is hydrogen and Z is $C_1$–$C_8$alkoxy, $C_2$–$C_6$alkenyloxy or $C_2$–$C_6$alkynyloxy.

Other preferred subgroups of the compounds of formula I are those wherein $R_1$ is hydrogen, alkyl, cycloalkyl, phenyl or naphthyl; phenyl and naphthyl being optionally substituted by substituents selected from the group comprising alkyl, alkenyl, alkynyl, cycloalkyl, cycloalkyl-alkyl, phenyl and phenylalkyl, where all these groups may in turn be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl; or alkynyloxycarbonyl; and $R_2$ and $R_3$ are independently of each other hydrogen or $C_1$–$C_4$alkyl; and $R_4$ is $C_1$–$C_8$alkyl, $C_2$–$C_8$alkenyl, or $C_2$–$C_8$alkynyl; and $R_5$, $R_6$, $R_7$ and $R_8$ are independently of each other hydrogen or $C_1$–$C_4$alkyl; and $R_9$ is hydrogen, $C_1$–$C_4$alkyl, $C_1$–$C_4$haloalkyl, $C_3$–$C_4$alkenyl or $C_3$–$C_4$alkynyl; and $R_{10}$ is aryl or heteroaryl, each optionally substituted with substituents selected from to group comprising alkyl, alkenyl, alkynyl, cycloalkyl, cycloalkyl-alkyl, phenyl and phenylalkyl, where all these groups may be substituted with one or more substituents selected from the group comprising halogen; alkoxy, alkenyloxy, alkynyloxy; alkoxy-alkyl; haloalkoxy; alkylthio; haloalkylthio; alkylsulfonyl; formyl; alkanoyl; hydroxy; cyano; nitro; amino; alkylamino; dialkylamino; carboxyl; alkoxycarbonyl; alkenyloxycarbonyl and alkynyloxycarbonyl; and Z is halogen, optionally substituted aryloxy or arylthio wherein in each the aryl may be optionally substituted by one or more substituents selected from the group comprising halogen, $C_{1-8}$alkoxy, $C_2$–$C_8$alkenyloxy, $C_2$–$C_8$alkynyloxy, $C_1$–$C_8$alkoxy-$C_1$–$C_8$alkyl, $C_1$–$C_8$haloalkoxy, $C_1$–$C_8$alkylthio, $C_1$–$C_8$haloalkylthio, $C_1$–$C_8$alkylsulfonyl, formyl, $C_2$–$C_8$alkanoyl, hydroxy, halogen, cyano, nitro, amino, $C_1$–$C_8$alkylamino, di-$C_1$–$C_8$alkylamino, carboxyl and $C_1$–$C_8$alkoxycarbonyl; or is optionally substituted $C_1$–$C_8$alkoxy, optionally substituted $C_2$–$C_8$alkenyloxy, optionally substituted $C_2$–$C_8$alkynyloxy, optionally substituted $C_1C_8$alkylthio, optionally substituted $C_2$–$C_8$alkenylthio, optionally substituted $C_2$–$C_8$alkynylthio, optionally substituted $C_1$–$C_8$alkylsulfinyl, optionally substituted $C_2$–$C_8$alkenylsulfinyl, optionally substituted $C_2$–$C_8$alkynylsulfinyl, optionally substituted $C_1$–$C_8$alkylsulfonyl, optionally substituted $C_2$–$C_8$alkenylsulfonyl or optionally substituted $C_2$–$C_8$alkynylsulfonyl wherein each alkyl, alkenyl or alkynyl group may carry one or more substituents selected from the group comprising halogen, $C_1$–$C_4$alkyl, $C_1$–$C_4$alkoxy, $C_1$–$C_4$alkylthio, $C_3$–$C_6$cycloalkyl, nitro, cyano, hydroxy, phenyl, mercapto, $C_1$–$C_4$alkylcarbonyl and $C_1$–$C_4$alkoxycarbonyl; or wherein $R_1$ is hydrogen, $C_1$–$C_8$alkyl, $C_3$–$C_8$cycloalkyl, phenyl or naphthyl; phenyl and naphthyl being optionally substituted by one to three substituents selected from the group comprising $C_1$–$C_8$alkyl, $C_2$–$C_8$alkenyl, $C_2$–$C_8$alkynyl, $C_1$–$C_8$haloalkyl, $C_1$–$C_8$alkoxy, $C_1$–$C_{C8}$haloalkoxy, $C_1$–$C_8$alkylthio, $C_1$–$C_8$haloalkylthio, $C_1$–$C_8$alkylsulfonyl, halogen, cyano, nitro and $C_1$–$C_8$alkoxycarbonyl; and $R_2$ and $R_3$ are hydrogen; and $R_4$ is $C_1$–$C_6$alkyl; and $R_5$, $R_6$ and $R_7$ are hydrogen and $R_8$ is hydrogen, methyl or ethyl, preferably methyl; and R₉ is hydrogen or C₁–C₄alkyl; and R₁₀ is phenyl, naphthyl or biphenyl, each optionally substituted by one to three substituents selected from the group comprising C₁–C₈alkyl, C₂–C₈alkenyl, C₂–C₈alkynyl, C₁–C₈haloalkyl, C₁–C₈alkoxy, C₁–C₈haloalkoxy, C₁–C₈alkylthio, C₁–C₈haloalkylthio, C₁–C₈alkylsulfonyl, halogen, cyano, nitro and C₁–C₈alkoxycarbonyl; and Z is halogen; C₁–C₈alkoxy, C₂–C₈alkenyloxy, C₁–C₈alkynyloxy, C₁–C₈alkoxy-C₁–C₈alkoxy, C₂–C₈alkenyloxy-C₁–C₈alkoxy, C₂–C₈alkynyloxy-C₁–C₈alkoxy, C₁–C₈haloalkoxy, C₃–C₈cycloalkyl-C₁–C₈alkoxy, C₁–C₈alkylthio, C₂–C₈alkenylthio, C₁–C₈alkynylthio, C₁–C₈haloalkylthio, C₃–C₈cycloalkyl-C₁–C₈alkylthio, C₁–C₈alkylsulfinyl, C₁–C₈alkylsulfonyl, C₂–C₈alkenylsulfinyl, C₂–C₈alkenylsulfonyl, C₂–C₈alkynylsulfinyl or C₂–C₈alkynylsulfonyl; or wherein R₁ is hydrogen, C₁–C₈alkyl or phenyl optionally substituted by one to three substituents selected from the group comprising C₁–C₈alkyl, C₁–C₈haloalkyl, C₁–C₈alkoxy, C₁–C₈haloalkoxy, C₁–C₈alkylthio, C₁–C₈haloalkylthio, halogen, cyano, nitro and C₁–C₈alkoxycarbonyl; and R₂ and R₃ are hydrogen; and R₄ is C₁–C₄alkyl, and R₅, R₆ and R₇ are hydrogen and R₈ is hydrogen or methyl; and R₉ is hydrogen; and R₁₀ is phenyl, naphthyl, 1,3-biphenyl or 1,4-biphenyl, each optionally substituted by one to three substituents selected from the group comprising C₁–C₈alkyl, C₁–C₈haloalkyl, C₁–C₈alkoxy, C₁–C₈haloalkoxy, C₁–C₈alkylthio, C₁–C₈haloalkylthio, halogen, cyano, nitro and C₁–C₈alkoxycarbonyl; and Z is halogen; C₁–C₈alkoxy, C₂–C₈alkenyloxy, C₂–C₈alkynyloxy, C₁–C₄alkoxy-C₁–C₂alkoxy, C₂–C₈alkylthio, C₂–C₈alkenylthio or C₂–C₈alkynylthio; or wherein R₁ is hydrogen, C₁–C₈alkyl or C₃–C₈cycloalkyl; and R₂, R₃, R₅, R₆, R₇, R₈ and R₉ are hydrogen; and R₄ is methyl or ethyl; and R₁₀ is phenyl, naphthyl, 1,3-biphenyl or 1,4-biphenyl, each optionally substituted by one to three substituents selected from the group comprising C₁–C₈alkyl, C₁–C₈haloalkyl, C₁–C₈alkoxy, C₁–C₈haloalkoxy, C₁–C₈alkylthio, C₁–C₈haloalkylthio, halogen, cyano, nitro and C₁–C₈alkoxycarbonyl; and Z is C₁–C₈alkoxy, C₂–C₆alkenyloxy or C₂–C₆alkynyloxy.

Preferred individual compounds are:

2-(4-bromo-phenyl)-2-chloro-N-[2-(3-methoxy-4-prop-2-ynyloxy-phenyl)-ethyl]-acetamide,
2-chloro-2-(4-chloro-phenyl)-N-[2-(3-methoxy-4prop-2-ynyloxy-phenyl)-ethyl]-acetamide,
2-chloro-2-(3,4-dichloro-phenyl)-N-[2-(3-methoxy-4-prop-2-ynyloxy-phenyl)-ethyl]-acetamide,
2-(4-bromo-phenyl)-2-methoxy-N-[2-(3-methoxy-4-prop-2-ynyloxy-phenyl)-ethyl]-acetamide,
2-(4-chloro-phenyl)-2-methoxy-N-[2-(3-methoxy-4-prop-2-ynyloxy-phenyl)-ethyl]-acetamide,
2-(3,4-dichloro-phenyl)-2-methoxy-N-[2-(3-methoxy-4-prop-2-ynyloxy-phenyl)-ethyl]-acetamide,
2-(4-bromo-phenyl)-2-ethoxy-N-[2-(3-methoxy-4-prop-2-ynyloxy-phenyl)-ethyl]-acetamide,
2-(4-chloro-phenyl)-2-ethoxy-N-[2-(3-methoxy-4-prop-2-ynyloxy-phenyl)-ethyl]-acetamide,
2-(3,4-dichloro-phenyl)-2-ethoxy-N-[2-(3-methoxy-4-prop-2-ynyloxy-phenyl)-ethyl]-acetamide,
2-(4-bromo-phenyl)-N-[2-(3-methoxy-4-prop-2-ynyloxy-phenyl)-ethyl]-2-propoxy-acetamide,
2-(4-chloro-phenyl)-N-[2-(3-methoxy-4-prop-2-ynyloxy-phenyl)-ethyl]-2-propoxy-acetamide,
2-(3,4-dichloro-phenyl)-N-[2-(3-methoxy-4-prop-2-ynyloxy-phenyl)-ethyl]-2-propoxy-acetamide,
2-(4-bromo-phenyl)-2-cyclopropylmethoxy-N-[2-(3-methoxy-4-prop-2-ynyloxy-phenyl)-ethyl]-acetamide,
2-(4-chloro-phenyl)-2-cyclopropylmethoxy-N-[2-(3-methoxy-4-prop-2-ynyloxy-phenyl)-ethyl]-acetamide,
2-cyclopropylmethoxy-2-(3,4-dichloro-phenyl)-N-[2-(3-methoxy-4-prop-2-ynyloxy-phenyl)-ethyl]-acetamide,
2-(4-bromo-phenyl)-2-ethoxymethoxy-N-[2-(3-methoxy-4-prop-2-ynyloxy-phenyl)-ethyl]-acetamide,
2-(4-chloro-phenyl)-2-ethoxymethoxy-N-[2-(3-methoxy-4-prop-2-ynyloxy-phenyl)-ethyl]-acetamide,
2-(3,4-dichloro-phenyl)-2-ethoxymethoxy-N-[2-(3-methoxy-4-prop-2-ynyloxy-phenyl)-ethyl]-acetamide,
2-allyloxy-2-(4-bromo-phenyl)-N-[2-(3-methoxy-4-prop-2-ynyloxy-phenyl)-ethyl]-acetamide,
2-allyloxy-2-(4-chloro-phenyl)-N-[2-(3-methoxy-4-prop-2-ynyloxy-phenyl)-ethyl]-acetamide,
2-allyloxy-2-(3,4-dichloro-phenyl)-N-[2-(3-methoxy-4-prop-2-ynyloxy-phenyl)-ethyl]-acetamide,
2-(4-bromo-phenyl)-2-(but-2-ynyloxy)-N-[2-(3-methoxy-4-prop-2-ynyloxy-phenyl)-ethyl]-acetamide,
2-(but-2-enyloxy)-2-(4-chloro-phenyl)-N-[2-(3-methoxy-4-prop-2-ynyloxy-phenyl)-ethyl]-acetamide,
2-(but-2-enyloxy)-2-(3,4-dichloro-phenyl)-N-[2-(3-methoxy-4-prop-2-ynyloxy-phenyl)-ethyl]-acetamide,
2-(4-bromo-phenyl)-N-[2-(3-methoxy-4-prop-2-ynyloxy-phenyl)-ethyl]-2-prop-2-ynyloxy-acetamide,
2-(4-chloro-phenyl)-N-[2-(3-methoxy-4-prop-2-ynyloxy-phenyl)-ethyl]-2-prop-2-ynyloxy-acetamide,
2-(3,4-dichloro-phenyl)-N-[2-(3-methoxy-4-prop-2-ynyloxy-phenyl)-ethyl]-2-prop-2-ynyloxy-acetamide,
2-biphenyl-4-yl-N-[2-(3-methoxy-4-prop-2-ynyloxy-phenyl)-ethyl]-2-prop-2-ynyloxy-acetamide,
N-[2-(3-methoxy-4-prop-2-ynyloxy-phenyl)-ethyl]-2-naphthalen-2-yl-2-prop-2-ynyloxy-acetamide,
N-[2-(3-methoxy-4-prop-2-ynyloxy-phenyl)-ethyl]-2-prop-2-ynyloxy-2-p-tolyl-acetamide,
2-(4-ethyl-phenyl)-N-[2-(3-methoxy-4-prop-2-ynyloxy-phenyl)-ethyl]-2-prop-2-ynyloxy-acetamide,
N-[2-(3-methoxy-4-prop-2-ynyloxy-phenyl)-ethyl]-2-prop-2-ynyloxy-2-(4-trifluoromethyl-phenyl)-acetamide,
2-(4-bromo-phenyl)-2-but-2-ynyloxy-N-[2-(3-methoxy-4-prop-2-ynyloxy-phenyl)-ethyl]-acetamide, 2-but-2-ynyloxy-2-(4-chloro-phenyl)-N-[2-(3-methoxy-4-prop-2-ynyloxy-phenyl)-ethyl]-acetamide,
2-but-2-ynyloxy-2-(3,4-dichloro-phenyl)-N-[2-(3-methoxy-4-prop-2-ynyloxy-phenyl)-ethyl]-acetamide,
2-(4-bromo-phenyl)-N-[2-(3-methoxy-4-prop-2-ynyloxy-phenyl)-ethyl]-2-prop-2-ynylsulfanyl-acetamide,
2-(4-chloro-phenyl)-N-[2-(3-methoxy-4-prop-2-ynyloxy-phenyl)-ethyl]-2-prop-2-ynylsulfanyl-acetamide,
2-(3,4-dichloro-phenyl)-N-[2-(3-methoxy-4-prop-2-ynyloxy-phenyl)-ethyl]-2-prop-2-ynylsulfanyl-acetamide,
2-allylsulfanyl-2-(4-bromo-phenyl)-phenyl)-N-[2-(3-methoxy-4-prop-2-ynyloxy-phenyl)-ethyl]-acetamide,
2-allylsulfanyl-2-(4-chloro-phenyl)-N-[2-(3-methoxy-4-prop-2-ynyloxy-phenyl)-ethyl]-acetamide, 2-allylsulfanyl-2-(4-chloro-phenyl)-N-[2-(3-methoxy-4-prop-2-ynyloxy-phenyl)-ethyl]-acetamide, 2-(4-bromo-phenyl)-N-[2-(3-methoxy-4-pent-2-ynyloxy-phenyl)-ethyl]2-prop-2-ynyloxy-acetamide, 2-(4-chloro-phenyl)-N-[2-(3-methoxy-4-pent-2-ynyloxy-phenyl)-ethyl]-2-prop-2-ynyloxy-acetamide, 2-(3,4-dichloro-phenyl)-N-[2-(3-methoxy-4-pent-2-ynyloxy-phenyl)-ethyl]-2-prop-2-ynyloxy-acetamide, 2-(4-fluoro-phenyl)-N-[2-(3-methoxy-4-prop-2-ynyloxy-phenyl)-ethyl]-2-prop-2-ynyloxy-acetamide, 2-(3,4-difluoro-phenyl)-N-[2-(3-methoxy-4-prop-2-ynyloxy-phenyl)-ethyl]-2-prop-2-ynyloxy-acetamide, 2-(4-chloro-3-fluoro-phenyl)-N-[2-(3-methoxy-4-prop-2-ynyloxy-phenyl)-ethyl]-2-prop-2-ynyloxy-acetamide, and 2-(3-chloro-4-fluoro-phenyl)-N-[2-(3-methoxy-4-prop-2-ynyloxy-phenyl)-ethyl]-2-prop-2-ynyloxy-acetamide.

Certain mandelic acid derivatives have been proposed for controlling plant-destructive fungi (for example in WO 94/29267 and in WO 96/17840). The action of those preparations is not, however, satisfactory in all aspects of agricultural needs. Surprisingly, with the compound structure of formula I, new kinds of microbiocides having a high level of activity have been found.

The propargylether derivatives of formula I and displayed subformulae and intermediates may be obtained according to one of the processes of Schemes 1 to 4:

Scheme 1:

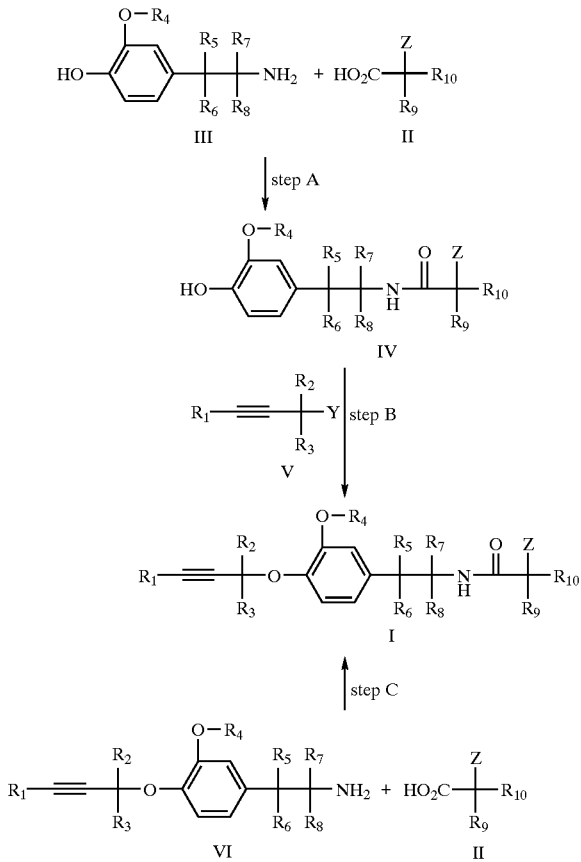

Step A

An acid of formula II or a carboxy-activated derivative of an acid of formula II wherein $R_9$, $R_{10}$ and Z are as defined for formula I is reacted with an amine of formula III wherein $R_4$, $R_5$, $R_6$, $R_7$ and $R_8$ are as defined for formula I, optionally in the presence of a base and optionally in the presence of a diluting agent.

Carboxy-activated derivatives of the acid of formula II are all compounds having an activated carboxyl group like an acid halide, such as an acid chloride, like symmetrical or mixed anhydrides, such as mixed anhydrides with O-alkylcarbonates, like activated esters, such as p-nitrophenylesters or N-hydroxysuccinimidesters, as well as in-situ-formed activated forms of the amino acid of formula II with condensating agents, such as dicyclohexylcarbodiimide, carbonyldiimidazole, benzotriazol-1-yloxy-tris(dimethylamino)phosphonium hexafluorophosphate, O-benzotriazol-1-yl N,N,N',N'-bis(pentamethylene)uronium hexafluorophosphate, O-benzotriazol-1-yl N,N,N',N'-bis(tetramethylene)uronium hexafluorophosphate, O-benzotriazol-1-yl N,N,N',N'-tetramethyluronium hexafluorophosphate or benzotriazol-1-yloxy-tripyrrolidinophosphonium hexafluorophosphate. The mixed anhydrides of the acids of the formula II may be prepared by reaction of an amino acid of formula II with chloroformic acid esters like chloroformic acid alkylesters, such as ethyl chloroformate or isobutyl chloroformate, optionally in the presence of an organic or inorganic base like a tertiary amine, such as triethylamine, N,N-diisopropyl-ethylamine, pyridine, N-methyl-piperidine or N-methyl-morpholine.

The present reaction is preferably performed in a solvent like aromatic, non-aromatic or halogenated hydrocarbons, such as chlorohydrocarbons e.g. dichloromethane or toluene; ketones e.g. acetone; esters e.g. ethyl acetate; amides e.g. N,N-dimethylformamide; nitriles e.g. acetonitrile; or ethers e.g. diethylether, tert-butyl-methylether, dioxane or tetrahydrofurane or water. It is also possible to use mixtures of these solvents. The reaction is performed optionally in the presence of an organic or inorganic base like a tertiary amine, e.g. triethylamine, N,N-diisopropyl-ethylamine, pyridine, N-methyl-piperidine or N-methyl-morpholine, like a metal hydroxide or a metal carbonate, preferentially an alkali hydroxide or an alkali carbonate, such as lithium hydroxide, sodium hydroxide or potassium hydroxide at temperatures ranging from −80° C. to +150° C., preferentially at temperatures ranging from −40° C. to +40° C.

Step B

The compounds of formula I may then finally be prepared by reacting a phenol of formula IV wherein $R_4$, $R_5$, $R_6$, $R_7$, $R_8$, $R_9$, $R_{10}$ and Z are as defined for formula I with a compound of formula V wherein $R_1$, $R_2$ and $R_3$ are as defined for formula I and wherein Y is a leaving group like a halide such as a chloride or bromide or a sulfonic ester such as a tosylate, mesylate or triflate.

The reaction is advantageously performed in a solvent like aromatic, non-aromatic or halogenated hydrocarbons, such as chlorohydrocarbons e.g. dichloromethane or toluene; ketones e.g. acetone or 2-butanone; esters e.g. ethyl acetate; ethers e.g. diethylether, tert-butyl-methylether, dioxane or tetrahydrofurane, amides e.g. dimethylformamide, nitriles e.g. acetonitrile, alcohols e.g. methanol, ethanol, isopropanol, n-butanol or tert-butanol, sulfoxides e.g. dimethylsulfoxide or water. It is also possible to use mixtures of these solvents. The reaction is performed optionally in the presence of an organic or inorganic base like a tertiary amine, such as triethylamine, N,N-diisopropyl-ethylamine, pyridine, N-methyl-piperidine or N-methyl-morpholine, like a metal hydroxide, a metal carbonate or a metal alkoxide, preferentially an alkali hydroxide, an alkali carbonate or an alkali alkoxide, such as lithium hydroxide, sodium hydroxide, potassium hydroxide, sodium carbonate, potassium carbonate, sodium methoxide, potassium methoxide, sodium ethoxide, potassium ethoxide, sodium tert-butoxide or potassium tert-butoxide at temperatures ranging from −80° C. to +200° C., preferentially at temperatures ranging from 0° C. to +120° C.

Step C

Alternatively to step A and step B, an acid of formula II or a carboxy-activated derivative of an acid of formula II wherein $R_9$, $R_{10}$ and Z are as defined for formula I is reacted with an amine of formula VI wherein $R_1$, $R_2$, $R_3$, $R_4$, $R_5$, $R_6$, $R_7$ and $R_8$ are as defined for formula I under the same conditions as defined for step A, optionally in the presence of a base and optionally in the presence of a diluting agent.

Step D

A compound of formula VII wherein $R_4$, $R_5$, $R_6$, $R_7$ and $R_8$ are as defined for formula I is alkylated with a compound of formula V (see Scheme 1) wherein $R_1$, $R_2$, $R_3$ and Y are as defined for Scheme 1 under the same conditions as defined for step B in Scheme 1.

Step E

A compound of formula VIII wherein $R_1$, $R_2$, $R_3$, $R_4$, $R_5$, $R_6$, $R_7$ and $R_8$ are as defined for formula I is dehydrated to an isocyanide of formula IX wherein $R_1$, $R_2$, $R_3$, $R_4$, $R_5$, $R_6$, $R_7$ and $R_8$ are as defined for formula I under conditions known peruse (D. Seebach, G. Adam, T. Gees, M. Schiess, W. Weigang, *Chem. Ber.* 1988, 121, 507).

Step F

An isocyanide of formula IX wherein $R_1$, $R_2$, $R_3$, $R_4$, $R_5$, $R_6$, $R_7$ and $R_8$ are as defined for formula I is reacted in a Scheme 2:
Preparation of compounds of subformula Ia:

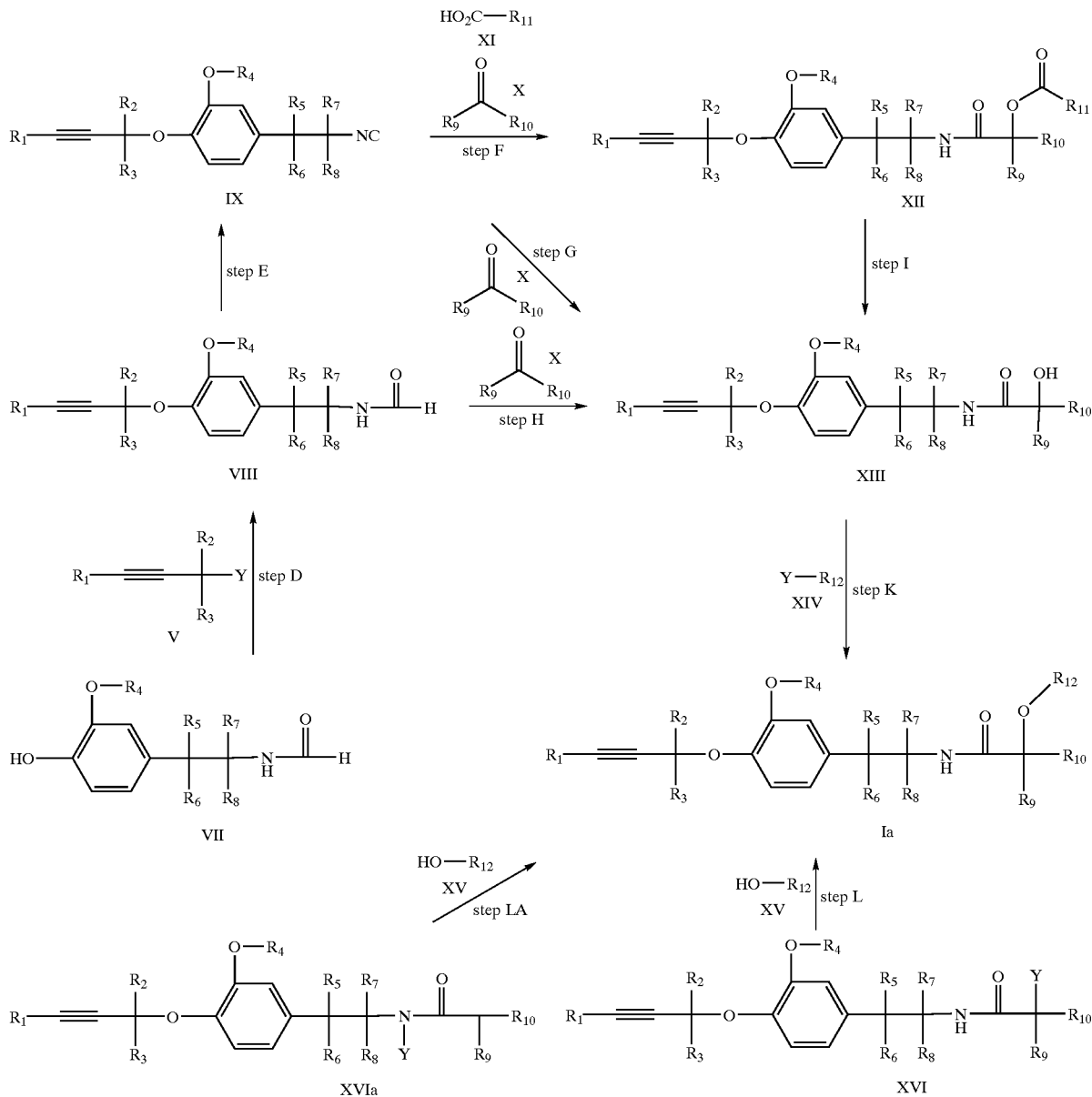

three-component Passerini reaction (J. March, *Advanced Organic Chemistry*, 4th ed., Wiley, 1992, p. 980) with an aldehyde or ketone of formula X, wherein $R_9$ and $R_{10}$ are as defined for formula I in the presence of a carboxylic acid XI wherein $R_{11}$ is hydrogen or lower alkyl, typically acetic acid, to give a O-acyl-α-hydroxy amide of formula XII, wherein $R_1$, $R_2$, $R_3$, $R_4$, $R_5$, $R_6$, $R_7$, $R_8$, $R_9$ and $R_{10}$ are as defined for formula I.

Step G

Alternatively to step F, an isocyanide of formula IX wherein $R_1$, $R_2$, $R_3$, $R_4$, $R_5$, $R_6$, $R_7$ and $R_8$ are as defined for formula I is reacted with an aldehyde or ketone of formula X in the presence of titanium tetrachloride to give an α-hydroxy amide of the formula XIII (where $R_1$, $R_2$, $R_3$, $R_4$, $R_5$, $R_6$, $R_7$, $R_8$, $R_9$ and $R_{10}$ have the same meaning as defined above) under conditions known per se (D. Seebach, G. Adam, T. Gees, M. Schiess, W. Weigang, *Chem. Ber.* 1988, 121, 507; O. Ort, U. Döller, W. Reissel, S. D. Lindell, T. L. Hough, D. J. Simpson, J. P. Chung, *Pesticide Sci.* 1997, 50, 331).

Step H

Alternatively to step F and step G, a compound of formula VIII, wherein $R_1$, $R_2$, $R_3$, $R_4$, $R_5$, $R_6$, $R_7$ and $R_8$ are as defined for formula I is treated with one phosgene equivalent (e.g. triphosgene) and a base (e.g. triethylamine) and in a second step, without isolation of the isocyanide intermediate, is further treated with titanium tetrachloride and an aldehyde or ketone of formula X, wherein $R_9$ and $R_{10}$ as defined for formula I under conditions known per se (WO 96/17840) to give an α-hydroxy amide of the formula XIII, wherein $R_1$, $R_2$, $R_3$, $R_4$, $R_5$, $R_6$, $R_7$, $R_8$, $R_9$ and $R_{10}$ are as defined for formula I.

Step I

An O-acyl-α-hydroxy amide of formula XII wherein $R_1$, $R_2$, $R_3$, $R_4$, $R_5$, $R_6$, $R_7$, $R_8$, $R_9$, $R_{10}$ and $R_{11}$ are as defined above is hydrolyzed to a an α-hydroxy amide of formula XIII, wherein $R_1$, $R_2$, $R_3$, $R_4$, $R_5$, $R_6$, $R_7$, $R_8$, $R_9$ and $R_{10}$ are as defined for formula I under classical conditions (J. March, *Advanced Organic Chemistry*, 4th ed., Wiley, 1992).

Step K

An α-hydroxy amide of formula XII wherein $R_1$, $R_2$, $R_3$, $R_4$, $R_5$, $R_6$, $R_7$, $R_8$, $R_9$ and $R_{10}$ are as defined for formula I is reacted with a compound XIV wherein $R_{12}$ is alkyl, alkenyl or alkynyl and Y is a leaving group like a halide such as a chloride or bromide or a sulfonic ester such as a tosylate, mesylate or triflate to a compound of formula Ia wherein $R_1$, $R_2$, $R_3$, $R_4$, $R_5$, $R_6$, $R_7$, $R_8$, $R_9$ and $R_{10}$ are as defined for formula I and $R_{12}$ is alkyl, alkenyl or alkynyl under the same conditions as defined for step B in Scheme 1.

Step L

An α-substituted amide of formula XVI wherein $R_1$, $R_2$, $R_3$, $R_4$, $R_5$, $R_6$, $R_7$, $R_8$, $R_9$ and $R_{10}$ are as defined for formula I and Y is a leaving group like a halide such as a chloride or bromide or a sulfonic ester such as a tosylate, mesylate or triflate, is reacted with a compound XV wherein $R_{12}$ is alkyl, alkenyl or alkynyl to a compound of formula Ia wherein $R_1$, $R_2$, $R_3$, $R_4$, $R_5$, $R_6$, $R_7$, $R_8$, $R_9$ and $R_{10}$ are as defined for formula I and $R_{12}$ is alkyl, alkenyl or alkynyl under the same conditions as defined for step B in Scheme 1.

Step LA

The compound of subformula Ia, wherein $R_1$, $R_2$, $R_3$, $R_4$, $R_5$, $R_6$, $R_7$, $R_8$, $R_9$ and $R_{10}$ are as defined for formula I and $R_{12}$ is alkyl, alkenyl or alkynyl may also be prepared by reacting a compound of formula XVIa wherein $R_1$, $R_2$, $R_3$, $R_4$, $R_5$, $R_6$, $R_7$, $R_8$, $R_9$ and $R_{10}$ are as defined for formula I and Y is a leaving group like a sulfonic ester such as a tosylate, mesylate or triflate with a compound of formula XV, wherein $R_{12}$ is alkyl, alkenyl or alkynyl under conditions known per se (R. V. Hoffmann, *J. Org. Chem.* 1995, 60, 7043). The reaction is performed optionally in the presence of an organic base like a tertiary amine, such as triethylamine, N,N-diisopropyl-ethylamine, pyridine, N-methyl-piperidine or N-methyl-morpholine at temperatures ranging from −80° C. to +200° C., preferentially at temperatures ranging from 0° C. to +120° C.

Scheme 3:
Preparation of intermediates of formula XIII:

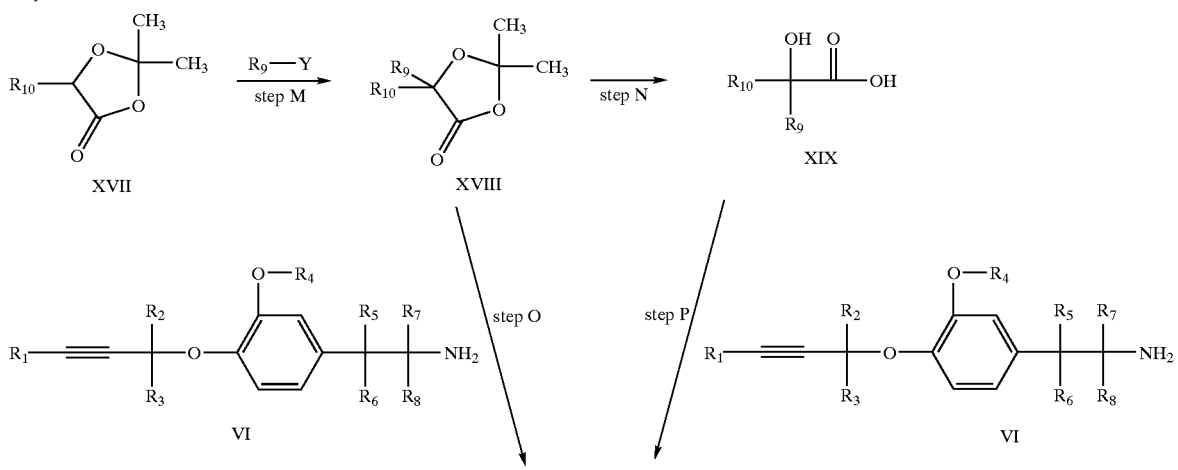

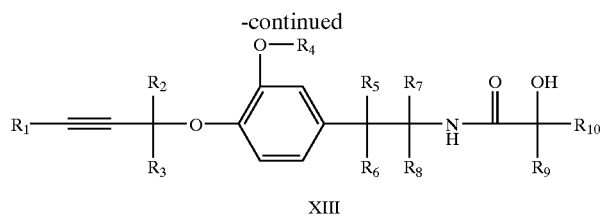

XIII

Step M

A dioxolanone XVII (obtained by the condensation of a mandelic acid with acetone under acid catalysis (see EP-A-071568) is subsequently treated with a base such as lithium diisopropylamide (LDA) and an alkylating agent $R_9$—Y wherein $R_9$ is alkyl and Y is a leaving group like a halide such as a chloride or bromide or a sulfonic ester such as a tosylate, mesylate or triflate, according to known procedures (F. Cavelier, S. Gomez, R. Jacquier, J. Verducci, *Tetrahedron Lett.* 1994, 2891, DE 4319887).

Steps N. O and P

The resulting dioxolanone XVIII is either heated with the appropriate amine VI at temperatures in between 50–200° C. (step O), or the dioxolanone is first hydrolysed in aqueous diluted mineral acid (e.g. HCl) or under basic conditions (aqueous sodium hydroxide (0–120° C.; step N) to the substituted hydroxy acid XIX which then can be amidated (step P, according to step A, scheme 1). Hydroxy acids XIX can also be obtained by reaction of a Grignard reagent $R_{10}$—MgHal (starting from an aryl-halide and Mg) with an appropriate α-keto acid ester (A. F. Hegarty, P. O'Neill, *Synthesis* 1993, 606).

Scheme 4:
Preparation of compound of subformula Ib:

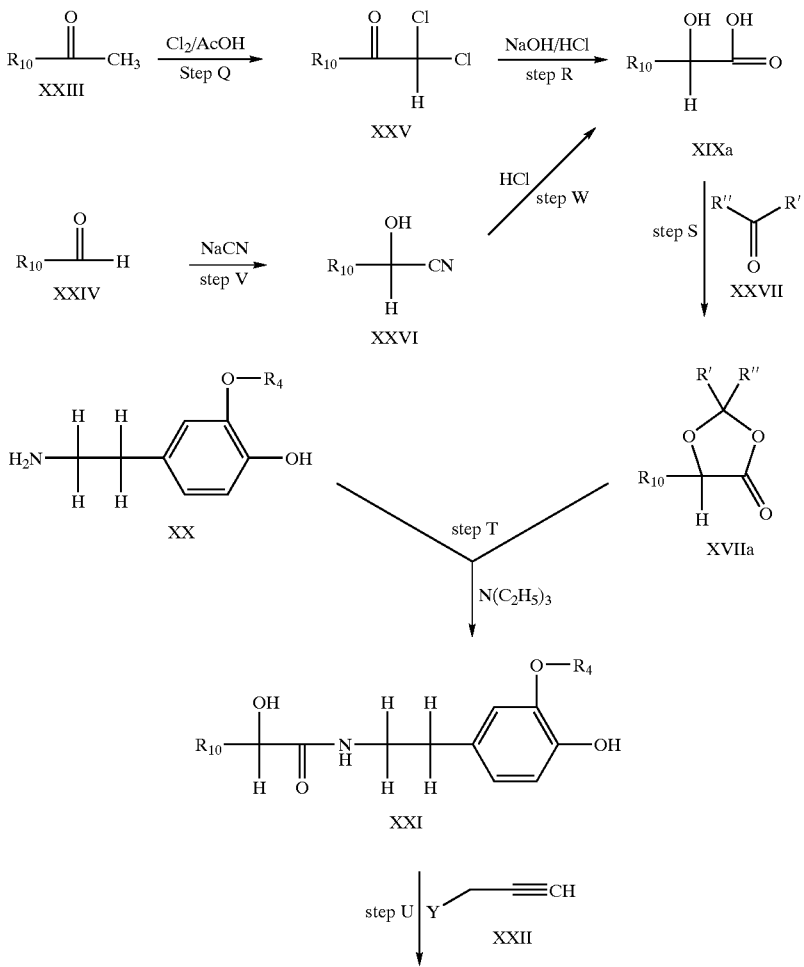

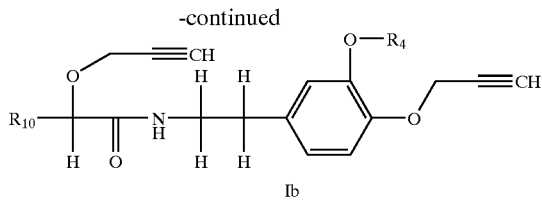
Ib wherein $R_4$ and $R_{10}$ are as defined for formula I, and R' and R" independently of each other are lower alkyl such as methyl, ethyl, propyl, isopropyl, butyl or isobutyl.

Step Q

A ketone of formula XXIII, wherein $R_{10}$ is as defined for formula I, is chlorinated to give a dichloroketone of formula XXV, wherein $R_{10}$ is as defined for formula I, under conditions known per se (J. G. Aston, J. D. Newkirk, D. M. Jenkins, J. Dorsky, *Org. Synth. Coll. Vol.* 3, 1955, 538).

Step R

A dichloroketone of formula XXV, wherein $R_{10}$ is as defined for formula I, is reacted with an inorganic base such as sodium hydroxide or potassium hydroxide to give a α-hydroxy acid of formula XIXa, wherein $R_{10}$ is as defined for formula I, under conditions known per se (J. G. Aston, J. D. Newkirk, D. M. Jenkins, J. Dorsky, *Org. Synth. Coll. Vol.* 3, 1955, 538).

Step S

A α-hydroxy acid of formula XIXa, wherein $R_{10}$ is as defined for formula I is reacted with a mineral acid such as sulfuric acid, hydrochloric acid or nitric acid and a ketone of formula XXVII, wherein R' and R" are alkyl to give a dioxolanone XVIIa, wherein $R_{10}$ is as defined for formula I and R' and R" are alkyl.

Step T

A dioxolanone of formula XVIIa, wherein $R_{10}$ is as defined for formula I and R' and R" are alkyl is reacted with an amine of formula XX, wherein $R_4$ is as defined for formula I in the presence of a base, such as triethylamine, N,N-diisopropyl-ethylamine, pyridine, N-methyl-piperidine, N-methyl-morpholine, potassium carbonate or sodium carbonate at temperatures ranging from −80° C. to +200° C., preferentially at temperatures ranging from 0° C. to 120° C. to give a compound of formula XXI, wherein $R_4$ and $R_{10}$ are as defined for formula I.

Step U

A compound of formula XXI, wherein $R_4$ and $R_{10}$ are as defined for formula I, is reacted with a compound of formula XXII, wherein Y is a leaving group like a halide such as chlorine or bromine or a sulfonic ester group such as a tosylate, mesylate or triflate, under phase-transfer alkylation conditions in the presence of an inorganic base such as sodium hydroxide or potassium hydroxide and a phase-transfer catalyst like benzyltriethylammonium chloride or tetrabutylammonium bromide to obtain a compound of formula Ib, wherein $R_4$ and $R_{10}$ are as defined for formula I.

Step V

An aldehyde of formula XXIV, wherein $R_{10}$ is as defined for formula I, is reacted with an inorganic cyanide, like sodium cyanide or potassium cyanide, in the presence of an inorganic sulfite, such as sodium bisulfite or potassium bisulfite to obtain a cyanohydrin of formula XXVI, wherein $R_{10}$ is as defined for formula I, under conditions known per se (B. B. Corson, R. A. Dodge, S. A. Harris, J. S. Yeaw, *Org. Synth. Coll. Vol.* 1, 1941, 336).

Step W

A cyanohydrin of formula XXVI, wherein $R_{10}$ is as defined for formula I, is reacted with a mineral acid, such as sulfuric acid, hydrochloric acid or nitric acid to yield a α-hydroxy acid of formula XIXa, wherein $R_{10}$ is as defined for formula I, under conditions known per se (B. B. Corson, R. A. Dodge, S. A. Harris, J. S. Yeaw, *Org. Synth. Coll. Vol.* 1, 1941, 336).

The compounds of formula I are oils or solids at room temperature and are distinguished by valuable microbiocidal properties. They can be used in the agricultural sector or related fields preventatively and curatively in the control of plant-destructive microorganisms. The compounds of formula I according to the invention are distinguished at low rates of concentration not only by outstanding microbiocidal, especially fungicidal, activity but also by being especially well tolerated by plants.

Surprisingly, it has now been found that the compounds of formula I have for practical purposes a very advantageous microbiocidal spectrum in the control of phytopathogenic microorganisms, especially fungi. They possess very advantageous curative and preventive properties and are used in the protection of numerous crop plants. With the compounds of formula I it is possible to inhibit or destroy phytopathogenic microorganisms that occur on various crops of useful plants or on parts of such plants (fruit, blossom, leaves, stems, tubers, roots), while parts of the plants which grow later also remain protected, for example, against phytopathogenic fungi.

The novel compounds of formula I prove to be effective against specific genera of the fungus class Fungi imperfecti (e.g. Cercospora), Basidiomycetes (e.g. Puccinia) and Ascomycetes (e.g. Erysiphe and Venturia) and especially against Oomycetes (e.g. Plasmopara, Peronospora, Pythium and Phytophthora). They therefore represent in plant protection a valuable addition to the compositions for controlling phytopathogenic fungi. The compounds of formula I can also be used as dressings for protecting seed (fruit, tubers, grains) and plant cuttings from fungal infections and against phytopathogenic fungi that occur in the soil.

The invention relates also to compositions comprising compounds of formula I as active ingredient, especially plant-protecting compositions, and to the use thereof in the agricultural sector or related fields.

In addition, the present invention includes the preparation of those compositions, wherein the active ingredient is homogeneously mixed with one or more of the substances or groups of substances described herein. Also included is a method of treating plants which is distinguished by the application of the novel compounds of formula I or of the novel compositions.

Target crops to be protected within the scope of this invention comprise, for example, the following species of plants: cereals (wheat, barley, rye, oats, rice, maize, sorghum and related species); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucurbitaceae (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) and plants such as tobacco, nuts, coffee, sugar cane, tea, pepper, vines, hops, bananas and natural rubber plants, and also ornamentals.

The compounds of formula I are normally used in the form of compositions and can be applied to the area or plant to be treated simultaneously or in succession with other active ingredients. Those other active ingredients may be fertilisers, micronutrient donors or other preparations that influence plant growth. It is also possible to use selective herbicides or insecticides, fungicides, bactericides, nematicides, molluscicides or mixtures of several of those preparations, if desired together with further carriers, surfactants or other application-promoting adjuvants customarily employed in formulation technology.

The compounds of formula I can be mixed with other fungicides, resulting in some cases in unexpected synergistic activities. Such mixtures are not limited to two active ingredients (one of formula I and one of the list of other fungicides), but to the contrary many comprise more than one active ingredient of the component of formula I and more than one other fungicide. Mixing components which are particularly suited for this purpose include e.g. azoles such as azaconazole, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, simeconazole, tebuconazole, tetraconazole, triadimefon, triadimenol, triflumizole, triticonazole; pyrimidinyl carbinoles, such as ancymidol, fenarimol, nuarimol; 2-amino-pyrimidines, such as bupirimate, dimethirimol, ethirimol; morpholines, such as dodemorph, fenpropidine, fenpropimbrph, spiroxamin, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozoline; carboxamides, such as carboxin, fenfuram, flutolanil, mepronil, oxycarboxin, thifluzamide; guanidines, such as guazatine, dodine, iminoctadine; strobilurines, such as azoxystrobin, kresoxim-methyl, metominostrobin, SSF-129, trifloxystrobin, picoxystrobin, BAS 500F (proposed name pyraclostrobin); dithiocarbamates, such as ferbam, mancozeb, maneb, metiram, propineb, thiram, zineb, ziram; N-halomethylthiotetrahydrophthalimides, such as captafol, captan, dichlofluanid, fluoromides, folpet, tolyfluanid; Cu-compounds, such as Bordeaux mixture, copper hydroxide, copper oxychloride, copper sulfate, cuprous oxide, mancopper, oxine-copper; nitrophenol-derivatives, such as dinocap, nitrothal-isopropyl; organo-p-derivatives, such as edifenphos, iprobenphos, isoprothiolane, phosdiphen, pyrazophos, tolclofos-methyl; various others, such as acibenzolar-S-methyl, anilazine, blasticidin-S, chinomethionate, chloroneb, chlorothalonil, cymoxanil, dichlone, diclomezine, dicloran, diethofencarb, dimethomorph, SYP-LI90 (proposed name: flumorph), dithianon, etridiazole, famoxadone, fenamidone, fentin, ferimzone, fluazinam, flusulfamide, fenhexamid, fosetyl-aluminium, hymexazol, iprovalicarb, IKF-916, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin, zoxamide (RH7281).

Some particularly interesting mixtures in view of technical value in the agricultural practice (comprising at least the one mentioned compound of formula I together with the above mentioned mentioned other fungicide, but not being limited thereto, i.e. such mixtures may comprise additional components according to needs when controlling certain fungi on certain crop plants), having enhanced synergistic levels of fungicidal activity, or being especially well suited for the control of persistent or very damaging phytopathogenic fungi are among the following:

1) 2-phenyl-N-[2-(3-methoxy-4-prop-2-ynyloxy-phenyl)-ethyl]-2-prop-2-ynyloxy-acetamide (compound E1.002), combined with any one active ingredient selected from cymoxanil, trifloxystrobin, azoxystrobin, picoxystrobin, chlorothalonil, metalaxyl, metalaxyl-M, pyraclostrobin (BAS500F), dimethomorph, fosetyl-Al, copper-salts, acibenzolar-S-methyl, fludioxonil, mancozeb, folpet, fluazinam, iprovalicarb, zoxamid and (S)-2-(methylsulfonyl-amino)-3-methyl-butyric acid N-[2-{3-methoxy-4-(3-(4-chlorophenyl)-2-propyn-1-yloxy)-phenyl}-ethyl]-amide; and
2) 2-(4-chloro-phenyl)-N-[2-(3-methoxy-4-prop-2-ynyloxy-phenyl)-ethyl]-2-prop-2-ynyloxy-acetamide(compound E1.011), combined with any one active ingredient selected from cymoxanil, trifloxystrobin, azoxystrobin, picoxystrobin, chlorothalonil, metalaxyl, metalaxyl-M, pyraclostrobin (BAS500F), dimethomorph, fosetyl-Al, copper-salts, acibenzolar-S-methyl, fludioxonil, mancozeb, folpet, fluazinam, iprovalicarb, zoxamid and (S)-2-(methylsulfonyl-amino)-3-methyl-butyric acid N-[2-{3-methoxy-4-(3-(4-chlorophenyl)-2-propyn-1-yloxy)-phenyl}-ethyl]-amide, and
3) 2-(4-bromo-phenyl)-N-[2-(3-methoxy-4-prop-2-ynyloxy-phenyl)-ethyl]-2-prop-2-ynyloxy-acetamide (compound E1.022), combined with any one active ingredient selected from cymoxanil, trifloxystrobin, azoxystrobin, picoxystrobin, chlorothalonil, metalaxyl, metalaxyl-M, pyraclostrobin (BAS500F), dimethomorph, fosetyl-Al, copper-salts, acibenzolar-S-methyl, fludioxonil, mancozeb, folpet, fluazinam, iprovalicarb, zoxamid and (S)-2-(methylsulfonyl-amino)-3-methyl-butyric acid N-[2-{3-methoxy-4-(3-(4-chlorophenyl)-2-propyn-1-yloxy)-phenyl}-ethyl]-amide, and
4) 2-(4-fluoro-phenyl)-N-[2-(3-methoxy-4-prop-2-ynyloxy-phenyl)-ethyl]-2-prop-2-ynyloxy-acetamide (compound E1.033), combined with any one active ingredient selected from cymoxanil, trifloxystrobin, azoxystrobin, picoxystrobin, chlorothalonil, metalaxyl, metalaxyl-M, pyraclostrobin (BAS500F), dimethomorph, fosetyl-Al, copper-salts, acibenzolar-S-methyl, fludioxonil, mancozeb, folpet, fluazinam, iprovalicarb, zoxamid and (S)-2-(methylsulfonyl-amino)-3-methyl-butyric acid N-[2-{3-methoxy-4-(3-(4-chlorophenyl)-2-propyn-1-yloxy)-phenyl}-ethyl]-amide, and
5) 2-(4-tolyl)-N-[2-(3-methoxy-4-prop-2-ynyloxy-phenyl)-ethyl]-2-prop-2-ynyloxy-acetamide (compound E1.045), combined with any one active ingredient selected from cymoxanil, trifloxystrobin, azoxystrobin, picoxystrobin, chlorothalonil, metalaxyl, metalaxyl-M, pyraclostrobin (BAS500F), dimethomorph, fosetyl-Al, copper-salts, acibenzolar-S-methyl, fludioxonil, mancozeb, folpet, fluazinam, iprovalicarb, zoxamid and (S)-2-(methylsulfonyl-amino)-3-methyl-butyric acid N-[2-{3-methoxy-4-(3-(4-chlorophenyl)-2-propyn-1-yloxy)-phenyl}-ethyl]-amide, and 6) 2-(4-ethyl-phenyl)-N-[2-(3-methoxy-4-prop-2-ynyloxy-phenyl)-ethyl]-2-prop-2-ynyloxy-acetamide (compound E1.053), combined with any one active ingredient selected from cymoxanil, trifloxystrobin, azoxystrobin, picoxystrobin, chlorothalonil, metalaxyl, metalaxyl-M, pyraclostrobin (BAS500F), dimethomorph, fosetyl-Al, copper-salts, acibenzolar-S-methyl, fludioxonil, mancozeb, folpet, fluazinam, iprovalicarb, zoxamid and (S)-2-(methylsulfonyl-amino)-3-methyl-butyric acid N-[2-{3-methoxy-4-(3-(4-chlorophenyl)-2-propyn-1-yloxy)-phenyl}-ethyl]-amide, and 7) 2-(3,4-difluoro-phenyl)-N-[2-(3-methoxy-4-prop-2-ynyloxy-phenyl)-ethyl]-2-prop-2-ynyloxy-acetamide (compound E1.085), combined with any one active ingredient selected from cymoxanil, trifloxystrobin, azoxystrobin, picoxystrobin, chlorothalonil, metalaxyl, metalaxyl-M, pyraclostrobin (BAS500F), dimethomorph, fosetyl-Al, copper-salts, acibenzolar-S-methyl, fludioxonil, mancozeb, folpet, fluazinam, iprovalicarb, zoxamid and (S)-2-(methylsulfonyl-amino)-3-methyl-butyric acid N-[2-{3-methoxy-4-(3-(4-chlorophenyl)-2-propyn-1-yloxy)-phenyl}-ethyl]-amide, and 8) 2-(3-fluoro-4-chloro-phenyl)-N-[2-(3-methoxy-4-prop-2-ynyloxy-phenyl)-ethyl]-2-prop-2-ynyloxy-acetamide (compound E1.091), combined with any one active ingredient selected from cymoxanil, trifloxystrobin, azoxystrobin, picoxystrobin, chlorothalonil, metalaxyl, metalaxyl-M, pyraclostrobin (BAS500F), dimethomorph, fosetyl-Al, copper-salts, acibenzolar-S-methyl, fludioxonil, mancozeb, folpet, fluazinam, iprovalicarb, zoxamid and (S)-2-(methylsulfonyl-amino)-3-methyl-butyric acid N-[2-{3-methoxy-4-(3-(4-chlorophenyl)-2-propyn-1-yloxy)-phenyl}-ethyl]-amide, and 9) 2-(3,4-dichloro-phenyl)-N-[2-(3-methoxy-4-prop-2-ynyloxy-phenyl)-ethyl]-2-prop-2-ynyloxy-acetamide (compound E1.102), combined with any one active ingredient selected from cymoxanil, trifloxystrobin, azoxystrobin, picoxystrobin, chlorothalonil, metalaxyl, metalaxyl-M, pyraclostrobin (BAS500F), dimethomorph, fosetyl-Al, copper-salts, acibenzolar-S-methyl, fludioxonil, mancozeb, folpet, fluazinam, iprovalicarb, zoxamid and (S)-2-(methylsulfonyl-amino)-3-methyl-butyric acid N-[2-{3-methoxy-4-(3-(4-chlorophenyl)-2-propyn-1-yloxy)-phenyl}-ethyl]-amide.

In the above mentioned mixtures, the mixture ratio of the active ingredients is so selected that it reaches optional control of the phytopathogenic microorganism on the host plants. This ratio is in general between 100:1 and 1:100, more preferably between 10:1 and 1:10 of a compound of formula I vis-à-vis the second fungicide. The mixtures may not only comprise one of the listed combinational active ingredients, but may comprise more than one additional active ingredients selected from that specified group, thus forming for example 3-way- or even 4-way-mixtures.

Suitable carriers and surfactants may be solid or liquid and correspond to the substances ordinarily employed in formulation technology, such as e.g. natural or regenerated mineral substances, solvents, dispersants, wetting agents, tackifiers, thickeners, binders or fertilisers. Such carriers and additives are described, for example, in WO 95/30651.

A preferred method of applying a compound of formula I, or an agrochemical composition comprising at least one of those compounds, is application to the foliage (foliar application), the frequency and the rate of application depending upon the risk of infestation by the pathogen in question. The compounds of formula I may also be applied to seed grains (coating) either by impregnating the grains with a liquid formulation of the active ingredient or by coating them with a solid formulation.

The compounds of formula I are used in unmodified form or, preferably, together with the adjuvants conventionally employed in formulation technology, and are for that purpose advantageously formulated in known manner e.g. into emulsifiable concentrates, coatable pastes, directly sprayable or dilutable solutions, dilute emulsions, wettable powders, soluble powders, dusts, granules, and by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 1 g to 2 kg of active ingredient (a.i.) per hectare (ha), preferably from 10 g to 1 kg a.i./ha, especially from 25 g to 750 g a.i./ha. When used as seed dressings, rates of from 0.001 g to 1.0 g of active ingredient per kg of seed are advantageously used.

The formulations, i.e. the compositions, preparations or mixtures comprising the compound(s) (active ingredient(s)) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Further surfactants customarily used in formulation technology will be known to the person skilled in the art or can be found in the relevant technical literature.

The agrochemical compositions usually comprise 0.01 to 99% by weight, preferably 0.1 to 95% by weight, of a compound of formula I, 99.99 to 1% by weight, preferably 99.9 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further ingredients, such as stabilisers, antifoams, viscosity regulators, binders and tackifiers, as well as fertilisers or other active ingredients for obtaining special effects.

The Examples which follow illustrate the invention described above, without limiting the scope thereof in any way. Temperatures are given in degrees Celsius. Ph stands for phenyl.

PREPARATION EXAMPLES

Example E1

2-(4-Chloro-phenyl)-2-methoxy-N-[2-(3-methoxy-4-prop-2-ynyloxy-phenyl)-ethyl]-acetamide

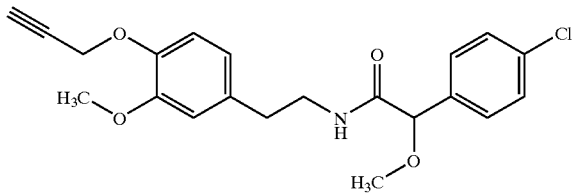

a) N-[2-(4-Hydroxy-3-methoxy-phenyl)-ethyl]-formamide

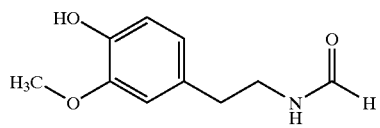

Formic acid (230 g, 5.0 mol) is added dropwise to acetic anhydride (383 g, 3.75 mol) at 0° C. This mixture is stirred for 2 hours at +55° C. and subsequently cooled again to 0° C. Tetrahydrofuran (500 ml) is added at this temperature followed by 4-(2-amino-ethyl)-2-methoxy-phenol hydrochloride (50 g, 0.25 mol). The resulting white suspension is stirred for 18 hours at +75° C., changing into a yellow solution. The reaction mixture is evaporated and the residue is submitted to flash-chromatography to yield N-[2-(4-hydroxy-3-methoxy-phenyl)-ethyl]-formamide. $^1$H-NMR (300 MHz, CDCl$_3$): 2.85(t, 2H, CH$_2$CH$_2$), 3.57(t, 2H, CH$_2$CH$_2$), 3.82(s, 3H, OCH$_3$), 5.69(bs, 1H, NH), 6.67–7.09 (m, 3H, CH arom.), 8.12(s, 1H, CHO).

b) N-[2-(3-Methoxy-4-prop-2-ynyloxy-phenyl)-ethyl]-formamide

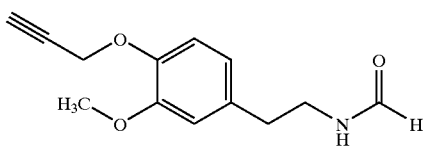

Sodium methoxide (32 ml of a 5.4 M solution in methanol, 0.17 mol) is added to a solution of N-[2-(4-hydroxy-3-methoxy-phenyl)-ethyl]-formamide (32 g, 0.16 mol) in methanol (400 ml). Propargyl bromide (20 g, 0.17 mol) is added and the mixture is refluxed for 4 hours. After evaporation the residue is taken up in ethyl acetate (400 ml) and washed with water (2×200 ml). The organic layer is dried over magnesium sulfate and evaporated. The residue is submitted to flash-chromatography to give the N-[2-(3-methoxy-4-prop-2-ynyloxy-phenyl)-ethyl]-formamide. $^1$H-NMR (300 MHz, CDCl$_3$): 2.44 (t, 1H, C≡CH), 2.73 (t, 2H, CH$_2$CH$_2$), 3.51 (t, 2H, CH$_2$CH$_2$), 3.82 (s, 3H, OCH$_3$), 4.69 (m, 2H, OCH$_2$), 5.53 (bs, 1H, NH), 6.62–6.95 (m, 3H, CH arom.), 8.09 (s, 1H, CHO).

c) 2-(4-Chloro-phenyl)-2-hydroxy-N-[2-(3-methoxy-4-prop-2-ynyloxy-phenyl)-ethyl]-acetamide

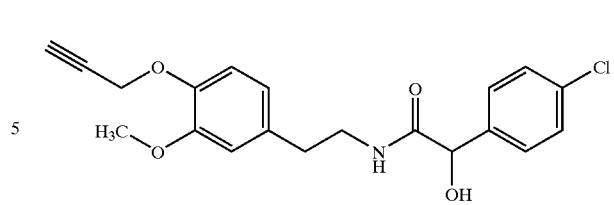

N-[2-(3-methoxy-4-prop-2-ynyloxy-phenyl)-ethyl]-formamide (34 g, 0.14 mol) and triethylamine (34 g, 0.34 mol) are dissolved in dichloromethane (120 ml). Bis(trichloromethyl)carbonate (triphosgene, 16 g, 55 mmol) in dichloromethane (80 ml) is added at +5° C. The mixture is stirred for 4 hours at +5° C. and then cooled to −78° C. A solution of titanium tetrachloride (28 g, 0.15 mol) in dichloromethane (150 ml) is added and the mixture is stirred for 2 hours at −40° C. 4-Chlorobenzaldehyde (20 g, 0.14 mol) in dichloromethane (70 ml) is added dropwise and the mixture is stirred for 17 h at room temperature. The mixture is hydrolyzed with 5N HCl (80 ml), stirred 30 minutes at room temperature and washed with water. After evaporation of the organic layer the residue is submitted to flash-chromatography (ethyl acetate/hexane) to give 2-(4-chloro-phenyl)-2-hydroxy-N-[2-(3-methoxy-4-prop-2-ynyloxy-phenyl)-ethyl]-acetamide. $^1$H-NMR (300 MHz, CDCl$_3$): 2.54 (t, 1H, C≡CH), 2.72 (t, 2H, CH$_2$CH$_2$), 3.53 (t, 2H, CH$_2$CH$_2$), 3.84 (s, 3H, OCH$_3$), 4.78 (m, 2H, OCH$_2$), 4.98 (s, 1H, CHOH), 6.07 (bs, 1H, NH), 6.53–7.38 (m, 7H, CH arom.).

d)

2-(4-Chloro-phenyl)-2-hydroxy-N-[2-(3-methoxy-4-prop-2-ynyloxy-phenyl)-ethyl]-acetamide (2.6 g, 7.0 mmol) is dissolved in N,N-dimethylformamide (30 ml). Sodium hydride (0.18 g, 7.5 mmol) is added in portions at +5° C. The mixture is stirred for 30 minutes at room temperature. Subsequently iodomethane (1.1 g, 7.5 mmol) is added dropwise and the resulting mixture is stirred for further 3 hours at room temperature. The reaction mixture is poured on ice/water (200 ml) and extracted with ethyl acetate (2×200 ml). The combined organic layer is washed with brine (200 ml) and dried over magnesium sulfate. After evaporation of the solvent, the residue is purified by chromatography (ethyl acetate/hexane) to yield 2-(4-chloro-phenyl)-2-methoxy-N-[2-(3-methoxy-4-prop-2-ynyloxy-phenyl)-ethyl]-acetamide. $^1$H-NMR (300 MHz, CDCl$_3$): 2.53 (t, 1H, C≡CH), 2.80 (t, 2H, CH$_2$CH$_2$), 3.34 (s, 3H, OCH$_3$), 3.55 (t, 2H, CH$_2$CH$_2$), 3.84 (s, 3H, OCH$_3$), 4.58 (s, 1H, CHOH), 4.79 (m, 2H, OCH$_2$), 6.68–7.34 (m, 8H, CH arom., NH).

Example E2

2-(4-Bromo-phenyl)-N-[2-(3-methoxy-4-prop-2-ynyloxy-phenyl)-ethyl]-2-prop-2-ynyloxy-acetamide

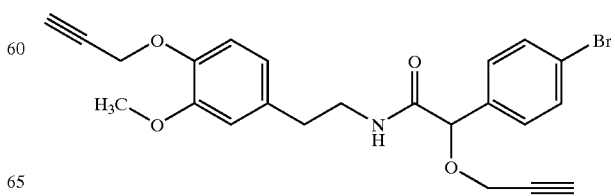

a) 1-(4-Bromo-phenyl)-2,2-dichloro-ethanone

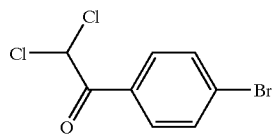

4-Bromoacetophenone (100 g, 0.5 mol) is dissolved in 300 ml of glacial acetic acid. Chlorine gas is admitted at a rate that allows to control the reaction temperature not to exceed +60° C. The chlorination is continued until an excess of the halogen has been absorbed, indicated by the development of a yellow color. The reaction mixture is poured on ice and extracted with ethyl acetate. The organic phase is separated and the aqueous layer is extracted twice with ethyl acetate. The combined organic phases are washed with brine, dried over sodium sulfate and evaporated. 1-(4-Bromo-phenyl)-2,2-dichloro-ethanone is obtained as residue sufficiently pure to be used in the next step. $^1$H-NMR (300 MHz, CDCl$_3$): 6.50 (s, 1H, CHCl$_2$), 7.60 (d, 2H, CH arom.), 7.92 (d, 2H, CH arom.).

b) (4-Bromo-phenyl)-hydroxy-acetic acid

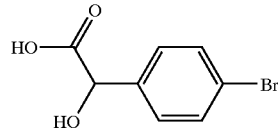

Sodium hydroxide (72 g, 1.8 mol) is dissolved in 650 ml of water. The solution is heated to +60° C. and 1-(4-bromo-phenyl)-2,2-dichloro-ethanone (130 g, 0.48 mol) is added dropwise in order to control the reaction temperature not to exceed +65° C. After the addition is complete, stirring is continued for 1 hour at +60° C. The reaction mixture is then cooled to +15° C. and 95 ml of 10 N hydrochloric acid are added. Subsequently diethyl ether is added and the mixture is stirred vigorously for 30 minutes. The organic phase is separated and the aqueous layer is extracted twice with diethyl ether. The combined organic phases are washed with brine, dried over sodium sulfate and evaporated to yield (4-bromo-phenyl)-hydroxy-acetic acid. $^1$H-NMR (300 MHz, CDCl$_3$): 4.95 (s, 1H, CHOH), 7.30 (d, 2H, CH arom.), 7.48 (d, 2H, CH arom.).

c) 5-(4-Bromo-phenyl)-2,2-dimethyl-[1,3]dioxolan-4-one

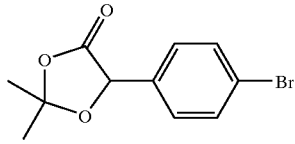

(4-Bromo-phenyl)-hydroxy-acetic acid (97 g, 0.42 mol) is dissolved in 200 ml of acetone and cooled to −10° C. At this temperature 23 ml of concentrated sulfuric acid are added dropwise. After the addition is complete, the reaction mixture is stirred at −10° C. for further 30 minutes and is subsequently poured into a cooled (0° C.) solution of sodium carbonate (86 g, mol) in 800 ml of water. The crystalline 5-(4-bromo-phenyl)-2,2-dimethyl-[1,3]dioxolan-4-one is filtered, washed with ice-cold water and dried in the high-vacuum. $^1$H-NMR (300 MHz, CDCl$_3$): 1.72 (s, 3H, CH$_3$), 1.76 (s, 3H, CH$_3$), 5.37 (s, 1H, CHO), 7.37 (d, 2H, CH arom.), 7.56 (d, 2H, CH arom.).

d) 2-(4-Bromo-phenyl)-2-hydroxy-N-[2-(4-hydroxy-3-methoxy-phenyl)-ethyl]-acetamide

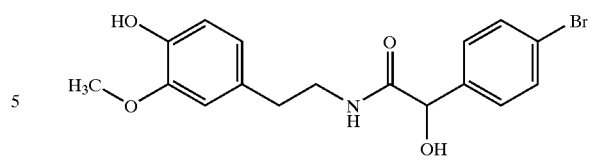

5-(4-Bromo-phenyl)-2,2-dimethyl-[1,3]dioxolan-4-one (15 g, 55 mmol) is dissolved in 50 ml of ethanol. 4-(2-Amino-ethyl)-2-methoxy-phenol hydrochloride (14 g, 69 mmol) and triethylamine (7.0 g, 69 mmol) are added and the mixture is stirred for 72 hours at room temperature. The solvent is removed in vacuum and the residue is extracted with ethyl acetate and 1N hydrochloric acid. The aqueous layer is extracted twice with ethyl acetate and the combined organic phases are washed with brine, dried over sodium sulfate and evaporated. The remaining 2-(4-bromo-phenyl)-2-hydroxy-N-[2-(4-hydroxy-3-methoxy-phenyl)-ethyl]-acetamide is purified by chromatography on silica gel. $^1$H-NMR (300 MHz, CDCl$_3$): 2.71 (t, 2H, CH$_2$CH$_2$), 3.54 (t, 2H, CH$_2$CH$_2$), 3.80 (s, 3H, OCH$_3$), 5.59 (s, 1H, CHOH), 6.16 (bs, 1H, NH), 6.52–7.35 (m, 7H, CH arom.).

e)

A 80% solution of propargyl bromide in toluene (10.5 g, 71 mmol) is added slowly at room temperature to a mixture of 2-(4-bromo-phenyl)-2-hydroxy-N-[2-(4-hydroxy-3-methoxy-phenyl)-ethyl]-acetamide (11 g, 29 mmol), 30% sodium hydroxide solution (14 ml, 0.14 mol) and catalytic amounts of tetrabutylammonium bromide in 40 ml of dichloromethane. The reaction mixture is stirred for 16 hours at +40° C. Subsequently the mixture is evaporated and the residue is diluted with water and dichloromethane. The organic phase is separated and the aqueous layer is extracted three times with dichloromethane. The combined organic phases are washed with brine, dried over sodium sulfate and evaporated. The remaining oil is purified by chromatography on silica gel (ethyl acetate/hexane 1:1) to yield 2-(4-bromo-phenyl)-N-[2-(3-methoxy-4-prop-2-ynyloxy-phenyl)-ethyl]-2-prop-2-ynyloxy-acetamide. $^1$H-NMR (300 MHz, CDCl$_3$): 2.51 (t, 1H, C≡CH), 2.54 (t, 1H, C≡CH), 2.81 (t, 2H, CH$_2$CH$_2$), 3.54 (t, 2H, CH$_2$CH$_2$), 3.86 (s, 3H, OCH$_3$), 3.97 (dd, 1H, OCH$_2$), 4.20 (dd, 1H, OCH$_2$), 4.78 (d, 2H, OCH$_2$), 4.96 (s, 1H, CHOH), 6.70–7.52 (m, 8H, CH arom., NH).

Example E3

2-(4-Chloro-phenyl)-N-[2-(3-methoxy-4-prop-2-ynyloxy-phenyl)-ethyl]-2-propoxy-acetamide

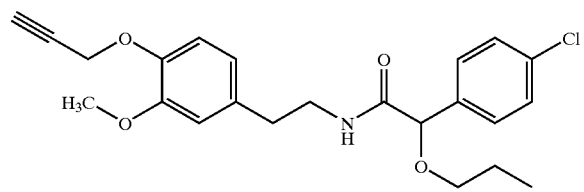

a) N-Benzoyloxy-2-(3-methoxy-4-prop-2-ynyloxy-phenyl)-ethylamine

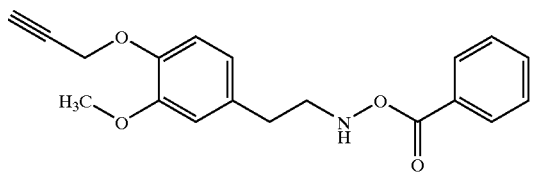

A solution of benzoyl peroxide (2.37 g, 9.8 mmol) in CH$_2$Cl$_2$ is added to a vigorously stirred solution of 2-(3-methoxy-4-prop-2-ynyloxy-phenyl)-ethylamine (2.0 g, 9.8 mmol) in 49 ml of a carbonate buffer solution (pH=10.5). The reaction mixture is stirred at room temperature for 6 h. The water layer is extracted twice with CH$_2$Cl$_2$, the organic layers are combined and dried over Na$_2$SO$_4$. After evaporation of the solvent the product is purified by flash chromatography (ethyl acetate:hexane, 1:2) to yield N-benzoyloxy-2-(3-methoxy-4-prop-2-ynyloxy-phenyl)-ethylamine as an oil.

b) N-Benzoyloxy-2-(4-chloro-phenyl)-N-[2-(3-methoxy-4-prop-2-ynyloxy-phenyl)-ethyl]-acetamide

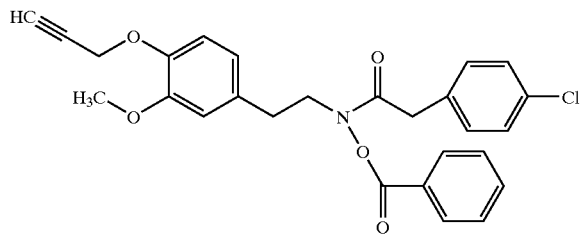

BOP (2.0 g, 4.5 mmol) is added to a solution of (4-chloro-phenyl)-acetic acid (0.7 g, 4.1 mmol), N-benzoyloxy-2-(3-methoxy-4-prop-2-ynyloxy-phenyl)-ethylamine (1.4 g, 4.3 mmol) and N-ethyldiisopropylamine (2.8 ml, 16.4 mmol) in 10 ml DMF. The reaction mixture is stirred at room temperature for 20 hours. The reaction mixture is then poured into water and extracted three times with ethyl acetate. The organic phase is dried over Na$_2$SO$_4$ and concentrated. The crude product is purified by flash chromatography (ethyl acetate:hexane, 1:3) to yield N-benzoyloxy-2-(4-chloro-phenyl)-N-[2-(3-methoxy-4-prop-2-ynyloxy-phenyl)-ethyl]-acetamide as an oil.

c) 2-(4-Chloro-phenyl)-N-hydroxy-N-[2-(3-methoxy-4-prop-2-ynyloxy-phenyl)-ethyl]-acetamide

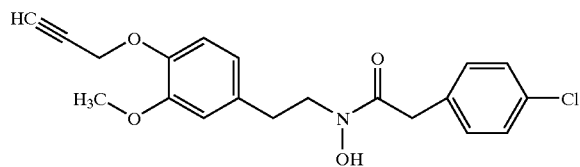

N-Benzoyloxy-2-(4-chloro-phenyl)-N-[2-(3-methoxy-4-prop-2-ynyloxy-phenyl)-ethyl]-acetamide (0.3 g, 0.6 mmol) is dissolved in 2 ml 10% NH$_4$OH/MeOH and stirred at room temperature overnight. The solvent is removed under vacuum and the crude product is purified by flash chromatography (ethyl acetate:hexane, 1:2) to yield 2-(4-chloro-phenyl)-N-hydroxy-N-[2-(3-methoxy-4-prop-2-ynyloxy-phenyl)-ethyl]-acetamide as a solid.

d) 2-(4-Chloro-phenyl)-N-mesyloxy-N-[2-(3-methoxy-4-prop-2-ynyloxy-phenyl)-ethyl]-acetamide

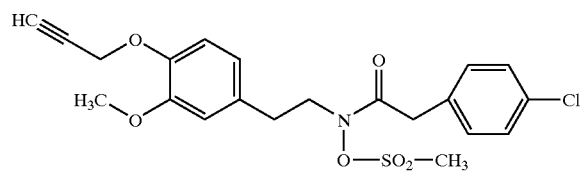

Methanesulfonyl chloride (0.022 ml, 0.286 mmol) is added dropwise to a solution of 2-(4-chloro-phenyl)-N-hydroxy-N-[2-(3-methoxy-4-prop-2-ynyloxy-phenyl)-ethyl]-acetamide (0.1 g, 0.26 mmol), and Et$_3$N (0.036 ml, 0.26 mmol) in 1 ml CH$_2$Cl$_2$ at 0° C. The reaction mixture is allowed to warm to room temperature and stirred for another 2 hours. The reaction mixture is then washed with water, 1N HCl, and brine and dried over Na$_2$SO$_4$. After rotary evaporation, the product is purified by flash chromatography (ethyl acetate:hexane, 1:2) to yield 2-(4-chloro-phenyl)-N-mesyloxy-N-[2-(3-methoxy-4-prop-2-ynyloxy-phenyl)-ethyl]-acetamide as a solid, mp. 91–93° C.

e)

To a solution of 2-(4-chloro-phenyl)-N-mesyloxy-N-[2-(3-methoxy-4-prop-2-ynyloxy-phenyl)-ethyl]-acetamide (452 mg, 1 mmol) in a mixture of 6 ml acetonitrile and 6 ml n-propanol during a period of 12 hours a solution of triethylamine (0.146 ml, 1.05 mmol) in 12 ml of acetonitrile is added dropwise. The mixture is stirred for 20 hours at room temperature. The solvent and excess n-propanol is removed under reduced pressure and the residue was diluted with ethyl acetate (30 ml), washed with water, 1N HCl, and brine, and dried with Na$_2$SO$_4$. After evaporation of the solvent the product is purified by flash chromatography (ethyl acetate:hexane, 1:2) to yield 2-(4-chloro-phenyl)-N-[2-(3-methoxy-4-prop-2-ynyloxy-phenyl)-ethyl]-2-propoxy-acetamide in form of an oil. $^1$H-NMR (300 MHz, CDCl$_3$): 0.89(t, 3H, CH$_3$), 1.58(q, 2H, CH$_2$), 2.50(t, 1H, C≡CH), 2.79(t, 2H, CH$_2$CH$_2$), 3.35(t, 2H, OCH$_2$), 3.52(dt, 2H, CH$_2$CH$_2$), 3.83(s, 3H, OCH$_3$), 4.63(s, 1H, CHOH), 4.74(d, 2H, OCH$_2$), 6.67–7.30(m, 8H, CH arom., NH).

According to the procedures of Examples E1, E2 and/or E3 the compounds listed in table E1 are obtained.

TABLE E1

(Ph designates phenyl)

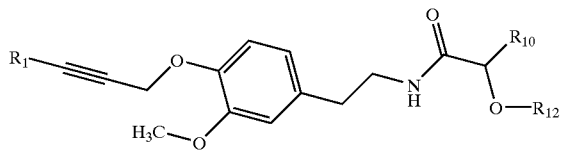

| No. | R₁ | R₁₀ | R₁₂ | ¹H-NMR (300 MHz, CDCl₃): δ = |
|---|---|---|---|---|
| E1.001 | H | Ph | CH₂CH₃ | 1.20(t, 3H), 2.52(t, 1H), 2.81(t, 2H), 3.42–3.59(m, 4H), 3.86(s, 3H), 4.70(s, 1H), 4.78(d, 2H), 6.69–7.39(m, 8H) |
| E1.002 | H | Ph | CH₂C≡CH | 2.24(t, 1H), 2.29(t, 1H), 2.58(t, 2H), 3.32(t, 2H), 3.60(s, 3H), 3.73(dd, 1H), 3.95(dd, 1H), 4.53(d, 2H), 4.76(s, 1H), 6.46–7.11(m, 8H) |
| E1.003 | H | 4-Cl—Ph | CH₃ | 2.53(t, 1H), 2.80(t, 2H), 3.34(s, 3H), 3.55(t, 2H), 3.84(s, 3H), 4.58(s, 1H), 4.79(d, 2H), 6.68–7.34(m, 7H) |
| E1.004 | H | 4-Cl—Ph | CH₂CH₃ | 1.20(t, 3H), 2.52(t, 1H), 2.79(t, 2H), 3.41–3.57(m, 4H), 3.84(s, 3H), 4.68(s, 1H), 4.77(d, 2H), 6.68–7.32(m, 7H) |
| E1.005 | H | 4-Cl—Ph | CH₂CF₃ | 2.50(t, 1H), 2.79(t, 2H), 3.56(t, 2H), 3.69–3.85(m, 5H), 4.77(d, 2H), 4.82(s, 1H), 6.65–7.38(m, 7H) |
| E1.006 | H | 4-Cl—Ph | n-C₃H₇ | 0.89(t, 3H), 1.58(q, 2H), 2.50(t, 1H), 2.79(t, 2H), 3.35(t, 2H), 3.52(dt, 2H), 3.83(s, 3H), 4.63(s, 1H), 4.74(d, 2H), 6.67–7.30(m, 7H) |
| E1.007 | H | 4-Cl—Ph | i-C₃H₇ | 1.12(s, 3H), 1.14(s, 3H), 2.49(t, 1H), 2.78(t, 2H), 3.48–3.60(m, 3H), 3.85(s, 3H), 4.72–4.78(m, 3H), 6.68–7.31(m, 7H) |
| E1.008 | H | 4-Cl—Ph | CH₂-cycl-C₃H₅ | 0.05(d, 2H), 0.41(d, 2H), 0.89(m, 1H), 2.39(t, 1H), 2.65(t, 3H), 3.14(d, 2H), 3.42(t, 2H), 3.72(s, 3H), 4.59–4.66(m, 3H), 6.54–7.23(m, 7H) |
| E1.009 | H | 4-Cl—Ph | CH₂CH=CH₂ | 2.53(t, 1H), 2.70(t, 2H), 3.53(t, 2H), 3.85(s, 3H), 3.87–4.06(m, 2H), 4.72–4.80(m, 3H), 5.19–5.27(m, 2H), 5.83(ddd, 1H), 6.70–7.38(m, 7H) |
| E1.010 | H | 4-Cl—Ph | CH₂C(CH₃)=CH₂ | 1.69(s, 3H), 2.53(t, 1H), 2.80(t, 2H), 3.53(t, 2H), 3.86(s, 3H), 4.69–4.92(m, 5H), 6.69–7.33(m, 7H) |
| E1.011 | H | 4-Cl—Ph | CH₂C≡CH | 2.42(t, 1H), 2.47(t, 1H), 2.74(t, 2H), 3.50(t, 2H), 3.79(s, 3H), 3.91(dd, 1H, 4.14(dd, 1H), 4.69(d, 2H), 4.91(s, 1H), 6.62–7.29(m, 7H) m.p. 90–92° C. |
| E1.012 | CH₂CH₃ | 4-Cl—Ph | CH₂C≡CH | 1.28(t, 3H), 2.35(dt, 2H), 2.61(t, 1H), 2.92(t, 2H), 3.68(t, 2H), 4.01(s, 3H), 4.09(dd, 1H, 4.32(dd, 1H), 4.88(d, 2H), 5.12(s, 1H), 6.80–7.52(m, 7H) |
| E1.013 | 4-Cl—Ph | 4-Cl—Ph | CH₂C≡CH | m.p. 131–133° C. |
| E1.014 | H | 4-Cl—Ph | CH₂C≡CCH₃ | 1.88(s, 3H), 2.52(t, 1H), 2.80(t, 2H), 3.54(t, 2H), 3.83(s, 3H), 3.95(dd, 1H, 4.15(dd, 1H), 4.78(d, 2H), 4.98(s, 1H), 6.69–7.32(m, 7H) |
| E1.015 | H | 4-Cl—Ph | CH₂C≡CCH₂CH₃ | 1.18(t, 3H), 2.23(dt, 2H), 2.53(t, 1H), 2.82(t, 2H), 3.06(t, 2H), 3.86(s, 3H), 3.98(dd, |

| | | | | |
|---|---|---|---|---|
| | | | | 1H), 4.18(dd, 1H), 4.77(d, 2H), 4.98(s, 1H), 6.70–7.33(m, 7H) |
| E1.016 | H | 4-Cl—Ph | CH$_2$C≡C-cycl-C$_3$H$_5$ | 0.49–0.68(m, 5H), 2.35(t, 1H), 2.63(t, 2H), 3.39(t, 2H), 3.70(s, 3H), 3.79(dd, 1H), 3.99(dd, 1H), 4.60(d, 2H), 4.80(s, 1H), 6.53–7.18(m, 7H) |
| E1.017 | H | 4-Cl—Ph | C(CH$_3$)$_2$C≡CH | 1.35(s, 3H), 1.48(s, 3H), 2.42(s, 1H), 2.49(t, 1H), 2.78(t, 2H), 3.53(t, 2H), 3.84(s, 3H), 4.73(d, 2H), 5.16(s, 1H), 6.70–7.38(m, 7H) |
| E1.018 | H | 4-Cl—Ph | CH$_2$OCH$_2$CH$_3$ | 1.05(t, 3H), 2.43(t, 1H), 2.72(t, 2H), 3.31–3.52(m, 4H), 3.77(s, 3H), 4.53(dd, 2H), 4.67(d, 2H), 4.94(s, 1H), 6.58–7.25(m, 7H) |
| E1.019 | H | 4-Br—Ph | CH$_3$ | 2.58(t, 1H), 2.83(t, 2H), 3.38(s, 3H), 3.58(t, 2H), 3.90(s, 3H), 4.62(s, 1H), 4.83(d, 2H), 6.73–7.52(m, 7H) |
| E1.020 | H | 4-Br—Ph | CH$_2$CH$_3$ | 1.19(t, 3H), 2.53(t, 1H), 2.79(t, 2H), 3.40–3.57(m, 4H), 3.84(s, 3H), 4.66(s, 1H), 4.75(d, 2H), 6.68–7.49(m, 7H) |
| E1.021 | H | 4-Br—Ph | CH$_2$CH=CH$_2$ | 2.60(t, 1H), 2.95(t, 2H), 3.71(t, 2H), 4.03(s, 3H), 4.05–4.20(m, 2H), 4.90(s, 1H), 4.93(d, 2H), 5.36–5.47(m, 2H), 6.01(ddd, 1H), 6.86–7.22(m, 7H) |
| E1.022 | H | 4-Br—Ph | CH$_2$C≡CH | 2.51(t, 1H), 2.54(t, 1H), 2.81(t, 2H), 3.54(t, 2H), 3.86(s, 3H), 3.97(dd, 1H, 4.20(dd, 1H), 4.78(d, 2H), 4.96(s, 1H), 6.70–7.52(m, 7H) m.p. 92–94° C. |
| E1.023 | CH$_2$CH$_3$ | 4-Br—Ph | CH$_2$C≡CH | 0.92(t, 3H), 2.03(dt, 2H), 2.29(t, 1H), 2.58(t, 2H), 3.33(t, 2H), 3.63(s, 3H), 3.78(dd, 1H, 3.98(dd, 1H), 4.05(d, 2H), 4.26(s, 1H), 6.48–7.29(m, 7H) |
| E1.024 | 4-Cl—Ph | 4-Br—Ph | CH$_2$C≡CH | 2.50(t, 1H), 2.82(t, 2H), 3.56(t, 2H), 3.89(s, 3H), 3.99(dd, 1H), 4.19(dd, 1H), 4.96–5.00(m, 3H), 6.69–7.51(m, 11H) |
| E1.025 | H | 4-Br—Ph | CH$_2$C≡CCH$_3$ | 1.88(s, 3H), 2.51(t, 1H), 2.80(t, 2H), 3.53(t, 2H), 3.87(s, 3H), 3.93(dd, 1H, 4.14(dd, 1H), 4.79(d, 2H), 4.98(s, 1H), 6.68–7.49(m, 7H) |
| E1.026 | H | 4-Br—Ph | CH$_2$C≡CCH$_2$CH$_3$ | 1.05(t, 3H), 2.14(dt, 2H), 2.44(t, 1H), 2.70(t, 2H), 3.42(t, 2H), 3.73(s, 3H), 3.86(dd, 1H), 4.09(dd, 1H), 4.68(d, 2H), 4.88(s, 1H), 6.58–7.42(m, 7H) |
| E1.027 | H | 4-Br—Ph | CH$_2$C≡C-cycl-C$_3$H$_5$ | 0.59–0.81(m, 5H), 2.49(t, 1H), 2.73(t, 2H), 3.50(t, 2H), 3.81(s, 3H), 3.89(dd, 1H), 4.10(dd, 1H), 4.72(d, 2H), 4.89(s, 1H), 6.62–7.49(m, 7H) |
| E1.028 | H | 4-Br—Ph | CH$_2$Ph | 2.51(t, 1H), 2.80(t, 2H), 3.54(t, 2H), 3.82(s, 3H), 4.45(dd, 2H), 4.72–4.80(m, 3H), 6.68–7.50(m, 12H) |
| E1.029 | H | 3-F—Ph | CH$_2$CH$_3$ | 1.37(t, 3H), 2.66(t, 1H), 2.93(t, 2H), 3.55–3.72(m, 4H), 3.99(s, 3H), 4.83(s, 1H), 4.92(d, 2H), 6.82–7.49(m, 7H) |
| E1.030 | H | 3-F—Ph | CH$_2$C≡CH | 2.28(t, 2H), 2.56(t, 2H), 3.32(t, 2H), 3.62(s, 3H), 3.78(dd, 1H), 3.98(dd, 1H), 4.53(d, 2H), 4.78(s, 1H), 6.47–7.12(m, 7H) |

| | | | | |
|---|---|---|---|---|
| E1.031 | H | 4-F—Ph | CH₃ | 2.42(t, 1H), 2.70(t, 2H), 3.22 (s, 3H), 3.44(t, 2H), 3.73(s, 3H), 4.49(s, 1H), 4.67(d, 2H), 6.58–7.22(m, 7H) |
| E1.032 | H | 4-F—Ph | CH₂CH₃ | 0.99(t, 3H), 2.29(t, 1H), 2.58 (t, 2H), 3.20–3.37(m, 4H), 3.63(s, 3H), 4.44(s, 1H), 4.53(d, 2H), 6.48–7.12(m, 7H) |
| E1.033 | H | 4-F—Ph | CH₂C≡CH | 2.45(t, 2H), 2.76(t, 2H), 3.50 (t, 2H), 3.79(s, 3H), 3.91(dd, 1H), 4.12(dd, 1H), 4.72(d, 2H), 4.93(s, 1H), 6.61–7.28 (m, 7H) |
| E1.034 | H | 2-Cl—Ph | CH₃ | 2.53(t, 1H), 2.84(t, 2H), 3.33 (s, 3H), 3.59(t, 2H), 3.84(s, 3H), 4.75(d, 2H), 5.13(s, 1H), 6.72–7.40(m, 7H) |
| E1.035 | H | 2-Cl—Ph | CH₂CH₃ | 1.04(t, 3H), 2.35(t, 1H), 2.69 (t, 2H), 3.30–3.49(m, 4H), 3.72(s, 3H), 4.62(d, 2H), 5.10(s, 1H), 6.59–7.28(m, 7H) |
| E1.036 | H | 2-Cl—Ph | CH₂C≡CH | 2.72(t, 1H), 2.75(t, 1H), 3.06 (t, 2H), 3.82(t, 2H), 4.08(s, 3H), 4.24(dd, 1H), 4.43(dd, 1H), 4.99(d, 2H), 5.71(s, 1H), 6.97–7.62(m, 7H) |
| E1.037 | H | 3-Cl—Ph | CH₂CH₃ | 1.00(t, 3H), 2.30(t, 1H), 2.58 (t, 2H), 3.21–3.35(m, 4H), 3.63(s, 3H), 4.46(s, 1H), 4.54(d, 2H), 6.47–7.16(m, 7H) |
| E1.038 | H | 3-Cl—Ph | CH₂C≡CH | 2.69(t, 2H), 2.99(t, 2H), 3.72 (t, 2H), 4.03(s, 3H), 4.17(dd, 1H), 4.40(dd, 1H), 4.95(d, 2H), 5.16(s, 1H), 6.87–7.56 (m, 7H) |
| E1.039 | H | 3-Br—Ph | CH₂CH₃ | 1.13(t, 3H), 2.44(t, 1H), 2.71 (t, 2H), 3.33–3.48(m, 4H), 3.78(s, 3H), 4.58(s, 1H), 4.69(d, 2H), 6.60–7.46(m, 7H) |
| E1.040 | H | 3-Br—Ph | CH₂C≡CH | 2.42(t, 2H), 2.72(t, 2H), 3.47 (t, 2H), 3.78(s, 3H), 3.91(dd, 1H), 4.12(dd, 1H), 4.70(d, 2H), 4.89(s, 1H), 6.60–7.44 (m, 7H) |
| E1.041 | H | 3-H₃C—Ph | CH₂CH₃ | 1.20(t, 3H), 2.36(s, 3H), 2.53 (t, 1H), 2.82(t, 2H), 3.41–3.58(m, 4H), 3.85(s, 3H), 4.68(s, 1H), 4.78(d, 2H), 6.72–7.28(m, 7H) |
| E1.042 | H | 3-H₃C—Ph | CH₂C≡CH | 2.29(s, 3H), 2.40(t, 1H), 2.44 (t, 1H), 2.72(t, 2H), 3.47(t, 2H), 3.78(s, 3H), 3.89(dd, 1H), 4.09(dd, 1H), 4.69(d, 2H), 4.88(s, 1H), 6.62–7.19 (m, 7H) |
| E1.043 | H | 4-H₃C—Ph | CH₃ | 2.46(s, 3H), 2.63(t, 1H), 2.92 (t, 2H), 3.41(s, 3H), 3.63(t, 2H), 3.95(s, 3H), 4.68(s, 1H), 4.87(d, 2H), 6.81–7.39(m, 7H) |
| E1.044 | H | 4-H₃C—Ph | CH₂CH₃ | 1.09(t, 3H), 2.28(s, 3H), 2.42 (t, 1H), 2.71(t, 2H), 3.30–3.49(m, 4H), 3.76(s, 3H), 4.57(s, 1H), 4.68(d, 2H), 6.61–7.19(m, 7H) |
| E1.045 | H | 4-H₃C—Ph | CH₂C≡CH | 2.38(s, 3H), 2.49(t, 1H), 2.52 (t, 1H), 2.80(t, 2H), 3.57(t, 2H), 3.83(s, 3H), 3.95(dd, 1H), 4.18(dd, 1H), 4.78(d, 2H), 4.97(s, 1H), 6.71–7.29 (m, 7H) m.p. 81–82° C. |
| E1.046 | H | 3-F₃C—Ph | CH₂CH₃ | 1.30(t, 3H), 2.59(t, 1H), 2.86 (t, 2H), 3.53 3.64(m, 4H), 3.92(s, 3H), 4.80–4.85(m, 3H), 6.74–7.73(m, 7H) |
| E1.047 | H | 3-F₃C—Ph | CH₂C≡CH | 2.43(t, 2H), 2.72(t, 2H), 3.45 (t, 2H), 3.77(s, 3H), 3.93(dd, |

| | | | | |
|---|---|---|---|---|
| | | | | 1H), 4.15(dd, 1H), 4.70(d, 2H), 4.98(s, 1H), 6.60–7.57 (m, 7H) |
| E1.048 | H | 4-F₃C—Ph | CH₃ | 2.57(t, 1H), 2.80(t, 2H), 3.35 (s, 3H), 3.55(t, 2H), 3.85(s, 3H), 4.68(s, 1H), 4.78(d, 2H), 6.65–7.62(m, 7H) |
| E1.049 | H | 4-F₃C—Ph | CH₂CH₃ | 1.22(t, 3H), 2.52(t, 1H), 2.79 (t, 2H), 3.43–3.57(m, 4H), 3.86(s, 3H), 4.78(d, 2H), 5.31(s, 1H), 6.68–7.62(m, 7H) |
| E1.050 | H | 4-F₃C—Ph | CH₂C≡CH | 2.58(t, 2H), 2.83(t, 2H), 3.60 (t, 2H), 3.91(s, 3H), 4.05(dd, 1H), 4.28(dd, 1H), 4.80(d, 2H), 5.12(s, 1H), 6.72–7.67(m, 7H) |
| E1.051 | H | 4-C₂H₅—Ph | CH₃ | 1.15(t, 3H), 2.43(t, 1H), 2.57 (t, 2H), 2.71(t, 2H), 3.24(s, 3H), 3.46(t, 2H), 3.77(s, 3H), 4.49(s, 1H), 4.68(d, 2H), 6.60–7.19(m, 7H) |
| E1.052 | H | 4-C₂H₅—Ph | CH₂CH₃ | 1.08–1.20(m, 6H), 2.43(t, 1H), 2.58(t, 2H), 2.72(t, 2H), 3.32–3.51(m, 4H), 3.76(s, 3H), 4.59(s, 1H), 4.69(d, 2H), 6.62–7.20(m, 7H) |
| E1.053 | H | 4-C₂H₅—Ph | CH₂C≡CH | 1.18(t, 3H), 2.40(t, 1H), 2.45 (t, 1H), 2.56(t, 2H), 2.73(t, 2H), 3.49(t, 2H), 3.78(s, 3H), 3.90(dd, 1H), 4.08(dd, 1H), 4.69(d, 2H), 4.90(s, 1H), 6.62–7.20(m, 7H) |
| E1.054 | H | 4-CH₂=CH—Ph | CH₂CH₃ | 1.32(t, 3H), 2.64(t, 1H), 2.93 (t, 2H), 3.54–3.71(m, 4H), 3.97(s, 3H), 4.83(s, 1H), 4.91(d, 2H), 5.40(d, 1H), 5.89(d, 1H), 6.81–7.53(m, 7H) |
| E1.055 | H | 4-CH₂=CH—Ph | CH₂C≡CH | 2.50(t, 1H), 2.54(t, 1H), 2.82 (t, 2H), 3.57(t, 2H), 3.84(s, 3H), 4.00(dd, 1H), 4.19(dd, 1H), 4.78(d, 2H), 5.01(s, 1H), 5.27(d, 1H), 5.76(d, 1H), 6.68–7.43(m, 7H) |
| E1.056 | H | 4-HC≡C—Ph | CH₂CH₃ | 0.97(t, 3H), 2.28(t, 1H), 2.54 (t, 2H), 2.83(s, 1H), 3.19–3.32(m, 4H), 3.62(s, 3H), 4.46(s, 1H), 4.53(d, 2H), 6.43–7.35(m, 7H) |
| E1.057 | H | 4-HC≡C—Ph | CH₂C≡CH | 2.26(t, 1H), 2.30(t, 1H), 2.57 (t, 2H), 2.85(s, 1H), 3.31(t, 2H), 3.61(s, 3H), 3.73(dd, 1H), 3.96(dd, 1H), 4.54(d, 2H), 4.77(s, 1H), 6.43–7.22(m, 7H) |
| E1.058 | H | 3-N≡C—Ph | CH₂CH₃ | 1.02(t, 3H), 2.32(t, 1H), 2.60 (t, 2H), 3.27–3.38(m, 4H), 3.65(s, 3H), 4.53(s, 1H), 4.58(d, 2H), 6.50–7.52(m, 7H) |
| E1.059 | H | 3-N≡C—Ph | CH₂C≡CH | 2.38(t, 2H), 2.67(t, 2H), 3.41 (t, 2H), 3.71(s, 3H), 3.85(dd, 1H), 4.09(dd, 1H), 4.63(d, 2H), 4.88(s, 1H), 6.52–7.53 (m, 7H) |
| E1.060 | H | 4-N≡C—Ph | CH₂CH₃ | 1.09(t, 3H), 2.39(t, 1H), 2.63 (t, 2H), 3.32–3.43(m, 4H), 3.71(s, 3H), 4.60(s, 1H), 4.64(d, 2H), 6.53–7.50(m, 7H) |
| E1.061 | H | 4-N≡C—Ph | CH₂C≡CH | 2.54(t, 2H), 2.79(t, 2H), 3.53 (t, 2H), 3.84(s, 3H), 4.04(dd, 1H), 4.24(dd, 1H), 4.73–4.79(m, 3H), 6.25–7.68(m, 7H) |
| E1.062 | H | 4-n-C₃H₇—Ph | CH₃ | 0.79(t, 3H), 1.46(q, 2H), 2.34 (t, 1H), 2.42(t, 2H), 2.62(t, 2H), 3.15(s, 3H), 3.37(t, 2H), 3.68(s, 3H), 4.40(s, 1H), 4.59(d, 2H), 6.52–7.09(m, 7H) |

| | | | | |
|---|---|---|---|---|
| E1.063 | H | 4-n-C$_3$H$_7$—Ph | CH$_2$CH$_3$ | 1.03(t, 3H), 1.28(t, 3H), 1.69 (q, 2H), 2.57(t, 1H), 2.63(t, 2H), 2.85(t, 2H), 3.46–3.62 (m, 4H), 3.92(s, 3H), 4.73(s, 1H), 4.84(d, 2H), 6.77–7.32 (m, 7H) |
| E1.064 | H | 4-n-C$_3$H$_7$—Ph | CH$_2$C≡CH | 1.11(t, 3H), 1.78(q, 2H), 2.63 (t, 1H), 2.70(t, 1H), 2.76(t, 2H), 2.99(t, 2H), 3.72(t, 2H), 4.04(s, 3H), 4.13(dd, 1H), 4.34(dd, 1H), 4.93(d, 2H), 5.14(s, 1H), 6.88–7.43(m, 7H) |
| E1.065 | H | 4-i-C$_3$H$_7$—Ph | CH$_2$CH$_3$ | 1.13–1.29(m, 9H), 2.53(t, 1H), 2.81(t, 2H), 3.39–3.58 (m, 4H), 3.85(s, 3H), 4.67(s, 1H), 4.78(d, 2H), 6.69–7.30 (m, 7H) |
| E1.066 | H | 4-i-C$_3$H$_7$—Ph | CH$_2$C≡CH | 1.22(s, 3H), 1.26(s, 3H), 2.45(t, 1H), 2.51(t, 1H), 2.80 (t, 2H), 3.54(t, 2H), 3.83(s, 3H), 3.95(dd, 1H), 4.16(dd, 1H), 4.73(d, 2H), 4.96(s, 1H), 6.70–7.26(m, 7H) |
| E1.067 | H | 4-t-C$_4$H$_9$—Ph | CH$_2$CH$_3$ | 1.19(t, 3H), 1.31(s, 9H), 2.50 (t, 1H), 2.79(t, 2H), 3.40–3.53(m, 4H), 3.82(s, 3H), 4.68(s, 1H), 4.73(d, 2H), 6.68–7.37(m, 7H) |
| E1.068 | H | 4-t-C$_4$H$_9$—Ph | CH$_2$C≡CH | 1.13(s, 9H), 2.29(t, 1H), 2.33 (t, 1H), 2.62(t, 2H), 3.38(t, 2H), 3.64(s, 3H), 3.78(dd, 1H), 3.98(dd, 1H), 4.59(d, 2H), 4.80(s, 1H), 6.51–7.20 (m, 7H) |
| E1.069 | H | 4-H$_3$CO$_2$C—Ph | CH$_2$C≡CH | 2.31(t, 1H), 2.34(t, 1H), 2.62 (t, 2H), 3.37(t, 2H), 3.67(s, 3H), 3.76(s, 3H), 3.81(dd, 1H), 4.02(dd, 1H), 4.58(d, 2H), 4.87(s, 1H), 6.49–7.83 (m, 7H) |
| E1.070 | H | 4-H$_3$CS—Ph | CH$_2$CH$_3$ | 1.20(t, 3H), 2.49(s, 3H), 2.54 (t, 1H), 2.81(t, 2H), 3.41–3.57(m, 4H), 3.83(s, 3H), 4.68(s, 1H), 4.77(d, 2H), 6.69–7.30(m, 7H) |
| E1.071 | H | 4-H$_3$CS—Ph | CH$_2$C≡CH | 2.51–2.58(m, 5H), 2.82(t, 2H), 3.58(t, 2H), 3.88(s, 3H), 4.01(dd, 1H), 4.22(dd, 1H), 4.81(d, 2H), 5.02(s, 1H), 6.73–7.32(m, 7H) |
| E1.072 | H | 4-H$_3$CO—Ph | CH$_2$CH$_3$ | 1.28(t, 3H), 2.62(t, 1H), 2.89 (t, 2H), 3.48–3.66(m, 4H), 3.90(s, 3H), 3.93(s, 3H), 4.73(s, 1H), 4.85(d, 2H), 6.80–7.38(m, 7H) |
| E1.073 | H | 4-H$_3$CO—Ph | CH$_2$C≡CH | 2.43(t, 1H), 2.49(t, 1H), 2.78 (t, 2H), 3.52(t, 2H), 3.78(s, 3H), 3.82(s, 3H), 3.90(dd, 1H), 4.12(dd, 1H), 4.72(d, 2H), 4.91(s, 1H), 6.67–7.23 (m, 7H) |
| E1.074 | H | 3-F$_3$CO—Ph | CH$_2$CH$_3$ | 1.17(t, 3H), 2.47(t, 1H), 2.75 (t, 2H), 3.40–3.52(m, 4H), 3.82(s, 3H), 4.67(s, 1H), 4.72(d, 2H), 6.64–7.35(m, 7H) |
| E1.075 | H | 3-F$_3$CO—Ph | CH$_2$C≡CH | 2.40(t, 2H), 2.69(t, 2H), 3.45 (t, 2H), 3.73(s, 3H), 3.91(dd, 1H), 4.12(dd, 1H), 4.67(d, 2H), 4.92(s, 1H), 6.59–7.30 (m, 7H) |
| E1.076 | H | 4-F$_3$CO—Ph | CH$_2$CH$_3$ | 1.00(t, 3H), 2.31(t, 1H), 2.60 (t, 2H), 3.27–3.38(m, 4H), 3.64(s, 3H), 4.51(s, 1H), 4.56(d, 2H), 6.49–7.21(m, 7H) |
| E1.077 | H | 4-F$_3$CO—Ph | CH$_2$C≡CH | 2.42(t, 2H), 2.73(t, 2H), 3.48 (t, 2H), 3.78(s, 3H), 3.91(dd, 1H), 4.13(dd, 1H), 4.69(d, 2H), 4.94(s, 1H), 6.61–7.32 (m, 7H) |

| | | | | |
|---|---|---|---|---|
| E1.078 | H | 4-C$_2$H$_5$O—Ph | CH$_2$CH$_3$ | 1.27(t, 3H), 1.49(t, 3H), 2.58 (t, 1H), 2.87(t, 2H), 3.43– 3.62(m, 4H), 3.91(s, 3H), 4.09(q, 2H), 4.71(s, 1H), 4.82(d, 2H), 6.78–7.35(m, 7H) |
| E1.079 | H | 4-C$_2$H$_5$O—Ph | CH$_2$C≡CH | 1.19(t, 3H), 2.22(t, 1H), 2.28 (t, 1H), 2.57(t, 2H), 3.31(t, 2H), 3.62(s, 3H), 3.72(dd, 1H), 3.81(q, 2H), 3.92(dd, 1H), 4.53(d, 2H), 4.70(s, 1H), 6.48–7.04(m, 7H) |
| E1.080 | H | 4-(HC≡CCH$_2$O)—Ph | CH$_2$C≡CH | 2.21–2.33(m, 3H), 2.59(t, 2H), 3.33(t, 2H), 3.62(s, 3H), 3.73(dd, 1H), 3.95(dd, 1H), 4.49(d, 2H), 4.56(d, 2H), 4.74(s, 1H), 6.43–7.08(m, 7H) |
| E1.081 | H | 4-PhO—Ph | CH$_2$CH$_3$ | 1.10(t, 3H), 2.39(t, 1H), 2.70 (t, 2H), 3.32–3.46(m, 4H), 3.73(s, 3H), 4.58(s, 1H), 4.66(d, 2H), 6.59–7.27(m, 12H) |
| E1.082 | H | 4-PhO—Ph | CH$_2$C≡CH | 2.59(t, 2H), 2.92(t, 2H), 3.68 (t, 2H), 3.95(s, 3H), 4.09(dd, 1H), 4.30(dd, 1H), 4.83(d, 2H), 5.09(s, 1H), 6.82–7.48 (m, 12H) |
| E1.083 | H | 3,4-F$_2$—Ph | CH$_3$ | 2.50(t, 1H), 2.80(t, 2H), 3.33 (s, 3H), 3.55(t, 2H), 3.87(s, 3H), 4.55(s, 1H), 4.79(d, 2H), 6.65–7.28(m, 6H) |
| E1.084 | H | 3,4-F$_2$—Ph | CH$_2$CH$_3$ | 1.21(t, 3H), 2.53(t, 1H), 2.79 (t, 2H), 3.43–3.58(m, 4H), 3.88(s, 3H), 4.63(s, 1H), 4.78(d, 2H), 6.68–7.28(m, 6H) |
| E1.085 | H | 3,4-F$_2$—Ph | CH$_2$C≡CH | 2.70(t, 2H), 2.98(t, 2H), 3.72 (t, 2H), 4.05(s, 3H), 4.18(dd, 1H), 4.39(dd, 1H), 4.95(d, 2H), 5.12(s, 1H), 6.85–7.46 (m, 6H) |
| E1.086 | H | 3,5-F$_2$—Ph | CH$_2$CH$_3$ | 0.99(t, 3H), 2.28(t, 1H), 2.55 (t, 2H), 3.20–3.33(m, 4H), 3.62(s, 3H), 3.94(s, 1H), 4.53(d, 2H), 6.44–7.04(m, 6H) |
| E1.087 | H | 3,5-F$_2$—Ph | CH$_2$C≡CH | 2.72(t, 2H), 3.00(t, 2H), 3.74 (t, 2H), 4.07(s, 3H), 4.22(dd, 1H), 4.43(dd, 1H), 4.98(d, 2H), 5.19(s, 1H), 6.89–7.48 (m, 6H) |
| E1.088 | H | 3-Cl-4-F—Ph | CH$_3$ | 2.49(t, 1H), 2.77(t, 2H), 3.32 (s, 3H), 3.51(t, 2H), 3.83(s, 3H), 4.54(s, 1H), 4.75(d, 2H), 6.66–7.42(m, 6H) |
| E1.089 | H | 3-Cl-4-F—Ph | CH$_2$CH$_3$ | 1.12(t, 3H), 2.43(t, 1H), 2.71 (t, 2H), 3.33–3.49(m, 4H), 3.78(s, 3H), 4.56(s, 1H), 4.69(d, 2H), 6.59–7.38(m, 6H) |
| E1.090 | H | 3-Cl-4-F—Ph | CH$_2$C≡CH | 2.54(t, 2H), 2.81(t, 2H), 3.54 (t, 2H), 3.88(s, 3H), 3.99(dd, 1H), 4.22(dd, 1H), 4.79(d, 2H), 4.95(s, 1H), 6.68–7.45 (m, 6H) |
| E1.091 | H | 4-Cl-3-F—Ph | CH$_2$C≡CH | 2.52(t, 2H), 2.79(t, 2H), 3.55 (t, 2H), 3.85(s, 3H), 3.99(dd, 1H), 4.20(dd, 1H), 4.75(d, 2H), 4.96(s, 1H), 6.69–7.41 (m, 6H) |
| E1.092 | H | 3-F-4-H$_3$CO—Ph | CH$_2$CH$_3$ | 1.06(t, 3H), 2.38(t, 1H), 2.65 (t, 2H), 3.27–3.43(m, 4H), 3.71(s, 3H), 3.74(s, 3H), 4.50(s, 1H), 4.62(d, 2H), 6.57– 7.13(m, 6H) |
| E1.093 | H | 3-F-4-H$_3$CO—Ph | CH$_2$C≡CH | 2.41(t, 1H), 2.44(t, 1H), 2.72 (t, 2H), 3.48(t, 2H), 3.77(s, 3H), 3.82(s, 3H), 3.89(dd, 1H), 4.11(dd, 1H), 4.69(d, 2H), 4.85(s, 1H), 6.60–6.96 (m, 6H) |

| | | | | |
|---|---|---|---|---|
| E1.094 | H | 3-Br-4-F—Ph | CH₂CH₃ | 1.14(t, 3H), 2.44(t, 1H), 2.73 (t, 2H), 3.35–3.49(m, 4H), 3.80(s, 3H), 4.57(s, 1H), 4.70(d, 2H), 6.62–7.53(m, 6H) |
| E1.095 | H | 3-Br-4-F—Ph | CH₂C≡CH | 2.35(t, 2H), 2.63(t, 2H), 3.39 (t, 2H), 3.70(s, 3H), 3.83(dd, 1H), 4.06(dd, 1H), 4.62(d, 2H), 4.81(s, 1H), 6.54–7.44 (m, 6H) |
| E1.096 | H | 4-Br-2-F—Ph | CH₂CH₃ | 0.94(t, 3H), 2.28(t, 1H), 2.60 (t, 2H), 3.19–3.41(m, 4H), 3.64(s, 3H), 4.54(d, 2H), 4.75(s, 1H), 6.51–7.06(m, 6H) |
| E1.097 | H | 4-Br-2-F—Ph | CH₂C≡CH | 2.51(t, 2H), 2.82(t, 2H), 3.58 (t, 2H), 3.87(s, 3H), 4.00(dd, 1H), 4.22(dd, 1H), 4.78(d, 2H), 5.23(s, 1H), 6.72–7.30 (m, 6H) |
| E1.098 | H | 2,4-Cl₂—Ph | CH₂CH₃ | 1.15(t, 3H), 2.50(t, 1H), 2.82 (t, 2H), 3.41–3.60(m, 4H), 3.82(s, 3H), 4.73(d, 2H), 5.15(s, 1H), 6.70–7.39(m, 6H) |
| E1.099 | H | 2,4-Cl₂—Ph | CH₂C≡CH | 2.72(t, 2H), 3.05(t, 2H), 3.80 (t, 2H), 4.09(s, 3H), 4.22(dd, 1H), 4.42(dd, 1H), 5.00(d, 2H), 5.67(s, 1H), 6.94–7.66 (m, 6H) |
| E1.100 | H | 3,4-Cl₂—Ph | CH₃ | 2.28(t, 1H), 2.54(t, 2H), 3.10 (s, 3H), 3.28(t, 2H), 3.61(s, 3H), 4.30(s, 1H), 4.54(d, 2H), 6.42–7.23(m, 6H) |
| E1.101 | H | 3,4-Cl₂—Ph | CH₂CH₃ | 1.12(t, 3H), 2.43(t, 1H), 2.70 (t, 2H), 3.33–3.50(m, 4H), 3.78(s, 3H), 4.58(s, 1H), 4.69(d, 2H), 6.59–7.42(m, 6H) |
| E1.102 | H | 3,4-Cl₂—Ph | CH₂C≡CH | 2.36(t, 2H), 2.62(t, 2H), 3.49 (t, 2H), 3.69(s, 3H), 3.83(dd, 1H), 4.06(dd, 1H), 4.60(d, 2H), 4.79(s, 1H), 6.50–7.29 (m, 6H) |
| E1.103 | H | 3,5-Cl₂—Ph | CH₂CH₃ | 1.06(t, 3H), 2.32(t, 1H), 2.61 (t, 2H), 3.24–3.39(m, 4H), 3.70(s, 3H), 4.44(s, 1H), 4.58(d, 2H), 6.50–7.12(m, 6H) |
| E1.104 | H | 3,5-Cl₂—Ph | CH₂C≡CH | 2.54(t, 2H), 2.80(t, 2H), 3.55 (t, 2H), 3.89(s, 3H), 4.03(dd, 1H), 4.25(dd, 1H), 4.79(d, 2H), 4.98(s, 1H), 6.68–7.35 (m, 6H) |
| E1.105 | H | 3-Cl-4-H₃C—Ph | CH₂CH₃ | 1.25(t, 3H), 2.42(s, 3H), 2.57 (t, 1H), 2.83(t, 2H), 3.44–3.61(m, 4H), 3.91(s, 3H), 4.68(s, 1H), 4.82(d, 2H), 6.72–7.40(m, 6H) |
| E1.106 | H | 3-Cl-4-H₃C—Ph | CH₂C≡CH | 2.40(s, 3H), 2.53(t, 2H), 2.82 (t, 2H), 3.57(t, 2H), 3.88(s, 3H), 4.00(dd, 1H), 4.22(dd, 1H), 4.79(d, 2H), 4.98(s, 1H), 6.74–7.38(m, 6H) |
| E1.107 | H | 4-Cl-3-F₃C—Ph | CH₂CH₃ | 1.14(t, 3H), 2.44(t, 1H), 2.72 (t, 2H), 3.39–3.50(m, 4H), 3.78(s, 3H), 4.63(s, 1H), 4.69(d, 2H), 6.60–7.68(m, 6H) |
| E1.108 | H | 4-Cl-3-F₃C—Ph | CH₂C≡CH | 2.29(t, 2H), 2.57(t, 2H), 3.31 (t, 2H), 3.62(s, 3H), 3.78(dd, 1H), 4.00(dd, 1H), 4.53(d, 2H), 4.80(s, 1H), 6.44–7.49 (m, 6H) |
| E1.109 | H | 3,4-Br₂—Ph | CH₂CH₃ | 1.25(t, 3H), 2.54(t, 1H), 2.82 (t, 2H), 3.46–3.57(m, 4H), 3.89(s, 3H), 4.56(s, 1H), 4.80(d, 2H), 6.68–7.67(m, 6H) |
| E1.110 | H | 3,4-Br₂—Ph | CH₂C≡CH | 2.39(t, 2H), 2.67(t, 2H), 3.41 (t, 2H), 3.72(s, 3H), 3.89(dd, 1H), 4.10(dd, 1H), 4.64(d, |

| | | | | |
|---|---|---|---|---|
| | | | | 2H), 4.82(s, 1H), 6.54–7.50 (m, 6H) |
| E1.111 | H | 3,4-(H$_3$C)$_2$—Ph | CH$_2$CH$_3$ | 1.12(t, 3H), 2.19(s, 6H), 2.44 (t, 1H), 2.72(t, 2H), 3.32–3.50(m, 4H), 3.77(s, 3H), 4.56(s, 1H), 4.70(d, 2H), 6.63–7.21(m, 6H) |
| E1.112 | H | 3,4-(H$_3$C)$_2$—Ph | CH$_2$C≡CH | 2.47(s, 6H), 2.68(t, 1H), 2.73 (t, 1H), 3.00(t, 2H), 3.75(t, 2H), 4.04(s, 3H), 4.15(dd, 1H), 4.36(dd, 1H), 4.94(d, 2H), 5.13(s, 1H), 6.92–7.48 (m, 6H) |
| E1.113 | H | 3,5-(H$_3$C)$_2$—Ph | CH$_2$CH$_3$ | 1.06(t, 3H), 2.20(s, 6H), 2.39 (t, 1H), 2.69(t, 2H), 3.27–3.45(m, 4H), 3.73(s, 3H), 4.52(s, 1H), 4.64(d, 2H), 6.59–6.92(m, 6H) |
| E1.114 | H | 3,5-(H$_3$C)$_2$—Ph | CH$_2$C≡CH | 2.38(s, 6H), 2.53(t, 1H), 2.56 (t, 1H), 2.88(t, 2H), 3.61(t, 2H), 3.92(s, 3H), 4.02(dd, 1H), 4.21(dd, 1H), 4.82(d, 2H), 4.99(s, 1H), 6.78–7.33 (m, 6H) |
| E1.115 | H | 3-H$_3$C-4-H$_3$CO—Ph | CH$_2$CH$_3$ | 1.12(t, 3H), 2.14(s, 3H), 2.45 (t, 1H), 2.75(t, 2H), 3.33–3.50(m, 4H), 3.78(s, 3H), 3.81(s, 3H), 4.58(s, 1H), 4.71(d, 2H), 6.68–7.22(m, 6H) |
| E1.116 | H | 3-H$_3$C-4-H$_3$CO—Ph | CH$_2$C≡CH | 2.24(s, 3H), 2.50(t, 1H), 2.55 (t, 1H), 2.84(t, 2H), 3.59(t, 2H), 3.87(s, 3H), 3.89(s, 3H), 3.98(dd, 1H), 4.20(dd, 1H), 4.80(d, 2H), 4.94(s, 1H), 6.73–7.30(m, 6H) |
| E1.117 | H | 3,4-(H$_3$CO)$_2$—Ph | CH$_2$CH$_3$ | 1.38(t, 3H), 2.70(t, 1H), 2.99 (t, 2H), 3.58–3.74(m, 4H), 4.03–4.10(m, 9H), 4.83(s, 1H), 4.95(d, 2H), 6.89–7.46 (m, 6H) |
| E1.118 | H | 3,4-(H$_3$CO)$_2$—Ph | CH$_2$C≡CH | 2.36(t, 1H), 2.40(t, 1H), 2.69 (t, 2H), 3.43(t, 2H), 3.72–3.77(m, 9H), 3.85(dd, 1H), 4.04(dd, 1H), 4.62(d, 2H), 4.81(s, 1H), 6.58–7.12(m, 6H) |
| E1.119 | H | 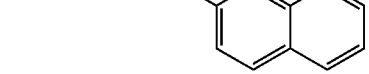 | CH$_3$ | 2.54(t, 1H), 2.81(t, 2H), 3.47 (s, 3H), 3.54(t, 2H), 3.82(s, 3H), 4.73(d, 2H), 4.78(s, 1H), 6.70–7.88(m, 10H) |
| E1.120 | H | 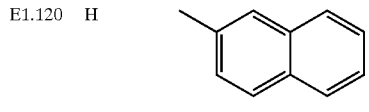 | CH$_2$CH$_3$ | 1.23(t, 3H), 2.53(t, 1H), 2.81 (t, 2H), 3.44–3.62(m, 4H), 3.85(s, 3H), 4.27(d, 2H), 4.89(s, 1H), 6.69–7.87(m, 10H) |
| E1.121 | H | 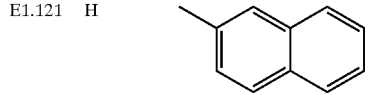 | CH$_2$C≡CH | 2.38(t, 2H), 2.69(t, 2H), 3.42 (t, 2H), 3.70(s, 3H), 3.88(dd, 1H), 4.10(dd, 1H), 4.62(d, 2H), 5.05(s, 1H), 6.54–7.70 (m, 10H) |
| E1-122 | H | 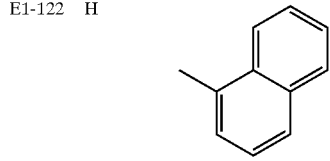 | CH$_2$CH$_3$ | 1.05(t, 3H), 2.33(t, 1H), 2.68 (t, 2H), 3.31–3.49(m, 4H), 3.68(s, 3H), 4.62(d, 2H), 5.22(s, 1H), 6.04–8.10(m, 10H) |
| E1.123 | H | 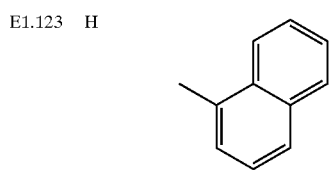 | CH$_2$C≡CH | 2.32(t, 2H), 2.65(t, 2H), 3.42 (t, 2H), 3.64(s, 3H), 3.77(dd, 1H), 4.05(dd, 1H), 4.59–4.68(m, 3H), 6.53–8.05(m, 10H) |

| | | | | |
|---|---|---|---|---|
| E1.124 | H | 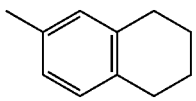 | CH₂CH₃ | 1.19(t, 3H), 1.75–1.86(m, 4H), 2.52(t, 1H), 2.73–2.86(m, 6H), 3.40–3.59(m, 4H), 3.85(s, 3H), 4.62(s, 1H), 4.75(d, 2H), 6.69–7.30(m, 6H) |
| E1.125 | H | 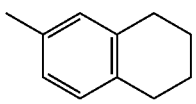 | CH₂C≡CH | 1.79–1.87(m, 4H), 2.48(t, 1H), 2.53(t, 1H), 2.72–2.85(m, 6H), 3.56(t, 2H), 3.84(s, 3H), 3.97(dd, 1H), 4.18(dd, 1H), 4.79(d, 2H), 4.93(s, 1H), 6.73–7.28(m, 6H) |
| E1.126 | H | 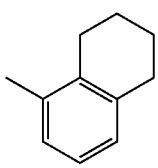 | CH₂CH₃ | 1.19(t, 3H), 1.72–1.90(m, 4H), 2.52(t, 1H), 2.69–2.83(m, 6H), 3.39–3.60(m, 4H), 3.83(s, 3H), 4.77(d, 2H), 4.98(s, 1H), 6.73–7.14(m, 6H) |
| E1.127 | H | 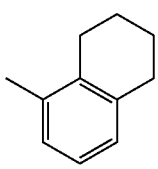 | CH₂C≡CH | 1.75–1.88(m, 4H), 2.48(t, 1H), 2.55(t, 1H), 2.75–2.90(m, 6H), 3.56(t, 2H), 3.88(s, 3H), 3.92(dd, 1H), 4.15(dd, 1H), 4.80(d, 2H), 5.32(s, 1H), 6.62–7.11(m, 6H) |
| E1.128 | H | 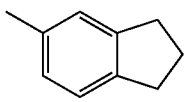 | CH₂CH₃ | 1.19(t, 3H), 2.54(t, 1H), 2.78–2.95(m, 8H), 3.39–3.56(m, 4H), 3.83(s, 3H), 4.67(s, 1H), 4.78(d, 2H), 6.69–7.25(m, 6H) |
| E1.129 | H | 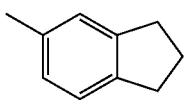 | CH₂C≡CH | 2.49(t, 1H), 2.54(t, 1H), 2.78–2.93(m, 8H), 3.55(t, 2H), 3.87(s, 3H), 3.97(dd, 1H), 4.18(dd, 1H), 4.77(d, 2H), 5.00(s, 1H), 6.72–7.29(m, 6H) |
| E1.130 | H | 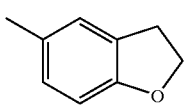 | CH₂CH₃ | 1.18(t, 3H), 2.51(t, 1H), 2.82(t, 2H), 3.19(t, 2H), 3.38–3.61(m, 4H), 3.85(s, 3H), 4.58(t, 2H), 4.62–4.75(m, 3H), 6.67–7.28(m, 6H) |
| E1.131 | H | 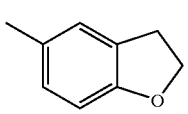 | CH₂C≡CH | 2.49(t, 1H), 2.55(t, 1H), 2.82(t, 2H), 3.19(t, 2H), 3.58(t, 2H), 3.86(s, 3H), 3.95(dd, 1H), 4.14(dd, 1H), 4.59(t, 2H), 4.77(d, 2H), 4.92(s, 1H), 6.72–7.28(m, 6H) |
| E1.132 | H | 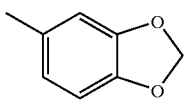 | CH₂CH₃ | 1.20(t, 3H), 2.51(t, 1H), 2.81(t, 2H), 3.40–3.61(m, 4H), 3.87(s, 3H), 4.62(s, 1H), 4.79(d, 2H), 5.96(s, 2H), 6.60–7.21(m, 6H) |
| E1.133 | H | 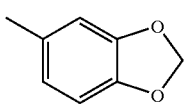 | CH₂C≡CH | 2.30(t, 1H), 2.34(t, 1H), 2.65(t, 2H), 3.39(t, 2H), 3.68(s, 3H), 3.75(dd, 1H), 3.98(dd, 1H), 4.58(d, 2H), 4.71(s, 1H), 5.72(s, 2H), 6.52–6.98(m, 6H) |
| E1.134 | H | 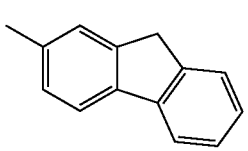 | CH₂CH₃ | 1.13(t, 3H), 2.42(t, 1H), 2.73(t, 2H), 3.37–3.52(m, 4H), 3.75(s, 3H), 3.82(s, 2H), 4.68(d, 2H), 4.70(s, 1H), 6.61–7.72(m, 10H) |

| | | | | |
|---|---|---|---|---|
| E1.135 | H | 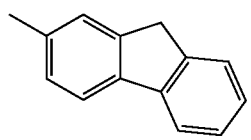 | CH₂C≡CH | 2.52(t, 2H), 2.85(t, 2H), 3.60 (t, 2H), 3.90(s, 3H), 3.92(s, 2H), 4.04(dd, 1H), 4.22(dd, 1H), 4.78(d, 2H), 5.09(s, 1H), 6.73–7.82(m, 10H) |
| E1.136 | H | 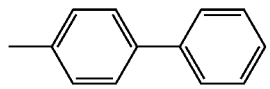 | CH₃ | 2.58(t, 1H), 2.90(t, 2H), 3.44 (s, 3H), 3.63(t, 2H), 3.92(s, 3H), 4.73(s, 1H), 4.82(d, 2H), 6.78–7.70(m, 12H) |
| E1.137 | H | 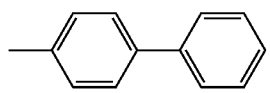 | CH₂CH₃ | 1.20(t, 3H), 2.48(t, 1H), 2.80 (t, 2H), 3.41–3.56(m, 4H), 3.82(s, 3H), 4.70–4.74(m, 3H), 6.70–7.57(m, 12H) |
| E1.138 | H | 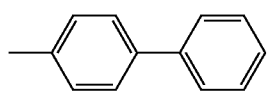 | CH₂C≡CH | 2.51(t, 2H), 2.82(t, 2H), 3.59 (t, 2H), 3.83(s, 3H), 4.03(dd, 1H), 4.22(dd, 1H), 4.74(d, 2H), 5.07(s, 1H), 6.69–7.60 (m, 12H) |
| E1.139 | H | 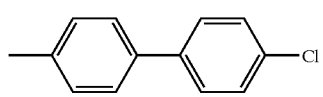 | CH₂C≡CH | m.p. 96–97° C. |
| E1.140 | H | 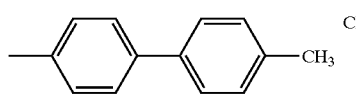 | CH₂C≡CH | m.p. 104–105° C. |
| E1.141 | H | 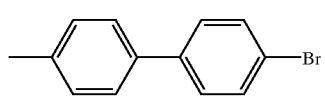 | CH₂C≡CH | m.p. 94–95° C. |
| E1.142 | H | 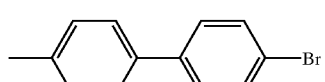 | CH₂CH=CH₂ | m.p. 80–81° C. |
| E1.143 | H | 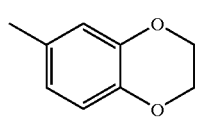 | CH₂CH₃ | 1.19(t, 3H), 2.53(t, 1H), 2.81 (t, 2H), 3.37–3.56(m, 4H), 3.87(s, 3H), 4.29(s, 4H), 4.59(s, 1H), 4.77(d, 2H), 6.71–7.02(m, 6H) |
| E1.144 | H | 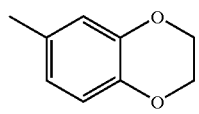 | CH₂C≡CH | 2.36(t, 1H), 2.40(t, 1H), 2.70 (t, 2H), 3.43(t, 2H), 3.76(s, 3H), 3.84(dd, 1H), 4.06(dd, 1H), 4.15(s, 4H), 4.66(d, 2H), 4.78(s, 1H), 6.61–6.90(m, 6H) |
| E1.145 | H | 3-H₃CO—Ph | CH₂CH₃ | 1.22(t, 3H), 2.52(t, 1H), 2.80 (t, 2H), 3.41–3.58(m, 4H), 3.79(s, 3H), 3.84(s, 3H), 4.68(s, 1H), 4.77(d, 2H), 6.70–7.31(m, 7H) |
| E1.146 | H | 3-H₃CO—Ph | CH₂C≡CH | 2.44(t, 1H), 2.49(t, 1H), 2.77 (t, 2H), 3.51(t, 2H), 3.78(s, 3H), 3.82(s, 3H), 3.95(dd, 1H), 4.16(dd, 1H), 4.72(d, 2H), 4.93(s, 1H), 6.64–7.28 (m, 7H) |
| E1.147 | H | 2,3,5-Cl₃—Ph | CH₂CH₃ | 1.19(t, 3H), 2.51(t, 1H), 2.82 (t, 2H), 3.45–3.59(m, 4H), 3.88(s, 3H), 4.78(d, 2H), 5.22(s, 1H), 6.73–7.47(m, 5H) |
| E1.148 | H | 2,3,5-Cl₃—Ph | CH₂C≡CH | 2.32(t, 2H), 2.63(t, 2H), 3.48 (t, 2H), 3.68(s, 3H), 3.82(dd, 1H), 4.04(dd, 1H), 4.57(d, 2H), 5.30(s, 1H), 6.53–7.29 (m, 5H) |
| E1.149 | H | 2,3-Cl₂—Ph | CH₂CH₃ | 1.41(t, 3H), 2.72(t, 1H), 3.05 (t, 2H), 3.68–3.85(m, 4H), 4.08(s, 3H), 5.00(d, 2H), 5.49(s, 1H), 6.95–7.63(m, 6H) |

| | | | | | |
|---|---|---|---|---|---|
| E1.150 | H | 2,3-Cl$_2$—Ph | | CH$_2$C≡CH | 2.53(t, 2H), 2.85(t, 2H), 3.60 (t, 2H), 3.89(s, 3H), 4.02(dd, 1H), 4.23(dd, 1H), 4.79(d, 2H), 5.54(s, 1H), 6.76–7.48 (m, 6H) |

Example E4

2-(4-Bromo-phenyl)-2-chloro-N-[2-(3-methoxy-4-prop-2-ynyloxy-phenyl)-ethyl]-acetamide

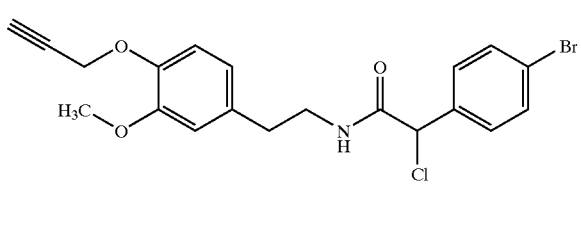

To a mixture of thionyl chloride (3.7 g, 31 mmol) in toluene (10 ml) containing 3 drops of pyridine is added 4-bromomandelic acid (2.9 g, 13 mmol) in diethylether (40 ml). The reaction mixture is refluxed for 2 hours. The solvent is removed and the residue is co-evaporated with toluene. Subsequently the residue is dissolved in dioxane (20 ml) and added to 2-(3-methoxy-4-prop-2-ynyloxy-phenyl)-ethylamine (2.2 g, 11 mmol) and triethylamine (1.0 g, 10 mmol) in dioxane (20 ml). The resulting mixture is stirred for 16 hours, diluted with water (100 ml) and extracted with ethyl acetate (2×200 ml). The combined organic layer is washed with brine (150 ml), dried over magnesium sulfate and evaporated. 2-(4-Bromo-phenyl)-2-chloro-N-[2-(3-methoxy-4-prop-2-ynyloxy-phenyl)-ethyl]-acetamide is obtained which is purified by chromatography on silica gel using ethyl/acetate/hexane as eluent. $^1$H-NMR (300 MHz, CDCl$_3$): 2.53(t, 1H, C≡CH), 2.82(t, 2H, CH$_2$CH$_2$), 3.60(t, 2H, CH$_2$CH$_2$), 3.87(s, 3H, OCH$_3$), 4.79(d, 2H, OCH$_2$), 5.29(s, 1H, CHCl), 6.70–7.48(m, 8H, CH arom., NH).

According to the above procedure of Example E2 the compounds listed in table E2 are obtained.

TABLE E4

(Ph designates phenyl)

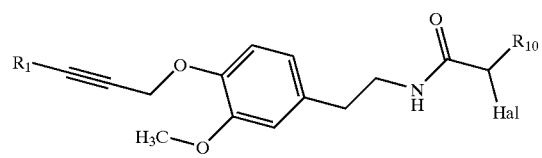

| No. | R$_1$ | R$_{10}$ | Hal | physical data in ° C. |
|---|---|---|---|---|
| E4.01 | H | 4-Br—Ph | Cl | m.p. 100–102 |
| E4.02 | C$_2$H$_5$ | 4-Br—Ph | Cl | m.p. 99–101 |
| E4.03 | H | 4-Cl—Ph | Cl | m.p. 88–91 |
| E4.04 | C$_2$H$_5$ | 4-Cl—Ph | Cl | m.p. 93–95 |

Example E5

2-(4-Bromo-phenyl)-N-[2-(3-methoxy-4-prop-2-ynyloxy-phenyl)-ethyl]-2-methylsulfanyl-acetamide

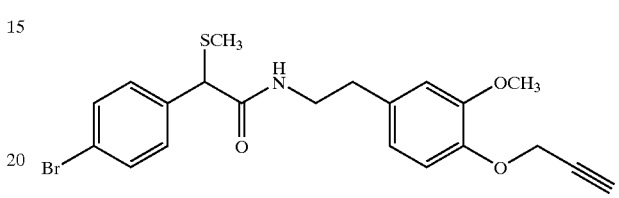

To sodium methylmercaptide (0.85 g) in 1,4-dioxane (50 ml) is added 2-(4-bromo-phenyl)-2-chloro-N-[2-(3-methoxy-4-prop-2-ynyloxy-phenyl)-ethyl]-acetamide (4.4 g). The reaction mixture is stirred under nitrogen at room temperature for 2 hours. It is extracted with ethyl acetate (2×200 ml). The organic layers are washed with brine (2×200 ml), combined, dried (MgSO$_4$) and the solvent is evaporated. 2-(4-Bromo-phenyl)-N-[2-(3-methoxy-4-prop-2-ynyloxy-phenyl)-ethyl]-2-methylthio-acetamide is obtained as an oil, which is purified by flash-column chromatography on, silica gel using ethyl acetate/hexane. $^1$H-NMR (300 MHz, CDCl$_3$): 2.00 (s, 3H), 2.52 (t, 1H), 2.80 (t, 2H), 3.56 (q, 2H), 3.82 (s, 3H), 4.36 (s, 1H), 4.75 (d, 2H), 6.67 (dd, 1H), 6.72 (d, 1H), 6.77 (t, 1H), 6.95 (d, 1H), 7.16 (d, 2H, 7.42 (d, 2H).

According to the above procedure of Example E5 the compounds listed in table E5 are obtained.

TABLE E5

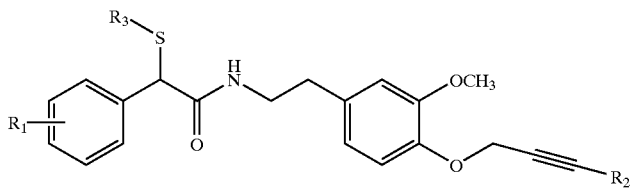

| No. | R₁ | R₂ | R₃ | ¹H-NMR (300 MHz, CDCl₃): δ = |
|---|---|---|---|---|
| E5.01 | Br | H | CH₃ | 2.00(s, 3H), 2.52(t, 1H), 2.80(t, 2H), 3.56(q, 2H), 3.82(s, 3H), 4.36(s, 1H), 4.75(d, 2H), 6.67(dd, 1H), 6.72(d, 1H), 6.77(t, 1H), 6.95(d, 1H), 7.16(d, 2H), 7.42(d, 2H) |
| E5.02 | Br | CH₂CH₃ | CH₃ | 1.12(t, 3H), 2.00(s, 3H), 2.15–2.3(m, 2H), 2.79(t, 2H), 3.56(q, 2H), 3.56(s, 3H), 4.36(s, 1H), 4.72(t, 2H), 6.66 (dd, 1H), 6.71(d, 1H), 6.79(t, 1H), 6.95(d, 1H), 7.16(d, 2H), 7.43(d, 2H). |
| E5.03 | Cl | H | CH₃ | 2.01(s, 3H), 2.52(t, 1H), 2.81(t, 2H), 3.58(q, 2H), 3.84(s, 3H), 4.38(s, 1H), 4.76(d, 2H), 6.68(dd, 1H), 7.73(d, 1H), 6.77(t, 1H), 6.96(d, 1H), 7.21(d, 2H), 7.30(d, 2H). |
| E5.04 | Cl | H | CH₂CH₃ | 1.27(t, 3H), 2.35–2.55(m, 3H), 2.80(t, 3H), 3.55(q, 2H), 3.84(s, 3H), 4.48(s, 1H), 4.76(d, 2H), 6.68(dd, 1H), 6.73 (d, 1H), 6.81(t, 1H), 6.96(d, 1H), 7.21(d, 2H), 7.27(d, 2H). |

Analogously to the above examples the compounds of tables 1 to 35 are obtained.

Ph stands for phenyl

TABLE 1

Compounds represented by the Formula I.1

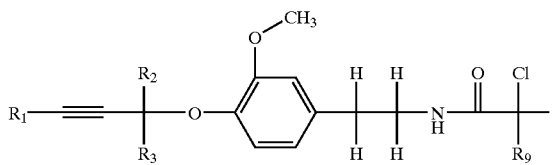

(I.1)

wherein the combination of the groups $R_1$, $R_2$, $R_3$, $R_9$ and $R_{10}$ corresponds each to one row in table A.

TABLE 2

Compounds represented by the Formula I.2

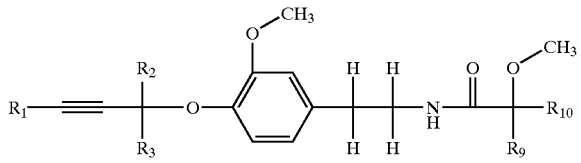

(I.2)

wherein the combination of the groups $R_1$, $R_2$, $R_3$, $R_9$ and $R_{10}$ corresponds each to one row in table A.

TABLE 3

Compounds represented by the Formula I.3

TABLE 3-continued (I.3)

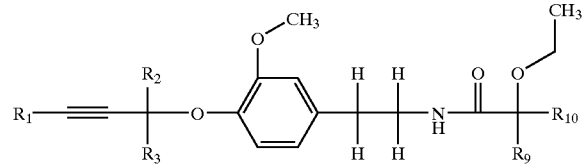

wherein the combination of the groups $R_1$, $R_2$, $R_3$, $R_9$ and $R_{10}$ corresponds each to one row in table A.

TABLE 4

Compounds represented by the Formula I.4

(I.4)

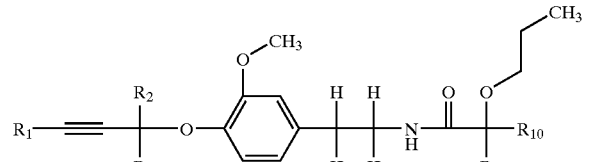

wherein the combination of the groups $R_1$, $R_2$, $R_3$, $R_9$ and $R_{10}$ corresponds each to one row in table A.

TABLE 5

Compounds represented by the Formula I.5

(I.5)

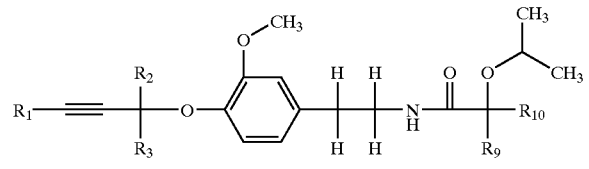

TABLE 5-continued wherein the combination of the groups $R_1$, $R_2$, $R_3$, $R_9$ and $R_{10}$ corresponds to each one row in table A.

TABLE 6

Compounds represented by the Formula I.6

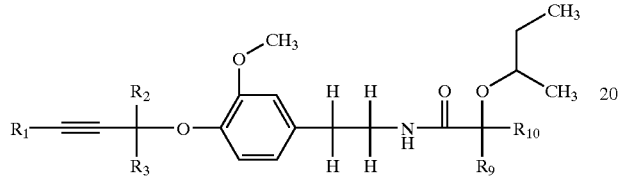
(I.6)

wherein the combination of the groups $R_1$, $R_2$, $R_3$, $R_9$ and $R_{10}$ corresponds each to one row in table A.

TABLE 7

Compounds represented by the Formula I.7

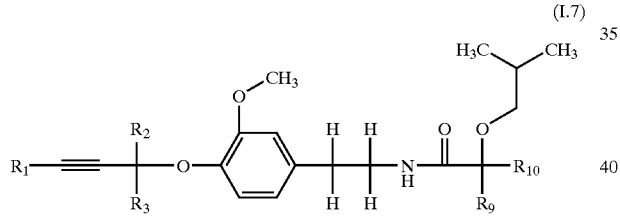
(I.7)

wherein the combination of the groups $R_1$, $R_2$, $R_3$, $R_9$ and $R_{10}$ corresponds each to one row in table A.

TABLE 8

Compounds represented by the Formula I.8

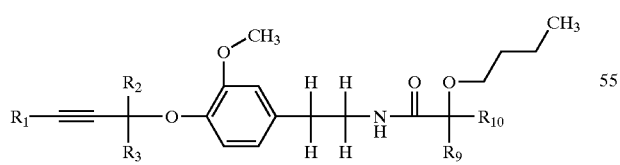
(I.8)

wherein the combination of the groups $R_1$, $R_2$, $R_3$, $R_9$ and $R_{10}$ corresponds each to one row in table A.

TABLE 9

Compounds represented by the Formula I.9

TABLE 9-continued

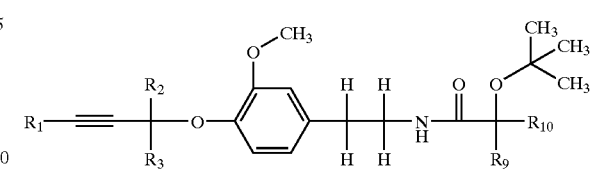
(I.9)

wherein the combination of the groups $R_1$, $R_2$, $R_3$, $R_9$ and $R_{10}$ corresponds each to one row in table A.

TABLE 10

Compounds represented by the Formula I.10

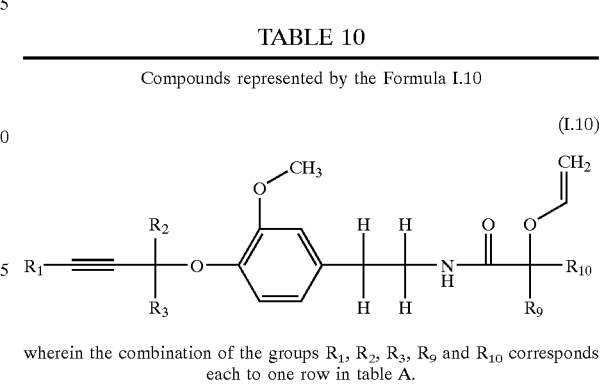
(I.10)

wherein the combination of the groups $R_1$, $R_2$, $R_3$, $R_9$ and $R_{10}$ corresponds each to one row in table A.

TABLE 11

Compounds represented by the Formula I.11

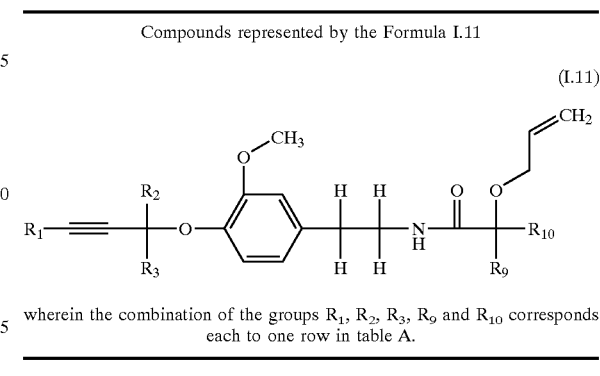
(I.11)

wherein the combination of the groups $R_1$, $R_2$, $R_3$, $R_9$ and $R_{10}$ corresponds each to one row in table A.

TABLE 12

Compounds represented by the Formula I.12

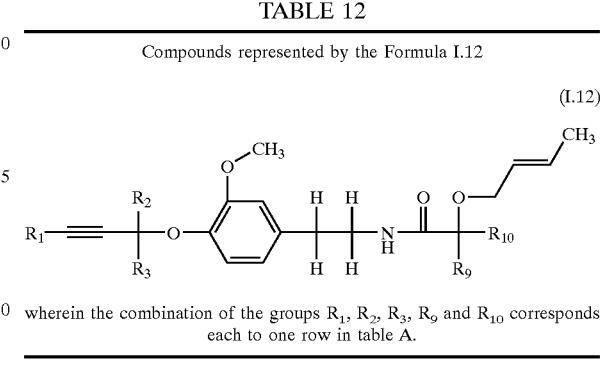
(I.12)

wherein the combination of the groups $R_1$, $R_2$, $R_3$, $R_9$ and $R_{10}$ corresponds each to one row in table A.

TABLE 13

Compounds represented by the Formula I.13

TABLE 13-continued

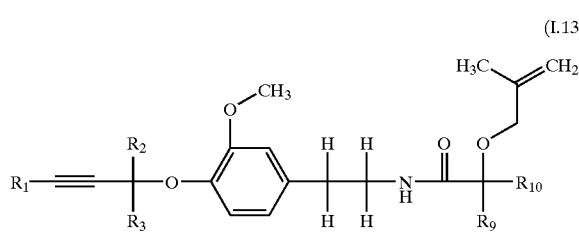

(I.13)

wherein the combination of the groups $R_1$, $R_2$, $R_3$, $R_9$ and $R_{10}$ corresponds each to one row in table A.

TABLE 14

Compounds represented by the Formula I.14

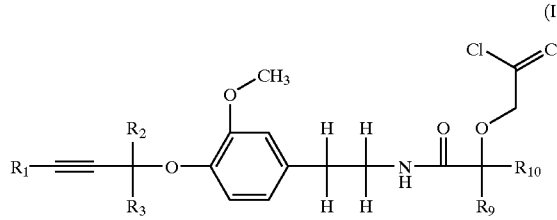

(I.14)

wherein the combination of the groups $R_1$, $R_2$, $R_3$, $R_9$ and $R_{10}$ corresponds each to one row in table A.

TABLE 15

Compounds represented by the Formula I.15

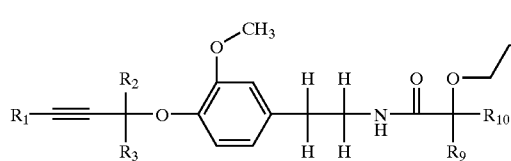

(I.15)

wherein the combination of the groups $R_1$, $R_2$, $R_3$, $R_9$ and $R_{10}$ corresponds each to one row in table A.

TABLE 16

Compounds represented by the Formula I.16

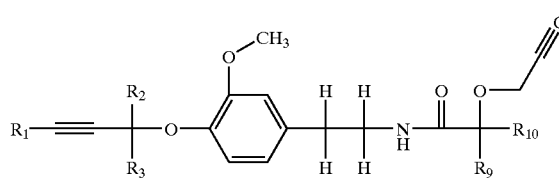

(I.16)

wherein the combination of the groups $R_1$, $R_2$, $R_3$, $R_9$ and $R_{10}$ corresponds each to one row in table A.

TABLE 17

Compounds represented by the Formula I.17

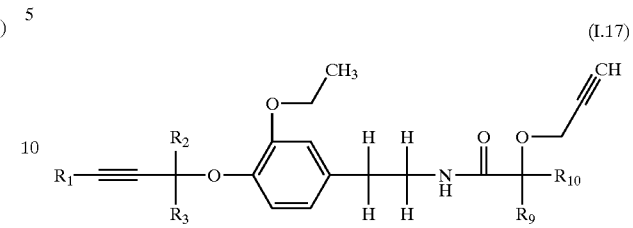

(I.17)

wherein the combination of the groups $R_1$, $R_2$, $R_3$, $R_9$ and $R_{10}$ corresponds each to one row in table A.

TABLE 18

Compounds represented by the Formula I.18

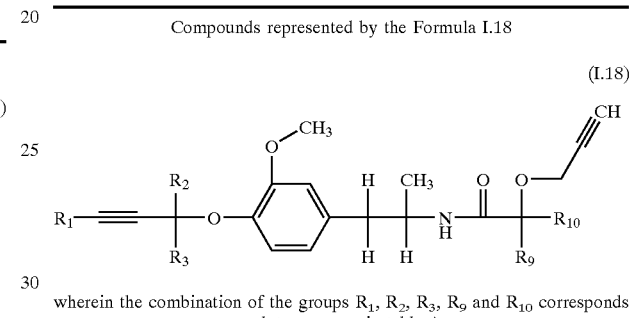

(I.18)

wherein the combination of the groups $R_1$, $R_2$, $R_3$, $R_9$ and $R_{10}$ corresponds each to one row in table A.

TABLE 19

Compounds represented by the Formula I.19

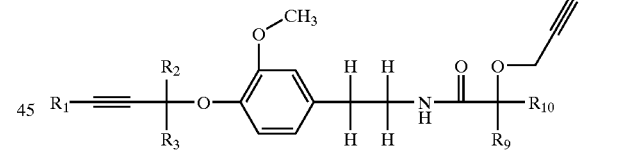

(I.19)

wherein the combination of the groups $R_1$, $R_2$, $R_3$, $R_9$ and $R_{10}$ corresponds each to one row in table A.

TABLE 20

Compounds represented by the Formula I.20

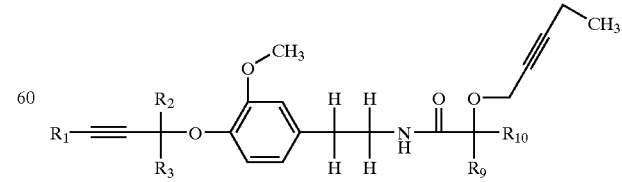

(I.20)

wherein the combination of the groups $R_1$, $R_2$, $R_3$, $R_9$ and $R_{10}$ corresponds each to one row in table A.

TABLE 21

Compounds represented by the Formula I.21

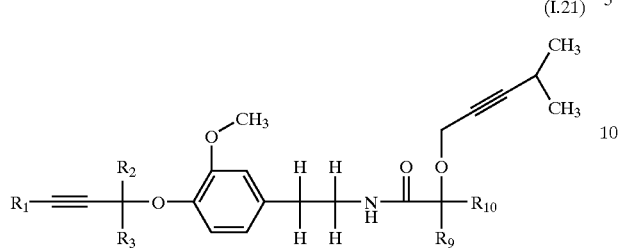

(I.21)

wherein the combination of the groups $R_1$, $R_2$, $R_3$, $R_9$ and $R_{10}$ corresponds each to one row in table A.

TABLE 22

Compounds represented by the Formula I.22

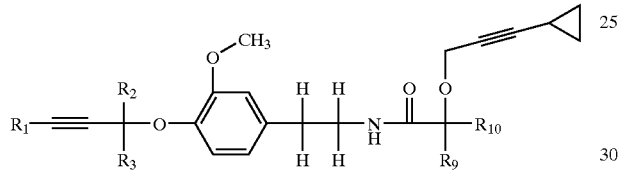

(I.22)

wherein the combination of the groups $R_1$, $R_2$, $R_3$, $R_9$ and $R_{10}$ corresponds each to one row in table A.

TABLE 23

Compounds represented by the Formula I.23

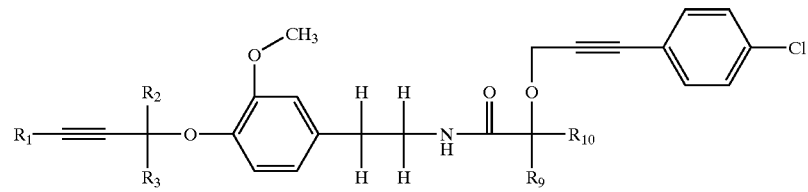

(I.23)

wherein the combination of the groups $R_1$, $R_2$, $R_3$, $R_9$ and $R_{10}$ corresponds each to one row in table A.

TABLE 24

Compounds represented by the Formula I.24

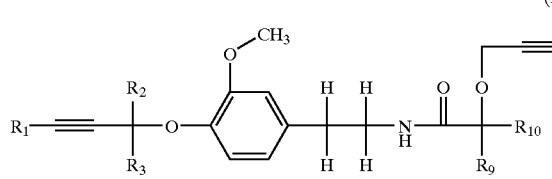

(I.24)

wherein the combination of the groups $R_1$, $R_2$, $R_3$, $R_9$ and $R_{10}$ corresponds

TABLE 24-continued each to one row in table A.

TABLE 25

Compounds represented by the Formula I.25

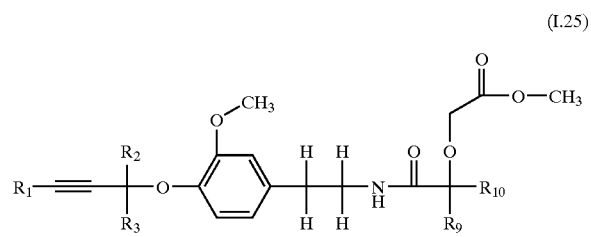

(I.25)

wherein the combination of the groups $R_1$, $R_2$, $R_3$, $R_9$ and $R_{10}$ corresponds each to one row in table A.

TABLE 26

Compounds represented by the Formula I.26

TABLE 26-continued

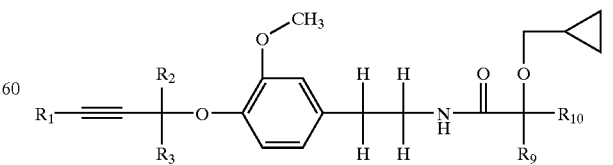

(I.26)

wherein the combination of the groups $R_1$, $R_2$, $R_3$, $R_9$ and $R_{10}$ corresponds each to one row in table A.

TABLE 27

Compounds represented by the Formula I.27

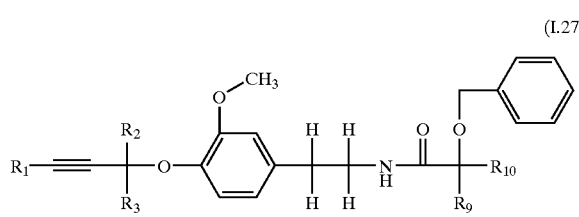

(I.27)

wherein the combination of the groups $R_1$, $R_2$, $R_3$, $R_9$ and $R_{10}$ corresponds each to one row in table A.

TABLE 28

Compounds represented by the Formula I.28

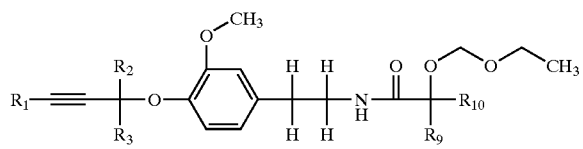

(I.28)

wherein the combination of the groups $R_1$, $R_2$, $R_3$, $R_9$ and $R_{10}$ corresponds each to one row in table A.

TABLE 29

Compounds represented by the Formula I.29

(I.29)

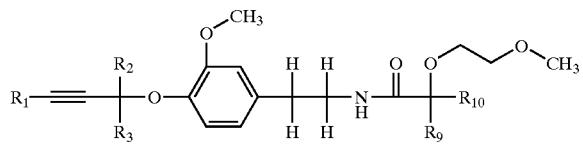

wherein the combination of the groups $R_1$, $R_2$, $R_3$, $R_9$ and $R_{10}$ corresponds each to one row in table A.

TABLE 30

Compounds represented by the Formula I.30

(I.30)

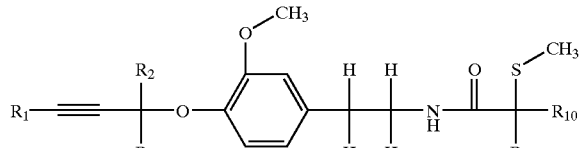

wherein the combination of the groups $R_1$, $R_2$, $R_3$, $R_9$ and $R_{10}$ corresponds each to one row in table A.

TABLE 31

Compounds represented by the Formula I.31

TABLE 31-continued (I.31)

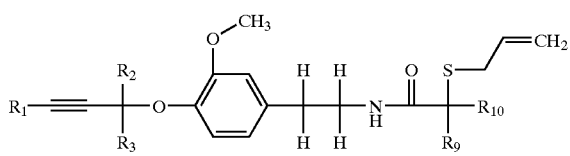

wherein the combination of the groups $R_1$, $R_2$, $R_3$, $R_9$ and $R_{10}$ corresponds each to one row in table A.

TABLE 32

Compounds represented by the Formula I.32

(I.32)

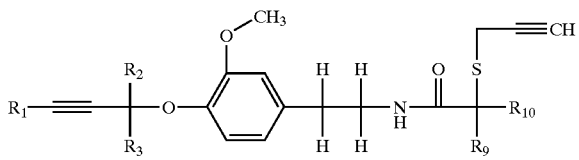

wherein the combination of the groups $R_1$, $R_2$, $R_3$, $R_9$ and $R_{10}$ corresponds each to one row in table A.

TABLE 33

Compounds represented by the Formula I.33

(I.33)

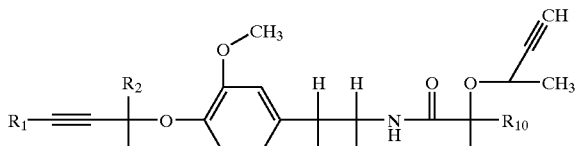

wherein the combination of the groups $R_1$, $R_2$, $R_3$, $R_9$ and $R_{10}$ corresponds each to one row in table A.

TABLE 34

Compounds represented by the Formula I.34

(I.34)

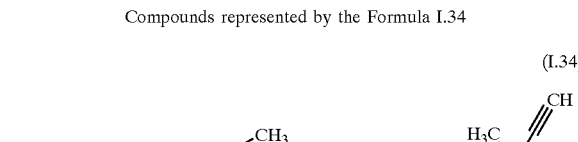

wherein the combination of the groups $R_1$, $R_2$, $R_3$, $R_9$ and $R_{10}$ corresponds each to one row in table A.

TABLE 35

Compounds represented by the Formula I.35

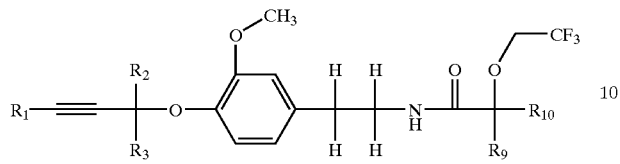

(I.35)

wherein the combination of the groups $R_1$, $R_2$, $R_3$, $R_9$ and $R_{10}$ corresponds each to one row in table A.

TABLE A (Ph designates phenyl)

| No. | $R_1$ | $R_2$ | $R_3$ | $R_9$ | $R_{10}$ |
|---|---|---|---|---|---|
| 001 | H | H | H | H | Ph |
| 002 | H | H | H | H | naphthyl |
| 003 | H | H | H | H | 2-thienyl |
| 004 | H | H | H | H | 5-chloro-2-thienyl |
| 005 | H | H | H | H | 5-bromo-2-thienyl |
| 006 | H | H | H | H | 4-bromo-2-thienyl |
| 007 | H | H | H | H | 5-methyl-2-thienyl |
| 008 | H | H | H | H | 3-thienyl |
| 009 | H | H | H | H | 2-furyl |
| 010 | H | H | H | H | 5-methyl-2-furyl |
| 011 | H | H | H | H | 3-methyl-5-isoxazolyl |

TABLE A-continued
(Ph designates phenyl)
| No. | R₁ | R₂ | R₃ | R₉ | R₁₀ |
|---|---|---|---|---|---|
| 012 | H | H | H | H | 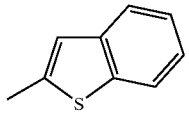 |
| 013 | H | H | H | H | 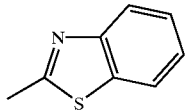 |
| 014 | H | H | H | H | 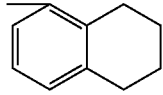 |
| 015 | H | H | H | H | 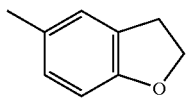 |
| 016 | H | H | H | H | 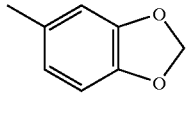 |
| 017 | H | H | H | H | 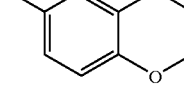 |
| 018 | H | H | H | H | 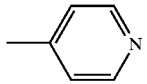 |
| 019 | H | H | H | H | 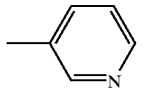 |
| 020 | H | H | H | H | 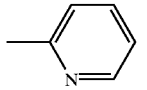 |
| 021 | H | H | H | H | 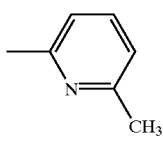 |
| 022 | H | H | H | H | 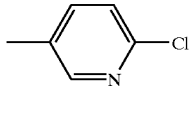 |
| 023 | H | H | H | H | 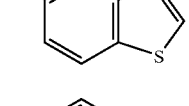 |
| 024 | H | H | H | H | 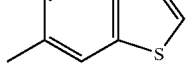 |

TABLE A-continued (Ph designates phenyl)

| No. | R₁ | R₂ | R₃ | R₉ | R₁₀ |
|---|---|---|---|---|---|
| 025 | H | H | H | H | 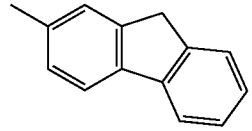 |
| 026 | H | H | H | H | 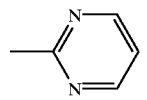 |
| 027 | H | H | H | H | 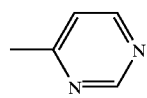 |
| 028 | H | H | H | H | 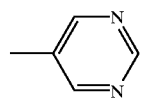 |
| 029 | H | H | H | H | 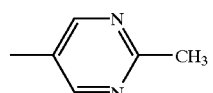 |
| 030 | H | H | H | H | 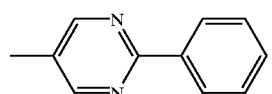 |
| 031 | H | H | H | H | 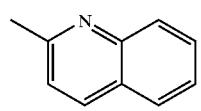 |
| 032 | H | H | H | H | 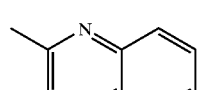 |
| 033 | H | H | H | H | 2-CH₃—Ph |
| 034 | H | H | H | H | 3-CH₃—Ph |
| 035 | H | H | H | H | 3-CF₃—Ph |
| 036 | H | H | H | H | 2-F—Ph |
| 037 | H | H | H | H | 3-F—Ph |
| 038 | H | H | H | H | 4-H₂C=CH—Ph |
| 039 | H | H | H | H | 4-HC≡C—Ph |
| 040 | H | H | H | H | 4-CH₃—CH₂—CH₂—Ph |
| 041 | H | H | H | H | 4-(CH₃)₂CH—Ph |
| 042 | H | H | H | H | 4-(CH₃)₃C—Ph |
| 043 | H | H | H | H | 4-CH₃—CH₂O—Ph |
| 044 | H | H | H | H | 4-PhO—Ph |
| 045 | H | H | H | H | 4-PhCH₂O—Ph |
| 046 | H | H | H | H | 4-HC≡CCH₂O—Ph |
| 047 | H | H | H | H | 3-CH₃O—Ph |
| 048 | H | H | H | H | 4-CH₃O—Ph |
| 049 | H | H | H | H | 3-CF₃O—Ph |
| 050 | H | H | H | H | 4-CH₃S—Ph |
| 051 | H | H | H | H | 4-CF₃S—Ph |
| 052 | H | H | H | H | 4-CH₃SO₂—Ph |
| 053 | H | H | H | H | 3-CN—Ph |
| 054 | H | H | H | H | 4-CN—Ph |
| 055 | H | H | H | H | 4-NO₂—Ph |
| 056 | H | H | H | H | 4-CH₃O₂C—Ph |
| 057 | H | H | H | H | 3-I—Ph |
| 058 | H | H | H | H | 4-I—Ph |
| 059 | H | H | H | H | 2-Br—Ph |

TABLE A-continued (Ph designates phenyl)

| No. | $R_1$ | $R_2$ | $R_3$ | $R_9$ | $R_{10}$ |
|---|---|---|---|---|---|
| 060 | H | H | H | H | 3-Br—Ph |
| 061 | H | H | H | H | 2-Cl—Ph |
| 062 | H | H | H | H | 3-Cl—Ph |
| 063 | H | H | H | H | 3,5-$F_2$—Ph |
| 064 | H | H | H | H | 3,5-$Br_2$—Ph |
| 065 | H | H | H | H | 3,5-$Cl_2$—Ph |
| 066 | H | H | H | H | 2,3-$Cl_2$—Ph |
| 067 | H | H | H | H | 2,4-$Cl_2$—Ph |
| 068 | H | H | H | H | 2,6-$Cl_2$—Ph |
| 069 | H | H | H | H | 3,4,5-$Cl_3$—Ph |
| 070 | H | H | H | H | 2,3,5-$Cl_3$—Ph |
| 071 | H | H | H | H | 3,4-$(CH_3O)_2$—Ph |
| 072 | H | H | H | H | 3,5-$(CH_3)_2$—Ph |
| 073 | H | H | H | H | 3-Cl-4-CN—Ph |
| 074 | H | H | H | H | 4-Cl-3-CN—Ph |
| 075 | H | H | H | H | 4-Br-2-F—Ph |
| 076 | H | H | H | H | 3-$CH_3$-4-$CH_3O$—Ph |
| 077 | H | H | H | H | 3-F-4-$CH_3O$—Ph |
| 078 | H | H | H | H | 4-F—Ph |
| 079 | H | H | H | $CH_3$ | 4-F—Ph |
| 080 | $CH_3$ | H | H | H | 4-F—Ph |
| 081 | $CH_2CH_3$ | H | H | H | 4-F—Ph |
| 082 | $C_3H_7$-i | H | H | H | 4-F—Ph |
| 083 | $C_3H_5$-cycl | H | H | H | 4-F—Ph |
| 084 | H | H | H | H | 4-Cl—Ph |
| 085 | H | H | H | $CH_3$ | 4-Cl—Ph |
| 086 | $CH_3$ | H | H | H | 4-Cl—Ph |
| 087 | $CH_2CH_3$ | H | H | H | 4-Cl—Ph |
| 088 | $C_3H_7$-i | H | H | H | 4-Cl—Ph |
| 089 | $C_3H_5$-cycl | H | H | H | 4-Cl—Ph |
| 090 | H | H | H | H | 4-Br—Ph |
| 091 | H | H | H | $CH_3$ | 4-Br—Ph |
| 092 | $CH_3$ | H | H | H | 4-Br—Ph |
| 093 | $CH_2CH_3$ | H | H | H | 4-Br—Ph |
| 094 | $C_3H_7$-i | H | H | H | 4-Br—Ph |
| 095 | $C_3H_5$-cycl | H | H | H | 4-Br—Ph |
| 096 | H | H | H | H | 4-$CH_3$—Ph |
| 097 | H | H | H | $CH_3$ | 4-$CH_3$—Ph |
| 098 | $CH_3$ | H | H | H | 4-$CH_3$—Ph |
| 099 | $CH_2CH_3$ | H | H | H | 4-$CH_3$—Ph |
| 100 | $C_3H_7$-i | H | H | H | 4-$CH_3$—Ph |
| 101 | $C_3H_5$-cycl | H | H | H | 4-$CH_3$—Ph |
| 102 | H | H | H | H | 4-$CH_3$—$CH_2$—Ph |
| 103 | H | H | H | $CH_3$ | 4-$CH_3$—$CH_2$—Ph |
| 104 | $CH_3$ | H | H | H | 4-$CH_3$—$CH_2$—Ph |
| 105 | $CH_2CH_3$ | H | H | H | 4-$CH_3$—$CH_2$—Ph |
| 106 | $C_3H_7$-i | H | H | H | 4-$CH_3$—$CH_2$—Ph |
| 107 | $C_3H_5$-cycl | H | H | H | 4-$CH_3$—$CH_2$—Ph |
| 108 | H | H | H | H | 3,4-$F_2$—Ph |
| 109 | H | H | H | $CH_3$ | 3,4-$F_2$—Ph |
| 110 | $CH_3$ | H | H | H | 3,4-$F_2$—Ph |
| 111 | $CH_2CH_3$ | H | H | H | 3,4-$F_2$—Ph |
| 112 | $C_3H_7$-i | H | H | H | 3,4-$F_2$—Ph |
| 113 | $C_3H_5$-cycl | H | H | H | 3,4-$F_2$—Ph |
| 114 | H | H | H | H | 3,4-$Cl_2$—Ph |
| 115 | H | H | H | $CH_3$ | 3,4-$Cl_2$—Ph |
| 116 | $CH_3$ | H | H | H | 3,4-$Cl_2$—Ph |
| 117 | $CH_2CH_3$ | H | H | H | 3,4-$Cl_2$—Ph |
| 118 | $C_3H_7$-i | H | H | H | 3,4-$Cl_2$—Ph |
| 119 | $C_3H_5$-cycl | H | H | H | 3,4-$Cl_2$—Ph |
| 120 | H | H | H | H | 3,4-$Br_2$—Ph |
| 121 | H | H | H | $CH_3$ | 3,4-$Br_2$—Ph |
| 122 | $CH_3$ | H | H | H | 3,4-$Br_2$—Ph |
| 123 | $CH_2CH_3$ | H | H | H | 3,4-$Br_2$—Ph |
| 124 | $C_3H_7$-i | H | H | H | 3,4-$Br_2$—Ph |
| 125 | $C_3H_5$-cycl | H | H | H | 3,4-$Br_2$—Ph |
| 126 | H | H | H | H | 3-Cl-4-F—Ph |
| 127 | H | H | H | $CH_3$ | 3-Cl-4-F—Ph |
| 128 | $CH_3$ | H | H | H | 3-Cl-4-F—Ph |
| 129 | $CH_2CH_3$ | H | H | H | 3-Cl-4-F—Ph |
| 130 | $C_3H_7$-i | H | H | H | 3-Cl-4-F—Ph |
| 131 | $C_3H_5$-cycl | H | H | H | 3-Cl-4-F—Ph |
| 132 | H | H | H | H | 4-Cl-3-F—Ph |
| 133 | H | H | H | $CH_3$ | 4-Cl-3-F—Ph |
| 134 | $CH_3$ | H | H | H | 4-Cl-3-F—Ph |

TABLE A-continued (Ph designates phenyl)

| No. | $R_1$ | $R_2$ | $R_3$ | $R_9$ | $R_{10}$ |
|---|---|---|---|---|---|
| 135 | $CH_2CH_3$ | H | H | H | 4-Cl-3-F—Ph |
| 136 | $C_3H_7$-i | H | H | H | 4-Cl-3-F—Ph |
| 137 | $C_3H_5$-cycl | H | H | H | 4-Cl-3-F—Ph |
| 138 | H | H | H | H | 3-Cl-4-$CH_3$—Ph |
| 139 | H | H | H | $CH_3$ | 3-Cl-4-$CH_3$—Ph |
| 140 | $CH_3$ | H | H | H | 3-Cl-4-$CH_3$—Ph |
| 141 | $CH_2CH_3$ | H | H | H | 3-Cl-4-$CH_3$—Ph |
| 142 | $C_3H_7$-i | H | H | H | 3-Cl-4-$CH_3$—Ph |
| 143 | $C_3H_5$-cycl | H | H | H | 3-Cl-4-$CH_3$—Ph |
| 144 | H | H | H | H | 4-Cl-3-$CH_3$—Ph |
| 145 | H | H | H | $CH_3$ | 4-Cl-3-$CH_3$—Ph |
| 146 | $CH_3$ | H | H | H | 4-Cl-3-$CH_3$—Ph |
| 147 | $CH_2CH_3$ | H | H | H | 4-Cl-3-$CH_3$—Ph |
| 148 | $C_3H_7$-i | H | H | H | 4-Cl-3-$CH_3$—Ph |
| 149 | $C_3H_5$-cycl | H | H | H | 4-Cl-3-$CH_3$—Ph |
| 150 | H | H | H | H | 3-Cl-4-$CF_3$—Ph |
| 151 | H | H | H | $CH_3$ | 3-Cl-4-$CF_3$—Ph |
| 152 | $CH_3$ | H | H | H | 3-Cl-4-$CF_3$—Ph |
| 153 | $CH_2CH_3$ | H | H | H | 3-Cl-4-$CF_3$—Ph |
| 154 | $C_3H_7$-i | H | H | H | 3-Cl-4-$CF_3$—Ph |
| 155 | $C_3H_5$-cycl | H | H | H | 3-Cl-4-$CF_3$—Ph |
| 156 | H | H | H | H | 4-Cl-3-$CF_3$—Ph |
| 157 | H | H | H | $CH_3$ | 4-Cl-3-$CF_3$—Ph |
| 158 | $CH_3$ | H | H | H | 4-Cl-3-$CF_3$—Ph |
| 159 | $CH_2CH_3$ | H | H | H | 4-Cl-3-$CF_3$—Ph |
| 160 | $C_3H_7$-i | H | H | H | 4-Cl-3-$CF_3$—Ph |
| 161 | $C_3H_5$-cycl | H | H | H | 4-Cl-3-$CF_3$—Ph |
| 162 | H | H | H | H | 4-Br-3-Cl—Ph |
| 163 | H | H | H | $CH_3$ | 4-Br-3-Cl—Ph |
| 164 | $CH_3$ | H | H | H | 4-Br-3-Cl—Ph |
| 165 | $CH_2CH_3$ | H | H | H | 4-Br-3-Cl—Ph |
| 166 | $C_3H_7$-i | H | H | H | 4-Br-3-Cl—Ph |
| 167 | $C_3H_5$-cycl | H | H | H | 4-Br-3-Cl—Ph |
| 168 | H | H | H | H | 3-Br-4-Cl—Ph |
| 169 | H | H | H | $CH_3$ | 3-Br-4-Cl—Ph |
| 170 | $CH_3$ | H | H | H | 3-Br-4-Cl—Ph |
| 171 | $CH_2CH_3$ | H | H | H | 3-Br-4-Cl—Ph |
| 172 | $C_3H_7$-i | H | H | H | 3-Br-4-Cl—Ph |
| 173 | $C_3H_5$-cycl | H | H | H | 3-Br-4-Cl—Ph |
| 174 | H | H | H | H | 3-Br-4-F—Ph |
| 175 | H | H | H | $CH_3$ | 3-Br-4-F—Ph |
| 176 | $CH_3$ | H | H | H | 3-Br-4-F—Ph |
| 177 | $CH_2CH_3$ | H | H | H | 3-Br-4-F—Ph |
| 178 | $C_3H_7$-i | H | H | H | 3-Br-4-F—Ph |
| 179 | $C_3H_5$-cycl | H | H | H | 3-Br-4-F—Ph |
| 180 | H | H | H | H | 4-Br-3-F—Ph |
| 181 | H | H | H | $CH_3$ | 4-Br-3-F—Ph |
| 182 | $CH_3$ | H | H | H | 4-Br-3-F—Ph |
| 183 | $CH_2CH_3$ | H | H | H | 4-Br-3-F—Ph |
| 184 | $C_3H_7$-i | H | H | H | 4-Br-3-F—Ph |
| 185 | $C_3H_5$-cycl | H | H | H | 4-Br-3-F—Ph |
| 186 | H | H | H | H | 3-Br-4-$CH_3$—Ph |
| 187 | H | H | H | $CH_3$ | 3-Br-4-$CH_3$—Ph |
| 188 | $CH_3$ | H | H | H | 3-Br-4-$CH_3$—Ph |
| 189 | $CH_2CH_3$ | H | H | H | 3-Br-4-$CH_3$—Ph |
| 190 | $C_3H_7$-i | H | H | H | 3-Br-4-$CH_3$—Ph |
| 191 | $C_3H_5$-cycl | H | H | H | 3-Br-4-$CH_3$—Ph |
| 192 | H | H | H | H | 4-Br-3-$CH_3$—Ph |
| 193 | H | H | H | $CH_3$ | 4-Br-3-$CH_3$—Ph |
| 194 | $CH_3$ | H | H | H | 4-Br-3-$CH_3$—Ph |
| 195 | $CH_2CH_3$ | H | H | H | 4-Br-3-$CH_3$—Ph |
| 196 | $C_3H_7$-i | H | H | H | 4-Br-3-$CH_3$—Ph |
| 197 | $C_3H_5$-cycl | H | H | H | 4-Br-3-$CH_3$—Ph |
| 198 | H | H | H | H | 4-$CF_3$—Ph |
| 199 | H | H | H | $CH_3$ | 4-$CF_3$—Ph |
| 200 | $CH_3$ | H | H | H | 4-$CF_3$—Ph |
| 201 | $CH_2CH_3$ | H | H | H | 4-$CF_3$—Ph |
| 202 | $C_3H_7$-i | H | H | H | 4-$CF_3$—Ph |
| 203 | $C_3H_5$-cycl | H | H | H | 4-$CF_3$—Ph |
| 204 | H | H | H | H | 4-$CF_3O$—Ph |
| 205 | H | H | H | $CH_3$ | 4-$CF_3O$—Ph |
| 206 | $CH_3$ | H | H | H | 4-$CF_3O$—Ph |
| 207 | $CH_2CH_3$ | H | H | H | 4-$CF_3O$—Ph |
| 208 | $C_3H_7$-i | H | H | H | 4-$CF_3O$—Ph |
| 209 | $C_3H_5$-cycl | H | H | H | 4-$CF_3O$—Ph |

TABLE A-continued (Ph designates phenyl)

| No. | R₁ | R₂ | R₃ | R₉ | R₁₀ |
|-----|----|----|----|----|-----|
| 210 | H | H | H | H | 3,4-(CH₃)₂-Ph |
| 211 | H | H | H | CH₃ | 3,4-(CH₃)₂-Ph |
| 212 | CH₃ | H | H | H | 3,4-(CH₃)₂-Ph |
| 213 | CH₂CH₃ | H | H | H | 3,4-(CH₃)₂-Ph |
| 214 | C₃H₇-i | H | H | H | 3,4-(CH₃)₂-Ph |
| 215 | C₃H₅-cycl | H | H | H | 3,4-(CH₃)₂-Ph |
| 216 | H | H | H | H | 2-naphthyl |
| 217 | H | H | H | CH₃ | 2-naphthyl |
| 218 | CH₃ | H | H | H | 2-naphthyl |
| 219 | CH₂CH₃ | H | H | H | 2-naphthyl |
| 220 | C₃H₇-i | H | H | H | 2-naphthyl |
| 221 | C₃H₅-cycl | H | H | H | 2-naphthyl |
| 222 | H | H | H | H | 5,6,7,8-tetrahydro-2-naphthyl |
| 223 | H | H | H | CH₃ | 5,6,7,8-tetrahydro-2-naphthyl |
| 224 | CH₃ | H | H | H | 5,6,7,8-tetrahydro-2-naphthyl |
| 225 | CH₂CH₃ | H | H | H | 5,6,7,8-tetrahydro-2-naphthyl |
| 226 | C₃H₇-i | H | H | H | 5,6,7,8-tetrahydro-2-naphthyl |
| 227 | C₃H₅-cycl | H | H | H | 5,6,7,8-tetrahydro-2-naphthyl |

TABLE A-continued
(Ph designates phenyl)
| No. | R₁ | R₂ | R₃ | R₉ | R₁₀ |
|---|---|---|---|---|---|
| 228 | H | H | H | H | 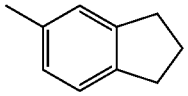 |
| 229 | H | H | H | CH₃ | 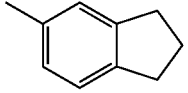 |
| 230 | CH₃ | H | H | H | 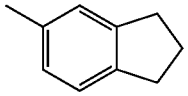 |
| 231 | CH₂CH₃ | H | H | H | 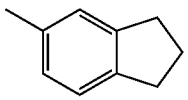 |
| 232 | C₃H₇-i | H | H | H | 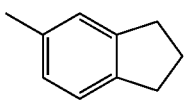 |
| 233 | C₃H₅-cycl | H | H | H | 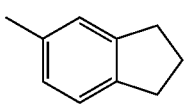 |
| 234 | H | H | H | H | 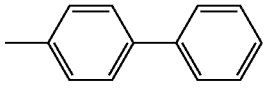 |
| 235 | H | H | H | CH₃ | 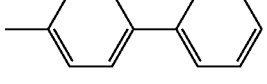 |
| 236 | CH₃ | H | H | H | 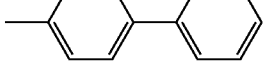 |
| 237 | CH₂CH₃ | H | H | H | 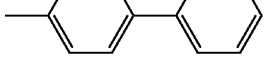 |
| 238 | C₃H₇-i | H | H | H | 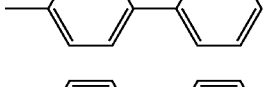 |
| 239 | C₃H₅-cycl | H | H | H | 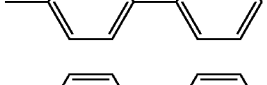 |
| 240 | H | H | H | H |  |
| 241 | H | H | H | H |  |

TABLE A-continued (Ph designates phenyl)

| No. | $R_1$ | $R_2$ | $R_3$ | $R_9$ | $R_{10}$ |
|---|---|---|---|---|---|
| 242 | H | H | H | H | 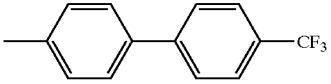 |
| 243 | H | H | H | H | 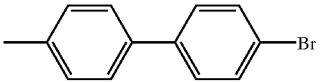 |
| 244 | H | H | H | H | 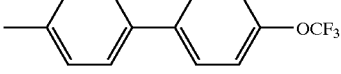 |
| 245 | H | H | H | H | 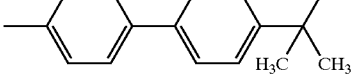 |
| 246 | H | H | H | H | 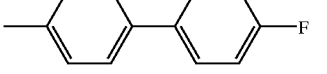 |
| 247 | H | H | H | H | 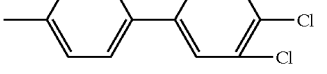 |
| 248 | H | H | H | H | 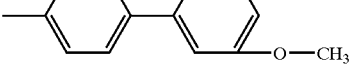 |
| 249 | H | H | H | H | 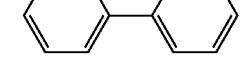 |
| 250 | H | H | H | H | 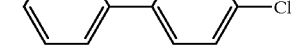 |

Formulations may be prepared analogously to those described in, for example, WO 95/30651.

BIOLOGICAL EXAMPLES

D-1: Action Against *Plasmopara viticola* on Vines
a) Residual-protective Action Vine seedlings are sprayed at the 4- to 5-leaf stage with a spray mixture (0.02% active ingredient) prepared from a wettable powder formulation of the test compound. After 24 hours, the treated plants are infected with a sporangia suspension of the fungus. Fungus infestation is evaluated after incubation for 6 days at 95–100% relative humidity and +20° C.

b) Residual-curative Action

Vine seedlings are infected at the 4- to 5-leaf stage with a sporangia suspension of the fungus. After incubation for 24 hours in a humidity chamber at 95–100% relative humidity and +20° C., the infected plants are dried and sprayed with a spray mixture (0.02% active ingredient) prepared from a wettable powder formulation of the test compound. After the spray coating has dried, the treated plants are placed in the humidity chamber again.

Fungus infestation is evaluated 6 days after infection.

Compounds of Tables 1 to 35 exhibit a good fungicidal action against *Plasmopara viticola* on vines. Compounds E1.003, E1.004, E1.009, E1.011, E1.012, E1.014, E1.018, E1.019, E1.020, E1.021, E1.022, E1.023, E1.025, E1.030, E1.031, E1.032, E1.033, E1.038, E1.040, E1.042, E1.043, E1.044, E1.045, E1.049, E1.050, E1.053, E1.055, E1.057, E1.064, E1.066E1.085, E1.089, E1.090, E1.091, E1.102, E1.108, E1.110, E1.112, E1.121, E1.125, E1.129, E1.138, E1.139 and E1.141 at 200 ppm inhibit fungal infestations in both tests D-1a) and D-1 b) by 80–100%. At the same time untreated plants showed pathogen attack of 80–100%.

D-2: Action Against Phytophthora on Tomato Plants
a) Residual-protective Action

After a cultivation period of 3 weeks, tomato plants are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 5 days at 90–100% relative humidity and +20° C.

b) Systemic Action

After a cultivation period of 3 weeks, tomato plants are watered with a spray mixture (0.02% active ingredient based on the volume of the soil) prepared from a wettable powder formulation of the test compound. Care is taken that the spray mixture does not come into contact with the parts of the plants that are above the ground. After 96 hours, the treated plants are infected with a sporangia suspension of the fungus. Fungus infestation is evaluated after incubation of the infected plants for 4 days at 90–100% relative humidity and +20° C. Compounds of Tables 1 to 35 exhibit a long-lasting effect against fungus infestation. Compounds E1.003, E1.004, E1.009, E1.011, E1.012, E1.014, E1.018, E1.019, E1.020, E1.021, E1.022, E1.023, E1.025, E1.031, E1.032, E1.033, E1.038, E1.040, E1.044, E1.045, E1.049, E1.050, E1.053, E1.055, E1.057, E1.064, E1.085, E1.089, E1.090, E1.091, E1.102, E1.08, E1.110, E1.112, E1.121, E1.125, E1.129, E1.139 and E1.141 at 200 ppm inhibit fungal infestations in both tests D-2a) and D-2b) by 80–100%. At the same time untreated plants showed pathogen attack of 80–100%.

D-3: Action Against Phytophthora on Potato Plants
a) Residual-protective Action

2–3 week old potato plants (Bintje variety) are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 4 days at 90–100% relative humidity and +20° C.

b) Systemic Action

2–3 week old potato plants (Bintje variety) are watered with a spray mixture (0.02% active ingredient based on the volume of the soil) prepared from a wettable powder formulation of the test compound. Care is taken that the spray mixture does not come into contact with the parts of the plants that are above the ground. After 48 hours, the treated plants are infected with a sporangia suspension of the fungus. Fungus infestation is evaluated after incubation of the infected plants for 4 days at 90–100% relative humidity and +20° C. Fungal infestation is effectively controlled with compounds of Tables 1 to 35. Compounds E1.003, E1.004, E1.009, E1.011, E1.012, E1.019, E1.020, E1.021, E1.022, E1.025, E1.031, E1.032, E1.033, E1.038, E1.045, E1.049, E1.050, E1.053, E1.085, E1.089, E1.090, E1.091, E1.102, E1.110, E1.112, E1.121, E1.125, E1.129 at 200 ppm inhibit fungal infestations in both tests D-3a) and D-3b) by 80–100%. At the same time untreated plants showed pathogen attack of 80–100%.

What is claimed is:

1. Compounds of formula I

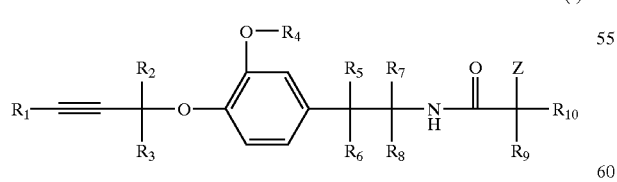

(I)

including the optical isomers thereof and mixtures of such isomers, wherein $R_1$ is hydrogen, alkyl, cycloalkyl or optionally substituted aryl, $R_2$ and $R_3$ are each independently hydrogen or alkyl, $R_4$ is alkyl, alkenyl or alkynyl, $R_5$, $R_6$, $R_7$, and $R_8$ are each independently hydrogen or alkyl, $R_9$ is hydrogen, optionally substituted alkyl, optionally substituted alkenyl or optionally substituted alkynyl, $R_{10}$ is optionally substituted aryl or optionally substituted heteroaryl, and Z is halogen, optionally substituted aryloxy, optionally substituted alkoxy, optionally substituted alkenyloxy, optionally substituted alkynyloxy, optionally substituted arylthio, optionally substituted alkylthio, optionally substituted alkenylthio, optionally substituted alkynylthio, optionally substituted alkylsulfinyl, optionally substituted alkenylsulfinyl, optionally substituted alkynylsulfinyl, optionally substituted alkylsulfonyl, optionally substituted alkenylsulfonyl or optionally substituted alkynylsulfonyl.

2. A compound according to claim 1 wherein $R_1$ is hydrogen, alkyl, cycloalkyl, phenyl or naphthyl; phenyl and naphthyl being optionally substituted by substituents selected from the group comprising alkyl, alkenyl, alkynyl, cycloalkyl, cycloalkyl-alkyl, phenyl and phenylalkyl, where all these groups may in turn be substituted by one or several halogens; alkoxy; alkenyloxy; alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl; or alkynyloxycarbonyl; and $R_2$ and $R_3$ are independently of each other hydrogen or $C_1$–$C_4$alkyl; and $R_4$ is $C_1$–$C_8$alkyl, $C_2$–$C_8$alkenyl, or $C_2$–$C_8$alkynyl; and $R_5$, $R_6$, $R_7$ and $R_8$ are independently of each other hydrogen or $C_1$–$C_4$alkyl; and $R_9$ is hydrogen, $C_1$–$C_4$alkyl, $C_1$–$C_4$haloalkyl, $C_3$–$C_4$alkenyl or $C_3$–$C_4$alkynyl; and $R_{10}$ is aryl or heteroaryl, each optionally substituted with substituents selected from to group comprising alkyl, alkenyl, alkynyl, cycloalkyl, cycloalkyl-alkyl, phenyl and phenylalkyl, where all these groups may be substituted with one or more substituents selected from the group comprising halogen; alkoxy, alkenyloxy, alkynyloxy; alkoxy-alkyl; haloalkoxy; alkylthio; haloalkylthio; alkylsulfonyl; formyl; alkanoyl; hydroxy; cyano; nitro; amino; alkylamino; dialkylamino; carboxyl; alkoxycarbonyl; alkenyloxycarbonyl and alkynyloxycarbonyl; and Z is halogen, optionally substituted aryloxy or arylthio wherein in each the aryl may be optionally substituted by one or more substituents selected from the group comprising. halogen, $C_1$–$C_8$alkoxy, $C_2$–$C_8$alkenyloxy, $C_2$–$C_8$alkynyloxy, $C_1$–$C_8$alkoxy-$C_1$–$C_8$alkyl, $C_1$–$C_8$haloalkoxy, $C_1$–$C_8$alkylthio, $C_1$–$C_8$haloalkylthio, $C_1$–$C_8$alkylsulfonyl, formyl, $C_2$–$C_8$alkanoyl, hydroxy, halogen, cyano, nitro, amino, $C_1$–$C_8$alkylamino di-$C_1$–$C_8$alkylamino, carboxyl and $C_1$–$C_8$alkoxycarbonyl; or is optionally substituted $C_1$–$C_8$alkoxy, optionally substituted $C_2$–$C_8$alkenyloxy, optionally substituted $C_2$–$C_8$alkynyloxy, optionally substituted $C_1$–$C_8$alkylthio, optionally substituted $C_2$–$C_8$alkenylthio, optionally substituted $C_2$–$C_8$alkynylthio, optionally substituted $C_1$–$C_8$alkylsulfinyl, optionally substituted $C_2$–$C_8$alkenylsulfinyl, optionally substituted $C_2$–$C_8$alkynylsulfinyl, optionally substituted $C_1$–$C_8$alkylsulfonyl, optionally substituted $C_2$–$C_8$alkenylsulfonyl or optionally substituted $C_2$–$C_8$alkynylsulfonyl wherein each alkyl, alkenyl or alkynyl group may carry one or more substituents selected from the group comprising halogen, $C_1$–$C_4$alkyl, $C_1$–$C_4$alkoxy, $C_1$–$C_4$alkylthio, $C_3$–$C_6$cycloalkyl, nitro, cyano, hydroxy, phenyl, mercapto, $C_1$–$C_4$alkylcarbonyl and $C_1$–$C_4$alkoxycarbonyl.

3. A compound according to claim 1 wherein $R_1$ is hydrogen, $C_1$–$C_8$alkyl, $C_3$–$C_8$cycloalkyl, phenyl or naphthyl; phenyl and naphthyl being optionally substituted by one to three substituents selected from the group comprising $C_1$–$C_8$alkyl, $C_2$–$C_8$alkenyl, $C_2$–$C_8$alkynyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, $C_1$–$C_8$alkylsulfonyl, halogen, cyano, nitro and $C_1$–$C_8$alkoxycarbonyl; and $R_2$ and $R_3$ are hydrogen; and $R_4$ is $C_1$–$C_6$alkyl; and $R_5$, $R_6$ and $R_7$ are hydrogen and $R_8$ is hydrogen, methyl or ethyl, preferably methyl; and $R_9$ is hydrogen or $C_1$–$C_4$alkyl; and $R_{10}$ is phenyl, naphthyl or biphenyl, each optionally substituted by one to three substituents selected from the group comprising $C_1$–$C_8$alkyl, $C_2$–$C_8$alkenyl, $C_2$–$C_8$alkynyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, $C_1$–$C_8$alkylsulfonyl, halogen cyano, nitro and $C_1$–$C_8$alkoxycarbonyl; and Z is halogen; $C_1$–$C_8$alkoxy, $C_2$–$C_8$alkenyloxy, $C_1$–$C_8$alkynyloxy, $C_1$–$C_8$alkoxy-$C_1$–$C_8$alkoxy, $C_2$–$C_8$alkenyloxy-$C_1$–$C_8$alkoxy, $C_2$–$C_8$alkynyloxy-$C_1$–$C_8$alkoxy, $C_1$–$C_8$haloalkoxy, $C_3$–$C_8$cyclo-alkyl-$C_1$–$C_8$alkoxy, $C_1$–$C_8$alkylthio, $C_2$–$C_8$alkenylthio, $C_1$–$C_8$alkynylthio, $C_1$–$C_8$haloalkylthio, $C_3$–$C_8$cycloalkyl-$C_1$–$C_8$alkylthio, $C_1$–$C_8$alkylsulfinyl, $C_1$–$C_8$alkylsulfonyl, $C_2$–$C_8$alkenylsulfinyl, $C_2$–$C_8$alkenylsulfonyl, $C_2$–$C_8$alkynylsulfinyl or $C_2$–$C_8$alkynylsulfonyl.

4. A compound of formula I according to claim 1 wherein $R_1$ is hydrogen, $C_1$–$C_8$alkyl or phenyl optionally substituted by one to three substituents selected from the group comprising $C_1$–$C_8$alkyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, halogen, cyano, nitro and $C_1$–$C_8$alkoxycarbonyl; and $R_2$ and $R_3$ are hydrogen; and $R_4$ is $C_1$–$C_4$alkyl, and $R_5$, $R_6$ and $R_7$ are hydrogen and $R_8$ is hydrogen or methyl; and $R_9$ is hydrogen; and $R_{10}$ is phenyl, naphthyl, 1,3-biphenyl or 1,4-biphenyl, each optionally substituted by one to three substituents selected from the group comprising $C_1$–$C_8$alkyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, halogen, cyano, nitro and $C_1$–$C_8$alkoxycarbonyl; and Z is halogen; $C_1$–$C_8$alkoxy, $C_2$–$C_8$alkenyloxy, $C_2$–$C_8$alkynyloxy, $C_1$–$C_4$alkoxy-$C_1$–$C_2$alkoxy, $C_2$–$C_8$alkylthio, $C_2$–$C_8$alkenylthio or $C_2$–$C_8$alkynylthio.

5. A compound of formula I according to claim 1 wherein $R_1$ is hydrogen, $C_1$–$C_8$alkyl or $C_3$–$C_8$cycloalkyl; and $R_2$, $R_3$, $R_5$, $R_6$, $R_7$, $R_8$ and $R_9$ are hydrogen; and $R_4$ is methyl or ethyl; and $R_{10}$ is phenyl, naphthyl, 1,3-biphenyl or 1,4-biphenyl, each optionally substituted by one to three substituents selected from the group comprising $C_1$–$C_8$alkyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, halogen, cyano, nitro and $C_1$–$C_8$alkoxycarbonyl; and Z is $C_1$–$C_8$alkoxy, $C_2$–$C_6$alkenyloxy or $C_2$–$C_6$alkynyloxy.

6. A compound of formula I according to any of claims 1 to 5 wherein $R_1$ is hydrogen or $C_1$–$C_4$alkyl.

7. A compound of formula I according to claim 1 selected from the group comprising 2-(4-bromo-phenyl)-2-chloro-N-[2-(3-methoxy-4-prop-2-ynyloxy-phenyl)-ethyl]-acetamide, 2-chloro-2-(4-chloro-phenyl)-N-[2-(3-methoxy-4-prop-2-ynyloxy-phenyl)-ethyl]-acetamide, 2-chloro-2-(3,4-dichloro-phenyl)-N-[2-(3-methoxy-4-prop-2-ynyloxy-phenyl)-ethyl]-acetamide, 2-(4-bromo-phenyl)-2-methoxy-N-[2-(3-methoxy-4-prop-2-ynyloxy-phenyl)-ethyl]-acetamide, 2-(4-chloro-phenyl)-2-methoxy-N-[2-(3-methoxy-4-prop-2-ynyloxy-phenyl)-ethyl]-acetamide, 2-(3,4-dichloro-phenyl)-2-methoxy-N-[2-(3-methoxy-4-prop-2-ynyloxy-phenyl)-ethyl]-acetamide, 2-(4-bromo-phenyl)-2-ethoxy-N-[2-(3-methoxy-4-prop-2-ynyloxy-phenyl)-ethyl]-acetamide, 2-(4-chloro-phenyl)-2-ethoxy-N-[2-(3methoxy-4-prop-2-ynyloxy-phenyl)-ethyl]-acetamide, 2-(3,4-dichloro-phenyl)-2-ethoxy-N-[2-(3-methoxy-4-prop-2-ynyloxy-phenyl)-ethyl]-acetamide, 2-(4-bromo-phenyl)-N-[2-(3-methoxy-4-prop-2-ynyloxy-phenyl)-ethyl]-2-propoxy-acetamide, 2-(4-chloro-phenyl)-N-[2-(3-methoxy-4-prop-2-ynyloxy-phenyl)-ethyl]-2-propoxy-acetamide, 2-(3,4-dichloro-phenyl)-N-[2-(3-methoxy-4-prop-2-ynyloxy-phenyl)-ethyl]-2-propoxy-acetamide, 2-(4-bromo-phenyl)-2-cyclopropylmethoxy-N-[2-(3-methoxy-4-prop-2-ynyloxy-phenyl)-ethyl]-acetamide, 2-(4-chloro-phenyl)-2-cyclopropylmethoxy-N-[2-(3-methoxy-4-prop-2-ynyloxy-phenyl)-ethyl]-acetamide, 2-cyclopropylmethoxy-2-(3,4-dichloro-phenyl)-N-[2-(3-methoxy-4-prop-2-ynyloxy-phenyl)-ethyl]-acetamide, 2-(4-bromo-phenyl)-2-ethoxymethoxy-N-[2-(3-methoxy-4-prop-2-ynyloxy-phenyl)-ethyl]-acetamide, 2-(4-chloro-phenyl)-2-ethoxymethoxy-N-[2-(3-methoxy-4-prop-2-ynyloxy-phenyl)-ethyl]-acetamide, 2-(3,4-dichloro-phenyl)-2-ethoxymethoxy-N-[2-(3-methoxy-4-prop-2-ynyloxy-phenyl)-ethyl]-acetamide, 2-allyloxy-2-(4-bromo-phenyl)-N-[2-(3-methoxy-4-prop-2-ynyloxy-phenyl)-ethyl]-acetamide, 2-allyloxy-2-(4-chloro-phenyl)-N-[2-(3-methoxy-4-prop-2-ynyloxy-phenyl)-ethyl]-acetamide, 2-allyloxy-2-(3,4-dichloro-phenyl)-N-[2-(3-methoxy-4-prop-2-ynyloxy-phenyl)-ethyl]-acetamide, 2-(4-bromo-phenyl)-2-(but-2-enyloxy)-N-[2-(3-methoxy-4-prop-2-ynyloxy-phenyl)-ethyl]-acetamide, 2-(but-2-enyloxy)-2-(4-chloro-phenyl)-N-[2-(3-methoxy-4-prop-2-ynyloxy-phenyl)-ethyl]-acetamide, 2-(but-2-enyloxy)-2-(3,4-dichloro-phenyl)-N-[2-(3-methoxy-4-prop-2-ynyloxy-phenyl)-ethyl]-acetamide, 2-(4-bromo-phenyl)-N-[2-(3-methoxy-4-prop-2-ynyloxy-phenyl)-ethyl]-2-prop-2-ynyloxy-acetamide, 2-(4-chloro-phenyl)-N-[2-(3-methoxy-4-prop-2-ynyloxy-phenyl)-ethyl]-2-prop-2-ynyloxy-acetamide, 2-(3,4-dichloro-phenyl)-N-[2-(3-methoxy-4-prop-2-ynyloxy-phenyl)-ethyl]-2-prop-2-ynyloxy-acetamide, 2-biphenyl-4-yl-N-[2-(3-methoxy-4-prop-2-ynyloxy-phenyl)-ethyl]-2-prop-2-ynyloxy-acetamide, N-[2-(3-methoxy-4-prop-2-ynyloxy-phenyl)-ethyl]-2-naphthalen-2-yl-2-prop-2-ynyloxy-acetamide,
N-[2-(3-methoxy-4-prop-2-ynyloxy-phenyl)-ethyl]-2-prop-2-ynyloxy-2-p-tolyl-acetamide,
2-(4-ethyl-phenyl)-N-[2-(3-methoxy-4-prop-2-ynyloxy-phenyl)-ethyl]-2-prop-2-ynyloxy-acetamide,
N-[2-(3-methoxy-4-prop-2-ynyloxy-phenyl)-ethyl]-2-prop-2-ynyloxy-2-(4-trifluoromethyl-phenyl)-acetamide,
2-(4-bromo-phenyl)-2-but-2-ynyloxy-N-[2-(3-methoxy-4-prop-2-ynyloxy-phenyl)-ethyl]-acetamide,
2-but-2-ynyloxy-2-(4-chloro-phenyl)-N-[2-(3-methoxy-4-prop-2-ynyloxy-phenyl)-ethyl]-acetamide,
2-but-2-ynyloxy-2-(3,4-dichloro-phenyl)-N-[2-(3-methoxy-4-prop-2-ynyloxy-phenyl)-ethyl]-acetamide,
2-(4-bromo-phenyl)-N-[2-(3-methoxy-4-prop-2-ynyloxy-phenyl)-ethyl]-2-prop-2-ynylsulfanyl-acetamide,
2-(4-chloro-phenyl)-N-[2-(3-methoxy-4-prop-2-ynyloxy-phenyl)-ethyl]-2-prop-2-ynylsulfanyl-acetamide,
2-(3,4-dichloro-phenyl)-N-[2-(3-methoxy-4-prop-2-ynyloxy-phenyl)-ethyl]-2-prop-2-ynylsulfanyl-acetamide,
2-allylsulfanyl-2-(4-bromo-phenyl)-N-[2-(3-methoxy-4-prop-2-ynyloxy-phenyl)-ethyl]-acetamide,
2-allylsulfanyl-2-(4-chloro-phenyl)-N-[2-(3-methoxy-4-prop-2-ynyloxy-phenyl)-ethyl]-acetamide,
2-allylsulfanyl-2-(3,4-dichloro-phenyl)-N-[2-(3-methoxy-4-prop-2-ynyloxy-phenyl)-ethyl]-acetamide,
2-(4-bromo-phenyl)-N-[2-(3-methoxy-4-pent-2-ynyloxy-phenyl)-ethyl]-2-prop-2-ynyloxy-acetamide,
2-(4-chloro-phenyl)-N-[2-(3-methoxy-4-pent-2-ynyloxy-phenyl)-ethyl]-2-prop-2-ynyloxy-acetamide,
2-(3,4-dichloro-phenyl)-N-[2-(3-methoxy-4-pent-2-ynyloxy-phenyl)-ethyl]-2-prop-2-ynyloxy-acetamide,
2-(4-fluoro-phenyl)-N-[2-(3-methoxy-4-prop-2-ynyloxy-phenyl)-ethyl]-2-prop-2-ynyloxy-acetamide,
2-(3,4-difluoro-phenyl)-N-[2-(3-methoxy-4-prop-2-ynyloxy-phenyl)-ethyl]-2-prop-2-ynyloxy-acetamide,
2-(4-chloro-3-fluoro-phenyl)-N-[2-(3-methoxy-4-prop-2-ynyloxy-phenyl)-ethyl]-2-prop-2-ynyloxy-acetamide, and
2-(3-chloro-4-fluoro-phenyl)-N-[2-(3-methoxy-4-prop-2-ynyloxy-phenyl)-ethyl]-2-prop-2-ynyloxy-acetamide.

8. A process for the preparation of a compound of formula I according to claim 1, which comprises reacting
a) reacting the phenol of formula IV

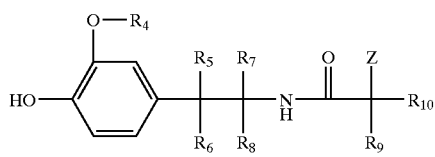

wherein $R_4$, $R_5$, $R_6$, $R_7$, $R_8$, $R_9$, $R_{10}$ and Z are as defined for formula I with a compound of formula V

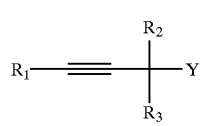

wherein $R_1$, $R_2$ and $R_3$ are as defined for formula I and wherein Y is a leaving group; or
b) reacting the acid of formula II with an amine of formula VI

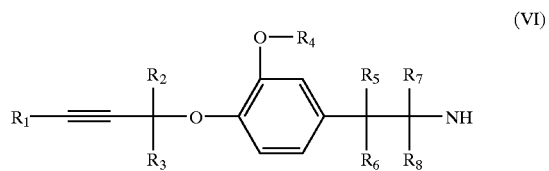

wherein $R_1$, $R_2$, $R_3$, $R_4$, $R_5$, $R_6$, $R_7$ and $R_8$ are as defined for formula I.

9. A composition for controlling and protecting against phytopathogenic microorganisms, comprising a compound of formula I according to claim 1 as active ingredient together with a suitable carrier.

10. A composition according to claim 9 which comprises at least one additional fungicidally active compound, preferably selected from the group consisting of cymoxanil, trifloxystrobin, azoxystrobin, picoxystrobin, chlorothalonil, metalaxyl, metalaxyl-M, pyraclostrobin (BAS500F), dimethomorph, fosetyl-Al, copper-salts, acibenzolar-S-methyl, fludioxonil, mancozeb, folpet, fluazinam, iprovalicarb, zoxamid and (S)-2-(methylsulfonyl-amino)-3-methyl-butyric acid N-[2-{3-methoxy-4-(3-(4-chlorophenyl)-2-propyn-1-yloxy)-phenyl}-ethyl]-amide.

11. A method of controlling and preventing an infestation of crop plants by phytopathogenic microorganisms, which comprises the application of a compound of formula I according to claim 1 as active ingredient to the plant, to parts of plants or to the locus thereof.

12. A method according to claim 11, wherein the phytopathogenic microorganisms are fungal organisms.

13. A process for the preparation of a compound of formula Ia according to claim 1

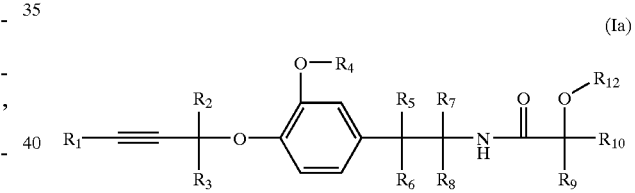

wherein $R_1$, $R_2$, $R_3$, $R_4$, $R_5$, $R_6$, $R_7$, $R_8$, $R_9$ and $R_{10}$ are as defined for formula I in claim 1 and $R_{12}$ is alkyl, alkenyl or alkynyl, which process comprises reacting
a) a compound of formula XIII

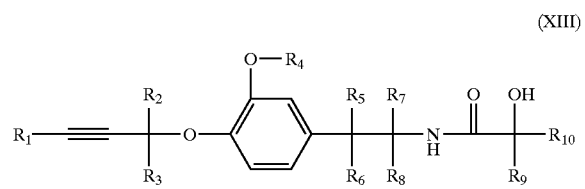

with a compound of formula XIV

wherein $R_{12}$ is alkyl, alkenyl or alkynyl and Y is a leaving group, e.g. bromine or chlorine or a tosyl, mesyl or trifluoromethylsulfonyl, or
b) a compound of formula XV

wherein $R_{12}$ is alkyl, alkenyl or alkynyl, with a compound of formula XVI

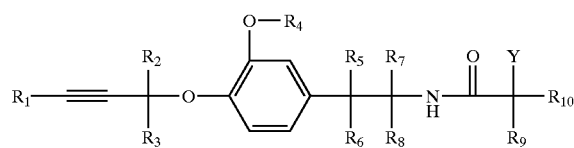
(XVI)

or a compound of formula XVIa

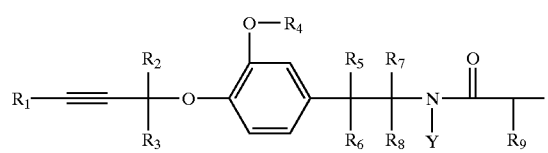
(XVIa)

wherein $R_1$, $R_2$, $R_3$, $R_4$, $R_5$, $R_6$, $R_7$, $R_8$, $R_9$ and $R_{10}$ are as defined for formula I in claim 1.

14. A process for the preparation of a compound of formula Ib according to claim 1

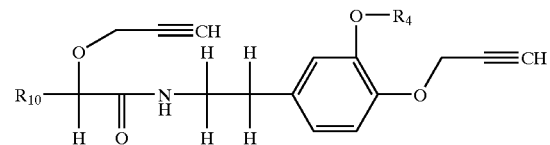
(Ib)

which comprises reacting a compound of formula

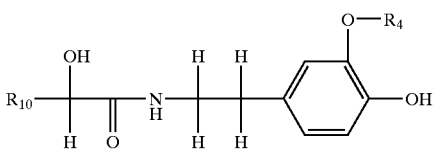
(XXI)

wherein $R_4$ and $R_{10}$ are as defined for formula I in claim 1, with a propargylating agent of formula XXII

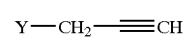
(XXII)

wherein Y is a leaving group, e.g. bromine or chlorine or a tosyl, mesyl or trifluoromethylsulfonyl.

* * * * *